(12) United States Patent
Widgerow et al.

(10) Patent No.: US 10,493,011 B2
(45) Date of Patent: Dec. 3, 2019

(54) PEPTIDE COMPOSITIONS AND METHODS FOR AMELIORATING SKIN LAXITY AND BODY CONTOUR

(71) Applicant: Alastin Skincare, Inc., Carlsbad, CA (US)

(72) Inventors: Alan David Widgerow, Irvine, CA (US); John A. Garruto, Encinitas, CA (US)

(73) Assignee: Alastin Skincare, Inc., Carlsbad, CA (US)

( * ) Notice: Subject to any disclaimer, the term of this patent is extended or adjusted under 35 U.S.C. 154(b) by 0 days.

(21) Appl. No.: 16/053,674

(22) Filed: Aug. 2, 2018

(65) Prior Publication Data

US 2019/0038539 A1    Feb. 7, 2019

Related U.S. Application Data

(60) Provisional application No. 62/696,256, filed on Jul. 10, 2018, provisional application No. 62/541,036, filed on Aug. 3, 2017, provisional application No. 62/541,022, filed on Aug. 3, 2017.

(51) Int. Cl.
*A61K 8/64* (2006.01)
*A61Q 19/00* (2006.01)
*A61Q 19/08* (2006.01)

(52) U.S. Cl.
CPC ............... *A61K 8/64* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | |
|---|---|---|
| 3,299,037 A | 1/1967 | Boissonnas et al. |
| 3,415,805 A | 12/1968 | Siedel et al. |
| 5,534,420 A | 7/1996 | Debono et al. |
| 5,814,610 A | 9/1998 | Bab et al. |
| 5,993,787 A | 11/1999 | Sun et al. |
| 6,939,854 B2 | 9/2005 | Priestley |
| 6,974,799 B2 | 12/2005 | Lintner |
| 7,361,634 B2 | 4/2008 | Trotter et al. |
| 7,566,464 B2 | 7/2009 | Belfer |
| 7,632,527 B2 | 12/2009 | Jochim et al. |
| 7,750,115 B2 | 7/2010 | Oka et al. |
| 7,772,196 B2 | 8/2010 | Yedgar |
| 7,943,156 B2 | 5/2011 | Alminana et al. |
| 8,021,695 B2 | 9/2011 | Gruber |
| 8,025,907 B2 | 9/2011 | Belfer |
| 8,067,370 B2 | 11/2011 | Trotter et al. |
| 8,071,139 B2 | 12/2011 | Widgerow |
| 8,076,312 B2 | 12/2011 | Yedgar |
| 8,183,204 B2 | 5/2012 | Pickart |
| 8,304,393 B2 | 11/2012 | Oka et al. |
| 8,394,371 B2 | 3/2013 | Laurent-Applegate et al. |
| 8,449,879 B2 | 5/2013 | Laurent-Applegate et al. |
| 8,529,925 B2 | 9/2013 | Alexiades-Armenakas |
| 8,530,426 B2 | 9/2013 | Lintner et al. |
| 8,575,106 B2 | 11/2013 | Santhanam et al. |
| 8,591,961 B2 | 11/2013 | Widgerow |
| 8,697,656 B2 | 4/2014 | Fournial et al. |
| 8,710,010 B2 | 4/2014 | Van et al. |
| 8,710,011 B2 | 4/2014 | Garcia et al. |
| 8,796,315 B2 | 8/2014 | McCord |
| 8,815,266 B2 | 8/2014 | Carreno et al. |
| 8,901,103 B2 | 12/2014 | Yedgar |
| 8,906,426 B2 | 12/2014 | Galderisi |
| 8,916,539 B2 | 12/2014 | Yedgar et al. |
| 8,946,166 B2 | 2/2015 | Garcia et al. |
| 8,962,565 B2 | 2/2015 | Dal et al. |
| 8,993,716 B2 | 3/2015 | Carreno et al. |
| 9,000,033 B2 | 4/2015 | Gruber |
| 9,067,967 B2 | 6/2015 | García et al. |
| 9,078,903 B2 | 7/2015 | Laurent-Applegate et al. |
| 9,144,434 B1 | 9/2015 | Rodan et al. |
| 9,180,157 B2 | 11/2015 | Widgerow |
| 9,180,158 B2 | 11/2015 | Widgerow |
| 9,248,160 B1 | 2/2016 | Obagi et al. |
| 9,265,792 B2 * | 2/2016 | Riley .................. A61K 31/728 |
| 9,266,921 B2 | 2/2016 | Garcia et al. |
| 9,278,122 B2 | 3/2016 | Laurent-Applegate et al. |
| 9,315,564 B2 | 4/2016 | Serraima et al. |
| 9,333,152 B2 | 5/2016 | Ferrer et al. |
| 9,364,414 B2 | 6/2016 | Domloge et al. |
| 9,376,659 B2 | 6/2016 | Rao et al. |
| 9,408,881 B2 | 8/2016 | Gruber et al. |
| 9,434,764 B2 | 9/2016 | Abdel-Malek et al. |
| 9,486,409 B2 | 11/2016 | Edelson et al. |
| 9,526,679 B2 | 12/2016 | Jang et al. |
| 9,725,483 B2 | 8/2017 | Garcia et al. |
| 9,834,580 B2 | 12/2017 | Abdel-Malek et al. |
| 2003/0166571 A1 | 9/2003 | Judd |
| 2004/0043047 A1 | 3/2004 | Dumas et al. |
| 2004/0120918 A1 | 6/2004 | Lintner et al. |
| 2005/0063932 A1 | 3/2005 | Dilallo et al. |
| 2006/0110355 A1 | 5/2006 | Blin |
| 2006/0198800 A1 | 9/2006 | Dilallo et al. |
| 2007/0048245 A1 | 3/2007 | Belfer |
| 2007/0110731 A1 | 5/2007 | Riley |

(Continued)

FOREIGN PATENT DOCUMENTS

| | | |
|---|---|---|
| CA | 2768653 A1 | 3/2011 |
| CA | 2895387 A1 | 7/2014 |

(Continued)

OTHER PUBLICATIONS

Sklirou A. et al. Hexapeptide-11 is a Novel Modulator of the Proteostasis Network in Human Diploid Fibroblasts. Redox Biology 5: 205-215, 2015. (Year: 2015).*

(Continued)

*Primary Examiner* — Ralph J Gitomer
(74) *Attorney, Agent, or Firm* — Wilson Sonsini Goodrich & Rosati

(57) ABSTRACT

Compositions and methods for amelioration of skin laxity and body contour are provided. Provided herein are compositions comprising a combination of peptides.

15 Claims, 26 Drawing Sheets
(24 of 26 Drawing Sheet(s) Filed in Color)
Specification includes a Sequence Listing.

(56) References Cited

U.S. PATENT DOCUMENTS

| | | |
|---|---|---|
| 2008/0044373 A1 | 2/2008 | Ilekti et al. |
| 2008/0107679 A1 | 5/2008 | Dilallo et al. |
| 2008/0166313 A1 | 7/2008 | Jochim et al. |
| 2008/0166314 A1 | 7/2008 | Jochim et al. |
| 2008/0171011 A1 | 7/2008 | Jochim et al. |
| 2008/0171030 A1 | 7/2008 | Jochim et al. |
| 2008/0171031 A1 | 7/2008 | Jochim et al. |
| 2008/0175928 A1 | 7/2008 | Jochim et al. |
| 2008/0181974 A1 | 7/2008 | Cauchard et al. |
| 2008/0213300 A1 | 9/2008 | Jochim et al. |
| 2009/0047226 A1 | 2/2009 | Teckenbrock et al. |
| 2009/0186826 A1 | 7/2009 | Lintner et al. |
| 2009/0285770 A1 | 11/2009 | Laboureau |
| 2010/0021401 A1* | 1/2010 | Sallander ............ A61K 38/06 424/59 |
| 2010/0183723 A1 | 7/2010 | Laurent-Applegate et al. |
| 2010/0189795 A1 | 7/2010 | Dreher |
| 2010/0316745 A1 | 12/2010 | Pellicier et al. |
| 2010/0322983 A1 | 12/2010 | Griffiths-Brophy et al. |
| 2011/0005737 A1 | 1/2011 | Plata |
| 2011/0020242 A1 | 1/2011 | Zheng et al. |
| 2011/0052676 A1 | 3/2011 | Gruber |
| 2011/0059907 A1 | 3/2011 | Gupta et al. |
| 2011/0091420 A1 | 4/2011 | Liu et al. |
| 2011/0158922 A1* | 6/2011 | Dupont ............... A61K 8/73 424/59 |
| 2011/0177140 A1 | 7/2011 | Voegeli et al. |
| 2012/0021029 A1 | 1/2012 | Garcia et al. |
| 2012/0045405 A1 | 2/2012 | Gilman et al. |
| 2012/0076842 A1 | 3/2012 | Fournial et al. |
| 2012/0128755 A1* | 5/2012 | Gruber ............... A61K 36/064 424/450 |
| 2012/0277313 A1 | 11/2012 | Kwon et al. |
| 2013/0129691 A1 | 5/2013 | Laurent-Applegate et al. |
| 2013/0224131 A1 | 8/2013 | Voegeli et al. |
| 2013/0337088 A1 | 12/2013 | Widgerow |
| 2014/0127286 A1* | 5/2014 | Doucet ............... A61K 8/64 424/450 |
| 2014/0178315 A1 | 6/2014 | Gruber et al. |
| 2014/0242134 A1 | 8/2014 | Khoshdel et al. |
| 2014/0309173 A1 | 10/2014 | Dreher |
| 2014/0315995 A1 | 10/2014 | Dreher et al. |
| 2015/0057244 A1 | 2/2015 | Yedgar et al. |
| 2015/0157728 A1 | 6/2015 | Modi |
| 2015/0183823 A1 | 7/2015 | García et al. |
| 2015/0202139 A1 | 7/2015 | Friedman |
| 2016/0000858 A1 | 1/2016 | Tittl et al. |
| 2016/0006543 A1 | 1/2016 | Winstead et al. |
| 2016/0008263 A1 | 1/2016 | Mendoza |
| 2016/0030321 A1 | 2/2016 | Dreher |
| 2016/0058693 A1 | 3/2016 | Widgerow |
| 2016/0058816 A1 | 3/2016 | Widgerow |
| 2016/0075738 A1 | 3/2016 | Ferrer et al. |
| 2017/0001438 A1 | 1/2017 | Seto et al. |
| 2017/0081508 A1 | 3/2017 | Daniere et al. |
| 2017/0101438 A1 | 4/2017 | García et al. |
| 2017/0135930 A1 | 5/2017 | Korth |
| 2017/0157014 A1 | 6/2017 | Peschard et al. |
| 2017/0202769 A1 | 7/2017 | Pilant |
| 2017/0224760 A1 | 8/2017 | Garruto et al. |
| 2017/0281507 A1 | 10/2017 | Idkowiak-Baldys et al. |
| 2017/0281508 A1 | 10/2017 | Idkowiak-Baldys et al. |
| 2017/0304178 A1 | 10/2017 | Idkowiak-Baldys et al. |
| 2018/0066016 A1 | 3/2018 | Abdel-Malek et al. |
| 2018/0289767 A1 | 10/2018 | Garruto et al. |

FOREIGN PATENT DOCUMENTS

| | | |
|---|---|---|
| CN | 104069043 A | 10/2014 |
| CN | 104523449 A | 4/2015 |
| CN | 104523554 A | 4/2015 |
| CN | 104586695 A | 5/2015 |
| CN | 104622779 * | 5/2015 |
| CN | 104622779 A | 5/2015 |
| CN | 103601792 B | 6/2016 |
| DE | 102004050563 A1 | 4/2006 |
| DE | 102004057405 A1 | 6/2006 |
| DE | 102004057406 A1 | 6/2006 |
| DE | 102005063179 A1 | 9/2006 |
| DE | 102006046076 A1 | 4/2007 |
| DE | 102005056157 A1 | 5/2007 |
| DE | 102005063062 A1 | 7/2007 |
| DE | 102005063178 A1 | 7/2007 |
| DE | 102006004955 A1 | 7/2007 |
| DE | 102006020380 A1 | 10/2007 |
| DE | 102006040903 A1 | 3/2008 |
| DE | 102006041291 A1 | 3/2008 |
| DE | 102007022448 A1 | 3/2008 |
| DE | 102007024381 A1 | 3/2008 |
| DE | 102006049672 A1 | 4/2008 |
| DE | 102006049674 A1 | 4/2008 |
| DE | 102006049675 A1 | 4/2008 |
| DE | 102007022449 A1 | 4/2008 |
| DE | 102006058611 A1 | 6/2008 |
| DE | 102006060439 A1 | 6/2008 |
| DE | 102006061829 A1 | 6/2008 |
| DE | 102006062438 A1 | 7/2008 |
| DE | 102006062501 A1 | 7/2008 |
| DE | 102006062566 A1 | 7/2008 |
| DE | 102007024384 A1 | 11/2008 |
| DE | 102007031452 A1 | 1/2009 |
| DE | 102008028821 A1 | 1/2009 |
| DE | 102008061045 A1 | 10/2009 |
| DE | 102008032179 A1 | 1/2010 |
| DE | 102009026718 A1 | 4/2010 |
| DE | 102008053883 A1 | 5/2010 |
| DE | 102008053884 A1 | 5/2010 |
| DE | 102008059703 A1 | 6/2010 |
| DE | 102008061044 A1 | 6/2010 |
| DE | 102008062398 A1 | 6/2010 |
| DE | 102009037537 A1 | 6/2010 |
| DE | 102009037900 A1 | 6/2010 |
| DE | 102009039393 A1 | 6/2010 |
| DE | 102009045981 A1 | 8/2010 |
| DE | 102008061340 A1 | 9/2010 |
| DE | 102009002226 A1 | 10/2010 |
| DE | 102009002227 A1 | 10/2010 |
| DE | 102009002287 A1 | 10/2010 |
| DE | 102009017612 A1 | 10/2010 |
| DE | 102009026414 A1 | 11/2010 |
| DE | 102009027024 A1 | 12/2010 |
| DE | 102009029813 A1 | 12/2010 |
| DE | 102010027180 A1 | 5/2011 |
| DE | 102010028418 A1 | 11/2011 |
| DE | 102010063585 A1 | 6/2012 |
| DE | 102011084904 A1 | 6/2012 |
| DE | 102011087999 A1 | 9/2012 |
| DE | 102012222967 A1 | 9/2013 |
| DE | 102012222764 A1 | 10/2013 |
| EP | 2266529 A2 | 12/2010 |
| EP | 2514403 A1 | 10/2012 |
| EP | 2740484 A1 | 6/2014 |
| EP | 2792684 A1 | 10/2014 |
| FR | 2668365 A1 | 4/1992 |
| RU | 2591789 C1 | 7/2016 |
| WO | WO-9910374 A1 | 3/1999 |
| WO | WO-2005016364 A1 | 2/2005 |
| WO | WO-2005048968 A1 | 6/2005 |
| WO | WO-2006131234 A1 | 12/2006 |
| WO | WO-2007000214 A1 | 1/2007 |
| WO | WO-2007017196 A2 | 2/2007 |
| WO | WO-2007059822 A1 | 5/2007 |
| WO | WO-2007078056 A1 | 7/2007 |
| WO | WO-2008003685 A1 | 1/2008 |
| WO | WO-2008058943 A2 | 5/2008 |
| WO | WO-2008065072 A1 | 6/2008 |
| WO | WO-2008090226 A2 | 7/2008 |
| WO | WO-2008155382 A2 | 12/2008 |
| WO | WO-2008155391 A2 | 12/2008 |
| WO | WO-2009026949 A1 | 3/2009 |
| WO | WO-2009059205 A1 | 5/2009 |
| WO | WO-2009114959 A1 | 9/2009 |
| WO | WO-2010019939 A1 | 2/2010 |

(56) References Cited

FOREIGN PATENT DOCUMENTS

| WO | WO-2010037553 A1 | 4/2010 |
|---|---|---|
| WO | WO-2010049011 A2 | 5/2010 |
| WO | WO-2010049389 A1 | 5/2010 |
| WO | WO-2010049390 A1 | 5/2010 |
| WO | WO-2010049457 A2 | 5/2010 |
| WO | WO-2010118880 A1 | 10/2010 |
| WO | WO-2011028673 A2 | 3/2011 |
| WO | WO-2012010684 A2 | 1/2012 |
| WO | WO-2012010685 A2 | 1/2012 |
| WO | WO-2012044745 A2 | 4/2012 |
| WO | WO-2012130775 A1 | 10/2012 |
| WO | WO-2012143845 A2 | 10/2012 |
| WO | WO-2012164488 A2 | 12/2012 |
| WO | WO-2013060707 A2 | 5/2013 |
| WO | WO-2013075017 A1 | 5/2013 |
| WO | WO-2013091975 A1 | 6/2013 |
| WO | WO-2013092080 A1 | 6/2013 |
| WO | WO-2014081845 A2 | 5/2014 |
| WO | WO-2014090524 A2 | 6/2014 |
| WO | WO-2014110613 A1 | 7/2014 |
| WO | WO-2014120793 A1 | 8/2014 |
| WO | WO-2014140890 A2 | 9/2014 |
| WO | WO-2016007314 A1 | 1/2016 |
| WO | WO-2016046848 A2 | 3/2016 |
| WO | WO-2016097966 A1 | 6/2016 |
| WO | WO-2017001625 A1 | 1/2017 |
| WO | WO-2017136600 A1 | 8/2017 |
| WO | WO-2017216177 A1 | 12/2017 |
| WO | WO-2019028275 A1 | 2/2019 |

OTHER PUBLICATIONS

Widgerow A. et al. Extracellular Matrix Modulation: Optimizing Skin Care and Rejuvenation Procedures. Supplement to J of Drugs in Dermatology 15(4 Suppl)s62-s71 Apr. 2016. (Year: 2016).*
Widgerow A. Topical Skin Restoration Technology. Insert to Modern Aesthetics May 1-8/Jun. 2016 (Year: 2016).*
Active Concepts. AC Dermal Respiratory Factor Advanced PF. Technical Data Sheet. (4 pgs.) (2014).
Alkemade et al. SKALP/elafin is an inducible proteinase inhibitor in human epidermal keratinocytes. Journal of Cell Science 107:2335-2342 (1994).
Al-Rimawi et al. Formulation and evaluation of a moisturizing day cream containing olive leaves extract. Int J Devel Res 4(10):1996-2000 (2014).
Ashcroft et al. Age-Related Changes in the Temporal and Spatial Distributions of Fibrillin and Elastin Mrnas and Proteins in Acute Cutaneous Wounds of Healthy Humans. Journal of Pathology 183:80-89 (1997).
Bani et al. Histological and Ultrastructural Effects of Ultrasound-induced Cavitation on Human Skin Adipose Tissue. Plast Reconstr Surg Glob Open 1(6):e41 (2013).
Bekker et al. Relating rheological measurements to primary and secondary skin feeling when mineral-based and Fischer-Tropsch wax-based cosmetic emulsions and jellies are applied to the skin. Int J Cosmet Sci 35(4):354-361 (2013).
Bitto et al. Long-term IGF-I exposure decreases autophagy and cell viability. PLoS One 5(9):e12592 (2010).
Blanchevoye et al. Interaction between the Elastin Peptide VGVAPG and Human Elastin Binding Protein. J Biol Chem 288:1317-1328 (2012).
Brandner et al. Caffeine improves barrier function in male skin. International Journal of Cosmetic Science 28:343-347 (2006).
Bylka et al. Centella asiatica in cosmetology. Postepy Dermatol Alergol 30(1):46-49 (2013).
Cappellano et al. Dermal white adipose tissue renewal is regulated by the PDGFA/AKT axis. Stem Cell Investig 4:23 (2017).
CELLDETOX® Product brochure. Silab (3 pgs.) (2013).
Cenizo et al. LOXL as a target to increase the elastin content in adult skin: a dill extract induces the LOXL gene expression. Experimental Dermatology 15:574-581 (2006).

Chiang et al. Current concepts related to hypertrophic scarring in burn injuries. Wound Repair Regen 24(3):466-77 (2016).
Cho et al. Phosphatidylserine prevents UV-induced decrease of type I procollagen and increase of MMP-1 in dermal fibroblasts and human skin in vivo. J Lipid Res 49(6):1235-1245 (2008).
Cianfanelli et al. Ambra1 at a glance. J Cell Sci 128(11):2003-8 (2015).
Codogno et al. Atg5: more than an autophagy factor. Nature Cell Biology 8(10):1045-1048 (2006).
De Backer et al. Controlling MicroRNAs to Fight Skin Senescence. Cosmetics & Toiletries Available at https://www.cosmeticsandtoiletries.com/research/biology/Controlling-MicroRNAs-to-Fight-Skin-Senescence-367698261.html (Feb. 4, 2016) (6 pgs.).
Donati et al. Epidermal Wnt/β-catenin signaling regulates adipocyte differentiation via secretion of adipogenic factors. PNAS USA 111(15):E1501-E1509. (2014).
Dow Corning 9040 Silicone Elastomer Blend product Information (7 pgs) (Apr. 3, 2012).
Draelos et al. Glycation and Skin Aging: A Review. Cosmetics & Toiletries Magazine (3 pgs.) (Jun. 2011).
Driskell et al. Defining dermal adipose tissue. Exp Dermatol 23(9):629-631 (2014).
Duncan et al. A prospective study analyzing the application of radiofrequency energy and high-voltage, ultrashort pulse duration electrical fields on the quantitative reduction of adipose tissue. J Cosmet Laser Ther 18(5):257-67 (2016).
Emami-Razavi et al. Effect of Bentonite on Skin Wound Healing: Experimental Study in the Rat Model. Acta Medica Iranica 44(4):235-240 (2006).
Essenskin™ The essential by instinct. Brochure (2 pgs.) (2008).
Floquet et al. Structural Characterization of VGVAPG an Elastin-Derived Peptide. Biolpolymers 76:266-280 (2004).
Garibyan et al. Three-dimensional volumetric quantification of fat loss following cryolipolysis. Lasers Surg Med 46(2):75-80 (2014).
Grant et al. Fat in flames: influence of cytokines and pattern recognition receptors on adipocyte lipolysis. Am J Physiol Endocrinol Metab 309(3):E205-13 (2015).
Gregory et al. The macrophage and the apoptotic cell: an innate immune interaction viewed simplistically? Immunology 113:1-14 (2004).
Hakozaki et al. The effect of niacinamide on reducing cutaneous pigmentation and suppression of melanosome transfer. Br J Dermatol 147:20-31 (2002).
He et al. Receptor for advanced glycation end products binds to phosphatidylserine and assists in the clearance of apoptotic cells. EMBO Reports 12(4):358-364 (2011).
Hocker et al. Inhibition of autophagy through MAPK14-mediated phosphorylation of ATG5. Autophagy 9(3):426-428 (2013).
Ingargiola et al. Cryolipolysis for fat reduction and body contouring: safety and efficacy of current treatment paradigms. Plast Reconstr Surg 135(6):1581-90 (2015).
Ito et al. Is the Hair Follicle Necessary for Norm Wound Healing. J Invest Dermatol 128:1059-1061 (2008).
Jalian et al. Paradoxical adipose hyperplasia after cryolipolysis. JAMA Dermatol 150(3):317-9 (2014).
Johnson et al. Controlled delivery of heparin-binding EGF-like growth factor yields fast and comprehensive wound healing. J Control Release 166(2):124-129 (2013).
Katsiki et al. The olive constituent oleuropein exhibits proteasome stimulatory properties in vitro and confers life span extension of human embryonic fibroblasts. Rejuvenation Res 10(2):157-172 (2007).
Khamlue et al. Skin Wound Healing Promoting Effect of Polysaccharides Extracts from Tremella fuciformis and Auricularia auricula on the ex-vivo Porcine Skin Wound Healing Model. 2012 4th International Conference on Chemical, Biological and Environmental Engineering IPCBEE 43:93-98 (2012).
Kilmer et al. Safety and efficacy of cryolipolysis for non-invasive reduction of submental fat. Lasers Surg Med 48(1):3-13 (2016).
Kontogianni et al. Olive leaf extracts are a natural source of advanced glycation end product inhibitors. J Med Food 16(9):817-822 (2013).

(56) References Cited

OTHER PUBLICATIONS

Koo et al. Protection from photodamage by topical application of caffeine after ultraviolet irradiation. Br J Dermatol 156(5):957-964 (2007).
Kovac et al. Plantago lanceolata L. water extract induces transition of fibroblasts into myofibroblasts and increases tensile strength of healing skin wounds. J Pharm Pharmacol 67(1):117-125 (2015).
Kruglikov et al. Skin aging: are adipocytes the next target? Aging (Albany NY) 8(7):1457-1469 (2016).
Laatikainen et al. SOD3 decreases ischemic injury derived apoptosis through phosphorylation of Erk1/2, Akt, and FoxO3a. PLoS One 6(8):e24456 (2011).
Lee et al. Protective effect and mechanism of phosphatidylserine in UVB-induced human dermal fibroblasts. EU J Lipid Sci Technol 115(7):783-790 (2013).
Li et al. Antioxidant and anti-inflammatory activities of methanol extracts of Tremella fuciformis and its major phenolic acids. J Food Sci 79(4):C460-468 (2014).
Liao et al. Antioxidative activity, moisture retention, film formation, and viscosity stability of Auricularia fuscosuccinea, white strain water extract. Biosci Biotechnol Biochem 78(6):1029-1036 (2014).
Liu et al. Elastic fiber homeostasis requires lysyl oxidase-like 1 protein. Nat Genet. 36(2):178-182 (2004).
Luebberding et al. Age-related changes in skin barrier function—quantitative evaluation of 150 female subjects. Int J Cosmet Sci. 35(2):183-190 (2013).
Mahmoudi et al. Comparing the effects of Bentonite & Calendula on the improvement of infantile diaper dermatitis: A randomized controlled trial. Indian J Med Res 42:742-746 (2015).
Maixner et al. Autophagy in Adipose Tissue. Obes Facts. 5(5):710-721 (2012).
Manstein et al. Selective cryolysis: A novel method of non-invasive fat removal. Lasers in Surgery and Medicine 40(9):595-604 (2008).
Marino et al. Human autophagins, a family of cysteine proteinases potentially implicated in cell degradation by autophagy. J Biol Chem 278(6):3671-8 (2003).
Nagase Chemtex PIPS; Phosphatidylserine & phosphatidylinositol (4 pgs) (May 2015).
Navarrete-Solis et al. A Double-Blind, Randomized Clinical Trial of Niacinamide 4% versus Hydroquinone 4% in the Treatment of Melasma. Dermatol Res Pract 2011:379173 (2011).
Noblesse et al. Lysyl oxidase-like and lysyl oxidase are present in the dermis and epidermis of a skin equivalent and in human skin and are associated to elastic fibers. J Invest Dermatol 122(3):621-630 (2004).
Ojima et al. Dynamics of protein secretion during adipocyte differentiation. FEBS Open Bio 6(8):816-26 (2016).
Omar. Oleuropein in olive and its pharmacologic effects. Sci Pharm 78(2):133-154 (2010).
Pereira et al. The role of inflammation in adipocytolytic nonsurgical esthetic procedures for body contouring. Clinical, Cosmetic and Investigational Dermatology 10:57-66 (2017).
Phytosonic™ Brochure. Sederma (2 pgs.) (Sep. 2008).
Pickart et al. The Human Tripeptide GHKCU in Prevention of Oxidative Stress and Degenerative Conditions of Aging: Implications for Cognitive Health. Oxid Med Cell Longev 2012:324832 (2012).
Pickart. The human tri-peptide GHK and tissue remodeling. J Biomater Sci Polym Ed 19:969-988 (2008).
Plikus et al. Regeneration of fat cells from myofibroblasts during wound healing. Science 355(6326):748-752 (2017).
Pro-Lipo™ Neo. Smart Lipsome Preparation. LucasMeyer Cosmetics PowerPoint Presentation (25 pgs) (viewed Aug. 2018).
Rigacci et al. Oleuropein aglycone induces autophagy via the AMPK/mTOR signalling pathway: a mechanistic insight. Oncotarget 6(3):35344-35357 (2015).
Rivera-Gonzalez et al. Skin Adipocyte Stem Cell Self-Renewal is Regulated by a PDGFA/AKT-Signaling Axis. Cell Stem Cell 19(6):738-751 (2016).
Rnjak et al. Severe Burn Injuries and the Role of Elastin in the Design of Dermal Substitutes. Tissue Eng Part B Rev 17(2):81-91 (2011).
Russell et al. Studies on the antiobesity effect of zinc-alpha2-glycoprotein in the ob/ob mouse. Int J Obes (Lond) 35(3):345-354 (2011).
Seaman et al. Paradoxical Adipose Hyperplasia and Cellular Effects After Cryolipolysis: A Case Report. Aesthet Surg J 36(1):NP6-13 (2016).
Senior et al. Val-Gly-Val-Ala-Pro-Gly, a repeating peptide in elastin, is chemotactic for fibroblasts and monocytes. J Cell Biol 99:870-874 (1984).
Shadfar et al. Anatomy and Physiology of the Aging Neck. Facial Plast Surg Clin North Am. 22(2):161-170 (2014).
Shirakata et al. Heparin-binding EGF-like growth factor accelerates keratinocyte migration and skin wound healing. J Cell Sci 118(Pt 11):2363-2370 (2005).
Singh et al. Lipophagy: Connecting Autophagy and Lipid Metabolism. Int J Cell Biol. 2012:282041 (2012).
Skaltsounisd et al. Redox Biol. Aug. 2015;5:20515. doi: 10.1016j.redox.2015.04.010 (13 pgs.) (Epub Apr. 29, 2015).
Sklirou et al. Hexapeptide-11 is a novel modulator of the proteostasis network in human diploid fibroblasts. Redox Biology 5:205-215 (2015).
SymDecanox Ha. New Generation of Antioxidant. Symris Brochure (34 pgs) (2015).
Takeuchi et al. Inhibition of platelet-derived growth factor signalling induces autophagy in malignant glioma cells. Br J Cancer 90(5):1069-75 (2004).
Tsai et al. How irritant is water? An overview. Contact Dermatitis 41(6):311-314 (1999).
Uplevity™. Lipotec. Technical Report (25 pgs) (Jun. 2013).
Van Zutphen et al. Lipid droplet autophagy in the yeast Saccharomyces cerevisiae. Mol Biol Cell 25(2):290-301 (2014).
Verma et al. Transfollicular drug delivery: current perspectives. Research and Reports in Transdermal Drug Delivery 5:1-17 (2016).
Verma. Particle size of liposomes influences dermal delivery of substances into skin. International Journal of Pharmaceutics 258(1-2):141-151 (2003).
Vilchez et al. Marine carotenoids: biological functions and commercial applications. Mar Drugs 9(3):319-333 (2011).
Vogt et al. 40 nm, but not 750 or 1,500 nm, nanoparticles enter epidermal CD1a+ cells after transcutaneous application on human skin. J Invest Dermatol 126(6):1316-22 (2006).
Vural et al. Autophagy in macrophages: impacting inflammation and bacterial infection. Scientifica (Cairo) 2014:825463 (2014).
Wang. Lipid droplets, lipophagy, and beyond. Biochim Biophys Acta 1861(8 Pt B):793-805 (2016).
Wen et al. Xylose phosphorylation functions as a molecular switch to regulate proteoglycan biosynthesis. PNAS USA 111(44):15723-15728 (2014).
Widgerow et al. Extracellular Matrix Modulation: Optimizing Skin Care and Rejuvenation Procedures. J Drugs Dermatol 15(45):S63-S71 (2016).
Widgerow. Topical Skin Restoration Technology—Advances in Age Management Strategies. Modern Aesthetics (8 pgs.) (May/Jun. 2016).
Wohlrab et al. Niacinamide—Mechanisms of Action and Its Topical Use in Dermatology. Skin Pharmacol Physiol 27:311-315 (2014).
Wu et al. Caspases: a molecular switch node in the crosstalk between autophagy and apoptosis. Int J Biol Sci 10(9):1072-83 (2014).
Zhang et al. Induction of autophagy is essential for monocyte-macrophage differentiation. Blood 119(12):2895-2905 (2012).
Zoumalan. Topical Agents for Scar management: Are They Effective? J Drugs Dermatol 17(4):421-425 (Apr. 2018).
Carruthers et al. Cryolipolysis and skin tightening. Dermatol Surg 40(Suppl. 12):S184-S189 (2014).
Park et al. High-Intensity Focused Ultrasound for the Treatment of Wrinkles and Skin Laxity in Seven Different Facial Areas. Ann Dermatol 27(6):688-693 (2015).
PCT/US2018/045045 International Search Report and Written Opinion dated Oct. 10, 2018.

(56) References Cited

OTHER PUBLICATIONS

Bauters et al. Gelatinase A (MMP2) promotes marine adipogenesis. Biochimica et Biophysica Acta (BBA) General Subjects 1850:1449-1456 (2015).

'BioBustyl: A genuine firmness and tone concentrate for the bust' Sederma Brochure (7 pgs.) (Feb. 2008).

EWC's Skin Deep Cosmetics Database 'System JO Maximizer Shaping Cream' Nov. 2014 Retrieved from the internet:< URL: http:www.ewg.orgskindeepproduct526533System_JO_Maximizer_Shaping_Cream> (5 pgs).

Fligiel et al. Collagen degradation in aged/photodamaged skin in vivo and after exposure to matrix metalloproteinase-1 in vitro. J Invest Dermatol 120:842-848 (2003).

Gruber et al. Modulation of cellular senescence in fibroblasts and dermal papillae cells in vitro. J Cosmet Sci. 64(2):79-87 (2013) (Abstract).

Jose et al. Enhanced trophic factor secretion by mesenchymal stem/stromal cells with Glycine-Histidine-Lysine (GHK)-modified alginate hydrogels. Acta Biomater 10(5):1955-1964 (2014).

Lupo et al. Cosmeceutical peptides. Dermatol Ther 20:343-349 (2007).

PCT/US2017/016292 International Search Report and Written Opinion dated May 12, 2017.

Preissig et al. Current laser resurfacing technologies: A review that delves beneath the surface. Semin Plast Surg 26(3):109-116 (2012).

Resh. Fatty acylation of proteins: new insights into membrane targeting of myristoylated and palmitoylated proteins. Biochimica et Biophysica Acta 1451:1-16 (1999).

Simeon et al. Expression and activation of matrix metalloproteinases in wounds: modulation by the tripeptide-copper complex glycyl-L-histidyl-L-lysine-Cu2+. J Invest Dermatol 112:957-962 (1999).

Simons. Angiogenesis: where do we stand now? Circulation 111(12):1556-1566 (2005).

Unisooth PN47. Induchem Switzerland. (15 pgs) (Sep. 21, 2010).

U.S. Appl. No. 15/423,530 1st Action Interview dated Sep. 6, 2017.

U.S. Appl. No. 15/423,530 Office Action dated Dec. 18, 2017.

U.S. Appl. No. 15/423,530 PreInterview Action dated May 25, 2017.

U.S. Appl. No. 16/004,259 Office Action dated Sep. 26, 2018.

U.S. Appl. No. 16/053,674 Preinterview Office Action dated Jan. 25, 2019.

Widgerow. Chronic wound fluid-thinking outside the box. Wound Repair Regen 19(3):287-291 (2011).

Casas. 2019 ASAPS—Examination of healing and recovery outcomes post cosmetic surgery and non-surgical body contouring procedures with a novel topical body treatment incorporating Tripeptide and Hexapeptide (TriHex) technology. Abstract 2019.

Widgerow et al. A Double-Blind Randomized controlled Trial Evaluation the Efficacy and Tolerability of a Topical body Treatment in Combination With Cryolipolysis Procedures. J Drugs Dermatol 18(4):342-348 (2019).

Widgerow et al. Non-Surgical Fat Reduction and Topical Modulation of Adipose Tissue Physiology. J Drugs Dermatol 18(4):375-380 (2019).

Widgerow et al. Preoperative Skin Conditioning: Extracellular Matrix Clearance and Skin Bed Preparation, A New Paradigm. Aesthetic Surgery Journal 39(53):S103-S111 (2019).

\* cited by examiner

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gln Pro Arg
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Thr Phe Lys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gln Thr Arg
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Arg Lys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Lys Asp Val Tyr
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Thr Thr Lys Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 7

Tyr Gly Gly Phe Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Leu Ala Ala Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Gly Val Ala Pro Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Lys Thr Thr Lys Ser
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Val Ala Pro Phe Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gly Tyr Tyr Leu Leu Glu
1               5
```

PEPTIDE COMPOSITIONS AND METHODS FOR AMELIORATING SKIN LAXITY AND BODY CONTOUR

CROSS-REFERENCE

This application claims the benefit of U.S. Provisional Patent Application No. 62/696,256 filed on Jul. 10, 2018; U.S. Provisional Patent Application No. 62/541,036 filed on Aug. 3, 2017; and U.S. Provisional Patent Application No. 62/541,022 filed on Aug. 3, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 1, 2018, is named 53936-702_201_SL.txt and is 2,745 bytes in size.

FIELD OF THE DISCLOSURE

Compositions and methods for amelioration of skin laxity are provided.

BACKGROUND OF THE DISCLOSURE

Traditional and conventional skincare treatments for alleviating these negative side effects have primarily relied upon a variety of common over the counter remedies. The need for treatments effective at ameliorating skin laxity associated with body shaping and contouring procedures is also rapidly growing.

SUMMARY

Compositions and methods for ameliorating skin laxity associated with body sculpting procedures are provided herein. These compositions preferably comprise two different peptides: a dipeptide, tripeptide, or tetrapeptide in combination with a pentapeptide, hexapeptide or heptapeptide. Methods are also provided for producing and using the compositions.

An aspect described herein is a topical composition for improving skin laxity or body contouring, comprising: one or more tripeptides, one or more tetrapeptides, and one or more hexapeptides, wherein the topical composition improves skin laxity or body contouring. In one feature, a tripeptide of the one or more tripeptides is present at 1-10 ppm. In one feature, a tripeptide of the one or more tripeptides is tripeptide-1. In one feature, the tripeptide-1 comprises palmitoyl tripeptide-1, myristoyl tripeptide-1, or a combination thereof. In one feature, a tetrapeptide of the one or more tetrapeptides is present at 1-10 ppm. In one feature, a tetrapeptide of the one or more tetrapeptides is tetrapeptide-2. In one feature, the tetrapeptide-2 comprises acetyl tetrapeptide-2. In one feature, wherein a first hexapeptide of the one or more hexapeptides is present at 0.5-10 ppm. In one feature, a first hexapeptide of the one or more hexapeptides is hexapeptide-12. In one feature, the hexapeptide-12 comprises palmitoyl hexapeptide-12, myristoyl hexapeptide-12, or a combination thereof. In one feature, a second hexapeptide of the one or more hexapeptides comprises a different amino acid sequence. In one feature, the second hexapeptide is present at 0.001-1 ppm. In one feature, the second hexapeptide is hexapeptide-11. In one feature, the second hexapeptide is formulated in a liposome. In one feature, the topical composition further comprises ceramide NP, *Tremella fuciformis* extract, niacinamide, hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof.

An aspect described herein is a method for improving skin laxity or body contouring, comprising: administering a topical composition comprising one or more tripeptides, one or more tetrapeptides, and one or more hexapeptides, wherein the topical composition improves skin laxity or body contouring. In one feature, the topical composition is administered in conjunction with a body-shaping procedure. In one feature, the topical composition is administered following a body-shaping procedure. In one feature, the topical composition is administered up to one day following a body-shaping procedure. In one feature, the body-shaping procedure comprises high frequency focused ultrasound, pulsed focus ultrasound, cryolipolysis, radiofrequency induced electroporation, injectable lipolytic agents, liposuction, or combinations thereof. In one feature, the topical composition is administered in conjunction with a skin-laxity procedure. In one feature, the topical composition is administered following a skin-laxity procedure. In one feature, the topical composition is administered up to one day following a skin-laxity procedure. In one feature, the skin-laxity procedure comprises high frequency focused ultrasound, pulsed focus ultrasound, radiofrequency induced electroporation, or combinations thereof. In one feature, the topical composition is administered in conjunction with a non-invasive fat reduction procedure. In one feature, the topical composition is administered following a non-invasive fat reduction procedure. In one feature, the non-invasive fat reduction procedure comprises low level laser therapy, infrared light, ultrasound, radiofrequency, cryolipolysis, or combinations thereof. In one feature, the topical composition is administered one, two three, four, five, or six times a day. In one feature, the topical composition is administered two times a day. In one feature, the topical composition is administered for at least one week, 2 weeks, 4 weeks, 8 weeks, or 12 weeks. In one feature, a tripeptide of the one or more tripeptides is present at 1-10 ppm. In one feature, a tripeptide of the one or more tripeptides is tripeptide-1. In one feature, the tripeptide-1 comprises palmitoyl tripeptide-1, myristoyl tripeptide-1, or a combination thereof. In one feature, a tetrapeptide of the one or more tetrapeptides is present at 1-10 ppm. In one feature, a tetrapeptide of the one or more tetrapeptides is tetrapeptide-2. In one feature, the tetrapeptide-2 comprises acetyl tetrapeptide-2. In one feature, a first hexapeptide of the one or more hexapeptides is present at 0.5-10 ppm. In one feature, a first hexapeptide of the one or more hexapeptides hexapeptide is hexapeptide-12. In one feature, the hexapeptide-12 comprises palmitoyl hexapeptide-12, myristoyl hexapeptide-12, or a combination thereof. In one feature, a second hexapeptide of the one or more hexapeptides comprises a different amino acid sequence. In one feature, the second hexapeptide is present at 0.001-1 ppm. In one feature, the second hexapeptide is hexapeptide-11. In one feature, the second hexapeptide is formulated in a liposome. In one feature, the topical composition further comprises ceramide NP, *Tremella fuciformis* extract, niacinamide, hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof.

Any of the features of an embodiment of any of the aspects is applicable to all other aspects and embodiments identified herein. Moreover, any of the features of an embodiment of any of the aspects is independently combinable, partly or wholly with other embodiments described herein in any way, e.g., one, two, or three or more embodiments may be combinable in whole or in part. Further, any of the features of an embodiment of any of the aspects may be made optional to other aspects or embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
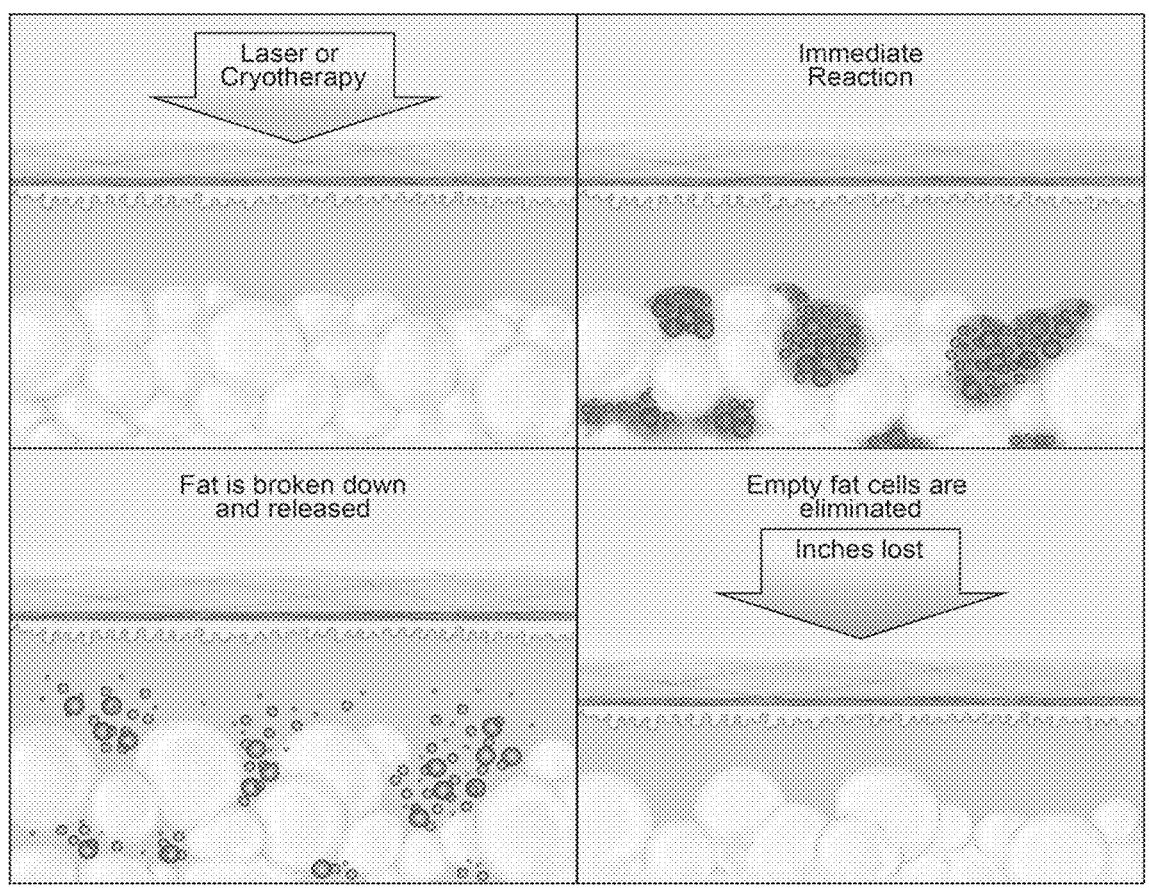
FIG. 1 illustrates a schematic of the mechanism of action for non-invasive fat reduction.
Figure 2:
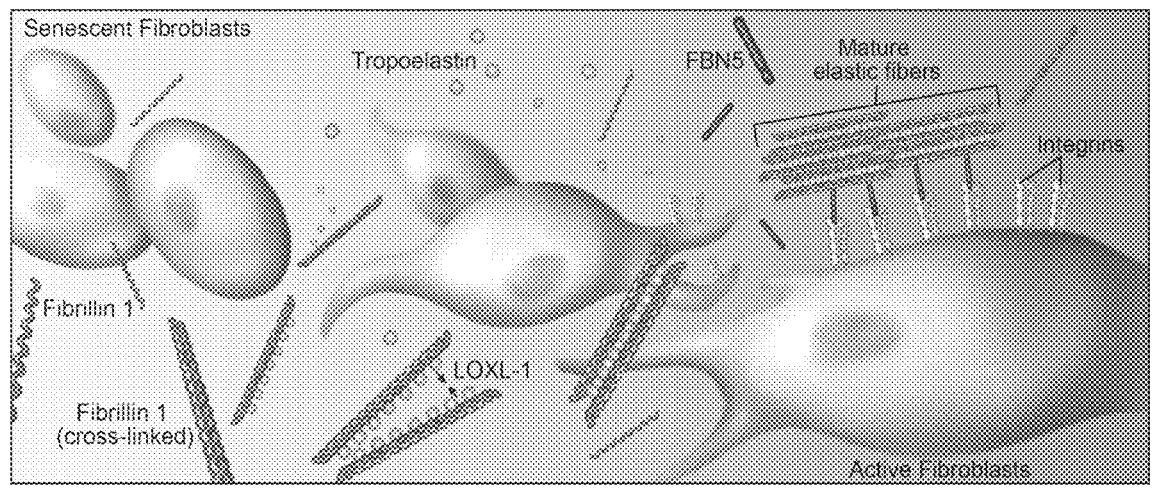
FIG. 2 illustrates a schematic of elastin stimulation where formulations described herein result in an increase in production of elastin components and cross-linkages of the elastin components.

The following description and examples illustrate a preferred embodiment of the present disclosure in detail. Those of skill in the art will recognize that there are numerous variations and modifications of this disclosure that are encompassed by its scope. Accordingly, the description of a preferred embodiment should not be deemed to limit the scope of the present disclosure.

Definitions

The terms "pharmaceutically acceptable salts" and "a pharmaceutically acceptable salt thereof" as used herein are broad terms, and are to be given their ordinary and customary meaning to a person of ordinary skill in the art (and are not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of phosphate groups are intended to be included. Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Overview

Skin laxity is a natural progressive phenomenon associated with aging. Minimally invasive tightening procedures directed at subdermal tissues or directly at superficial layers of the skin have increased dramatically in the last few years. In addition, other devices targeting deeper fatty tissue may result in relative skin laxity.

In addition, many of these non-invasive/semi-invasive procedures aimed at denaturing and breaking down fatty tissue, leave residual fragments of proteins, cells and debris within the extra cellular matrix (ECM) and intracellularly. In addition, released free fatty acids can be cytotoxic to surrounding cells. These fragments may delay healing and regeneration and would benefit from an efficient recycling program in the form of autophagy and intracellular proteasome activity.

Thus, overall body shaping techniques can benefit greatly from a topical skin application that could complement the skin tightening procedures stimulating neocollagenesis and neoelastogenesis, aid in eliminating post-surgical and non-surgical fragmentation and provide relief from procedural side-effects. In addition, tightening of the relatively lax skin that remains following certain procedures, would be of great benefit.

At a microscopic level, aging skin laxity appears to be related to disorderly dysfunctional collagen and elastin, inefficient senescent fibroblasts with decreased production of collagen and elastin, and decreased glycosaminoglycans in the dermal layer.

Many of the current devices utilized for the indications described above use non-invasive radiofrequency (RF)-based technology (hot) or cryo-based technologies (cold). RF technology involves electric energy rather than photo-energy, often utilizing skin sparing techniques or insulated needles where these are utilized and thus the epidermis is largely unaffected and untargeted in these situations. Topical formulations which tighten skin would be major complementary adjuncts to such procedures enhancing the overall outcome.

Furthermore, non-invasive fat elimination devices based on 'cold' or 'hot' technologies rely on long term apoptosis of adipocytes with gradual absorption and digestion of lipid droplets and fat cellular components. These lipid fragments may consist of free fatty acids and cellular organelles, some of which may be toxic to surrounding cellular tissue. In addition, it is possible that these fragments initiate regeneration of fat in a certain proportion of patients resulting in a condition known as 'Paradoxical adipose hyperplasia'. Promotion of accelerated digestion of these fragments is thus advantageous. Autophagy is a process of self-degradation of cellular components activated in response to cellular stress. It is important not only for balancing energy sources in development or in response to cellular stress but also for removing misfolded/aggregated proteins, damaged organelles and pathogens. The formulations described herein are useful for accelerating or enhancing the lipolysis process.

Thus a formulation of ingredients that provides for accelerated digestion of cellular fragments, stimulates elastin, collagen and glycosaminoglycan synthesis, and provides symptomatic relief from swelling and painful subcutaneous scar tissue, would be a desirable partner for non-invasive body contouring devices.

Formulations

The formulation includes components selected to provide activity in selected areas.

Stimulation of autophagy, accelerated digestion of cellular fragments, reverse cellular senescence (wake up sleeping dormant fibroblasts to produce new collagen and elastin and build ECM), thereby improving tone and texture of skin Hexapeptide-11 is a potent stimulator of autophagy, promotes dose and time-dependent activation of proteasome, autophagy, chaperones and antioxidant responses related genes. Hydrolyzed *Candida saitoana* extract stimulates autophagy, favors formation of lysosomes, purified α-glucan active ingredient, detoxifies cells by removing altered cell components (oxidized proteins and peroxidized lipids) and blocks the accumulation of lipofuscin aggregates. *Plantago lanceolata*, also called "Plantain," is involved in microRNAs inhibition, restarts the protein synthesis in order to prevent cellular senescence and extracellular matrix breakdown. Oleuropein is anti-inflammatory but also stimulates UPS system and autophagy digesting worn out proteins in the cells, reversing cellular senescence.

With respect to hexapeptide-11, age-related gradual accumulation or device related sudden accumulation of damaged biomolecules (including proteins) can compromise cellular homeodynamics as they result in failure of most cellular maintenance pathways. To maintain proteostasis (protein balance) cells have developed a modular, yet integrated system which ensures general proteome quality control and it is called the proteostasis network (PN). See, e.g., Sklirou A D, Ralli M, Dominguez M, Papassideri I, Skaltsounis A L, Trougakos I P. Hexapeptide-11 is a novel modulator of the proteostasis network in human diploid fibroblasts. *Redox Biol* 2015; 5: 205-15. This responds to conditions of proteotoxic stress by rescuing or degrading unfolded, misfolded or non-native polypeptides. Central to the PN functionality are the two main proteolytic systems namely the autophagy lysosome (ALS) and the ubiquitin-proteasome (UPS) systems. Hexapeptide-11 promotes activation of proteasome, autophagy, chaperones and antioxidant responses related genes. This stimulation of autophagy is also important in the transformation of monocytes to macrophages enabling engulfment digestion of extracellular fragments. See, e.g., Zhang Y, Morgan M J, Chen K, Choksi S, Liu Z G. Induction of autophagy is essential for monocyte-macrophage differentiation. *Blood* 2012; 119(12): 2895-905. Moreover, it confers significant cellular protection against oxidative-stress-mediated premature cellular senescence. Finally, Hexapeptide-11 was found to induce the activity of extracellular MMP 2 and it also suppressed cell migration. These findings indicate that Hexapeptide-11 is a promising anti-ageing agent and a potent inducer of cellular fragment digestion.

In some embodiments, compositions described herein comprise hexapeptide-11. In some embodiments, compositions described herein, upon administering to a skin region of interest, induces an increase in expression of AMBRA1, ATG4A, PSMB5, CASP3, ATG5, or a combination thereof in the skin region. In some embodiments, compositions described herein, upon administering to a skin region of interest, induces an increase in expression of AMBRA1, ATG4A, PSMB5, CASP3, ATG5, or a combination thereof in the skin region by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, compositions described herein, upon administering to a skin region of interest, induces an increase in expression of AMBRA1, ATG4A, PSMB5, CASP3, ATG5, or a combination thereof in the skin region by at least or about 0.5-fold, 1.0-fold, 1.5-fold, 2.0-fold, 2.5-fold, 3.0-fold, 3.5-fold, 4.0-fold, 5.0-fold, 6.0-fold, 7.0-fold, 8.0-fold, 9.0-fold, 10-fold, or more than 10-fold. In some embodiments, compositions described herein, upon administering to a skin region of interest, induces a decrease in expression of COL5A2, MAPK14, TNF, SOD3, PDGFRA, IGF1, or a combination thereof in the skin region. In some embodiments, compositions described herein, upon administering to a skin region of interest, induces a decrease in expression of COL5A2, MAPK14, TNF, SOD3, PDGFRA, IGF1, or a combination thereof in the skin region by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, compositions described herein, upon administering to a skin region of interest, induces a decrease in expression of COL5A2, MAPK14, TNF, SOD3, PDGFRA, IGF1, or a combination thereof in the skin region by at least or about 0.5-fold, 1.0-fold, 1.5-fold, 2.0-fold, 2.5-fold, 3.0-fold, 3.5-fold, 4.0-fold, 5.0-fold, 6.0-fold, 7.0-fold, 8.0-fold, 9.0-fold, 10-fold, or more than 10-fold.

With respect to hydrolyzed *Candida saitoana* extract, in order to maintain their homeostasis, cells eliminate various accumulated and degraded components. Autophagy, which was recently discovered in skin, stands out today as a powerful mechanism, essential for detoxifying cells and guaranteeing their proper functioning, thereby limiting the senescence. This extract is a purified α-glucan active ingredient, which detoxifies cells by removing altered cell components (oxidized proteins and peroxidized lipids) that saturate them and blocks the accumulation of lipofuscin aggregates, a true marker of aging. See Product monograph: Silab 2013.

In some embodiments, formulations as described herein comprise hydrolyzed *Candida saitoana* extract. In some embodiments, the hydrolyzed *Candida saitoana* extract is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hydrolyzed *Candida saitoana* extract is provided in a range of about 0.25% to about 10%, about 0.5% to about 8%, about 0.75% to about 6%, or about 1% to about 4% by weight. In some embodiments, the hydrolyzed *Candida saitoana* extract is provided at about 3.0% by weight.

With respect to *Plantago lanceolata*, it inhibits micro RNA inhibition of fibroblast function, reversing cellular senescence, thus increasing collagen, laminin, elastin and decreasing MMP-1. See Kovac I, Durkac J, Holly M, et al. *Plantago lanceolata* L. water extract induces transition of fibroblasts into myofibroblasts and increases tensile strength of healing skin wounds. *J Pharm Pharmacol* 2015; 67(1): 117-25, and Debacker A, Lavaissière L, Ringenbach C, Mondon P, Dal Toso R. Controlling MicroRNAs to Fight Skin Senescence. *Cosmetics & Toiletries* 2016; Feb. 4, 2016: 1-6. Small endogenous noncoding RNAs named microRNA (miRNA) bind to partially complementary sequences of their target messenger RNA (mRNA) and repress or degrade the mRNA, which cause gene inactivation or gene silencing. It appears that collagen I, Collagen IV and elastin are partially controlled by several microRNAs, and when these microRNAs are limited, it helps to boost collagen and elastin synthesis to improve the quality of the dermis. *Plantago lanceolata* extract was found to reduce the levels of expression of miRNAs controlling the synthesis of collagens and elastin increasing their production and reducing the fibroblast progression toward senescence. Additional in vivo studies demonstrated increased viscoelastic properties with increases in firmness of 30.9% and elasticity of 22.6%, after one month of product application ($p<0.01$) to the skin.

In some embodiments, formulations as described herein comprise *Plantago lanceolata*. In some embodiments, the *Plantago lanceolata* is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Plantago lanceolata* is provided in a range of about 0.25% to about 10%, about 0.5% to about 8%, about 0.75% to about 6%, or about 1% to about 4% by weight. In some embodiments, the *Plantago lanceolata* is provided at about 2.0% by weight.

With respect to oleuropein, it has proven anti-inflammatory effects, enhances proteasome and autophagic activities recycling used intracellular proteins and reversing cellular senescence. See Katsiki M, Chondrogianni N, Chinou I, Rivett A J, Gonos E S. The olive constituent oleuropein exhibits proteasome stimulatory properties in vitro and confers life span extension of human embryonic fibroblasts. *Rejuvenation Res* 2007; 10(2): 157-72, and Rigacci S, Miceli C, Nediani C, et al. Oleuropein aglycone induces autophagy via the AMPK/mTOR signalling pathway: a mechanistic insight. *Oncotarget* 2015; 6(34): 35344-58.

In some embodiments, formulations as described herein comprise oleuropein. In some embodiments, the oleuropein is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the oleuropein is provided in a range of about 0.001% to about 6%, about 0.002% to about 4%, about 0.01% to about 3%, about 0.02% to about 2%, or about 0.01% to about 0.05% by weight. In some embodiments, the oleuropein is provided at about 0.010% by weight. In some embodiments, the oleuropein is provided at about 0.020% by weight. In some embodiments, the oleuropein is provided at about 0.050% by weight.

Increasing Elastin Production and Functionality; Increasing Lipolysis—Tightening and Lipid Digestion Acetyl Tetrapeptide-2 stimulates LOXL1 (Lysyl oxidase like enzyme 1), which cross links elastin components; binds tropoelastin (TE); builds elastin; and increases FBLN5 (Fibulin 5), which binds TE to integrin to fibroblast stimulating fibroblast to produce elastin. Palmitoyl Tripeptide-1 provides collagen and elastin stimulation, ECM recycling, anti-inflammation, and with Palmitoyl Hexapeptide-12, an elastin binding protein, draws in newly produced elastin. Dill extract (*Anethum graveolens* extract) stimulates LOXL reinduction encouraging elastin formation. Avocado extract, shea butter, and bentonite, in some embodiments, provide tightening, elastase inhibition inhibits elastin breakdown and encourages some fat breakdown and turnover; it also aids in stretch mark alleviation.

In some embodiments, avocado extract is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, avocado extract is provided in a range of about 0.01% to about 5%, about 0.02% to about 4%, 0.05% to about 3%, or about 0.1% to about 2% by weight. In some embodiments, shea butter is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, shea butter is provided in a range of about 0.01% to about 5%, about 0.02% to about 4%, 0.05% to about 3%, or about 0.1% to about 2% by weight. In some embodiments, bentonite is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, bentonite is provided in a range of about 0.01% to about 5%, about 0.02% to about 4%, 0.05% to about 3%, or about 0.1% to about 2% by weight. In some embodiments, avocado extract, shea butter, and bentonite are provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, avocado extract, shea butter, and bentonite are provided in a range of about 0.01% to about 5%, about 0.02% to about 4%, 0.05% to about 3%, about 0.1% to about 2%, or about 0.25% to about 2% by weight. In some embodiments, avocado extract, shea butter, and bentonite are provided at about 0.5% by weight. In some embodiments, avocado extract, shea butter, and bentonite are provided at about 1.0% by weight.

With respect to elastin, it is an assembly of microfibrils and tropoelastin (or soluble elastin). Elastin fibers are formed first by the synthesis of fibrillin microfibers which intertwine and then associate with tropoelastin (TE) protein molecules. TE molecules are bound together and cross linked together with fibrillin fibers by lysyl oxidase like enzyme 1 (LOXL1), a key player regulating the assembly of these two elements—this complex is then presented to the fibroblast by Fibulin 5 (FBLN5) which connects the complex to integrins that connect to the fibroblast. See Ashcroft et al., "Age-related changes in temporal and spatial distributions of fibrillin and elastin mRNAs and proteins in acute cutaneous wounds of healthy humans", J. Pathology 1997; 183:80-9, Cenizo V, Andre' V, Reymermier C, Sommer P, Damour O, E. P. LOXL as a target to increase the elastin content in adult skin: a dill extract induces the LOXL gene expression. *Experimental Dermatology* 2006; 15: 574-81, and Noblesse E, Cenizo V, Bouez C, et al. Lysyl oxidase-like and lysyl oxidase are present in the dermis and epidermis of a skin equivalent and in human skin and are associated to elastic fibers. *J Invest Dermatol* 2004; 122(3): 621-30.

With respect to acetyl tetrapeptide-2, it increases FBLN5 and LOXL1 protein levels, thereby increasing elastin synthesis. It also upregulates genes related to Collagen 1 synthesis. In vivo, it has shown to reduce parameters linked to skin flaccidity and dermal disorganization. See Product monograph: Uplevity™ Lipotec. June 2013.

With respect to TriHex (Palmitoyl tripeptide 1 and Palmitoyl hexapeptide 12), it clears the extracellular matrix of aggregated fragmented collagen and elastin and then stimulate increased new collagen and elastin production. See Widgerow A D, Fabi S G, Palestine R F, et al. Extracellular Matrix Modulation: Optimizing Skin Care and Rejuvenation Procedures. *journal of drugs in dermatology* 2016; 15(4s): S63-S71, and Widgerow A. TOPICAL SKIN RESTORATION TECHNOLOGY—ADVANCES IN AGE MANAGEMENT STRATEGIES. *MODERN AESTHETICS* 2016; (May/June): 1-8.

With respect to *Anethum graveolens*/Dill extract, it produces a reinduction of LOXL synthesis. See Cenizo V, Andre' V, Reymermier C, Sommer P, Damour O, E. P. LOXL as a target to increase the elastin content in adult skin: a dill extract induces the LOXL gene expression. *Experimental Dermatology* 2006; 15: 574-81. While microfibrils and soluble elastin continue to be synthesized throughout life, LOXL dramatically decreases from the age of 18.

Increased levels of LOXL in the skin causes the assembly of microfibrils and tropoelastin, leading to improved mechanical properties of the skin. Elastogenesis mainly occurs until the end of the second decade of the life, although the global content of skin elastin can increase after that, the nature of this elastin protein is often suboptimal and dysfunctional. After this period, the elastin gene and fibrillin-1 gene are still active throughout the life although elastogenesis becomes low or inefficient. Therefore, elastin and fibrillin-1 themselves are not really the missing targets to reinduce elastogenesis but LOXL, which declines after the first decades of life, has been shown to stimulate elastogenesis and maintain elastic fibers homeostasis. See Liu X, Zhao Y, Gao J, et al. Elastic fiber homeostasis requires lysyl oxidase-like 1 protein. *Nat Genet* 2004; 36(2): 178-82. Dill extract was shown to increase the expression of LOXL in fibroblasts and in the skin engineering models and to de novo elastogenesis in vivo.

In some embodiments, formulations as described herein comprise dill extract. In some embodiments, the dill extract is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the dill extract is provided in a range of about 0.25% to about 10%, about 0.025% to about 4%, about 0.5% to about 8%, about 0.75% to about 6%, or about 1% to about 4% by weight. In some embodiments, the dill extract is provided at about 1.0% by weight.

With respect to unroasted shea butter extract and avocado seed extract, they are entrapped in an active multi-lamellar mineral clay (bentonite). In adipocytes, lipolysis naturally occurs to generate energy by hydrolysis of stored triglycerides into fatty acids and glycerol which are then easily released from the cells. See Russell S T, Tisdale M J. Studies on the antiobesity effect of zinc-alpha2-glycoprotein in the ob/ob mouse. *Int J Obes (Lond)* 2011; 35(3): 345-54. This biochemical reaction is regulated by cAMP which activates the Hormone Sensitive Lipase (HSL), the enzyme involved in the hydrolysis. Shea butter extract increases the cAMP level through a pathway acting on Zinc alpha-2-Glycoprotein (ZAG). ZAG is a protein secreted by both adipocytes and keratinocytes—it stimulates cAMP, leading to improvement in lipolysis with a caffeine-like efficacy.

Elastase is a serine protease involved in the degradation of elastin fibers which accelerates loss of dermis density and firmness. See Alkemade J, Molhuizen H, Ponec M, et al. SKALP/elafin is an inducible proteinase inhibitor in human epidermal keratinocytes. *Journal of Cell Science* 1994; 107: 2335-42. Avocado seed extract is able to stimulate SKALP (SKin-derived AntiLeukoProteinase), an elastase inhibitor, inhibiting elastase activity and slowing down the dermis degradation providing a firmer skin. Silanols contained in the bentonite are known to regenerate extra cellular matrix (ECM) through increased stimulation of fibroblast growth. Clinical studies have demonstrated that silanols stimulate the production of collagen and elastin fibers leading to remodeling of the dermal fiber architecture and an overall improvement of the skin surface. See Emami-Razavi S, Esmaeili N, Forouzannia S, et al. EFFECT OF BENTONITE ON SKIN WOUND HEALING: EXPERIMENTAL STUDY IN THE RAT MODEL. *Acta Medica Iranica* 2006; 44(4): 235-40, and Mahmoudi M, Adib-Hajbaghery M, Mashaiekhi M. Comparing the effects of Bentonite & Calendula on the improvement of infantile diaper dermatitis: A randomized controlled trial. *The Indian Journal of Medical Research* 2015; 142(6): 742-6.

In some embodiments, formulations as described herein comprise *Euglena gracilis* extract, aqua, caffeine, *Glaucium flavum* leaf extract, or combinations thereof. *Euglena gracilis* extract, aqua, caffeine, and *Glaucium flavum* leaf extract activate lipolysis, promotes unbinding of adipocytes from ECM by stimulating proteases, phosphodiesterases. In some embodiments, these extracts work synergistically to increase lipolysis, stimulate proteases and phosphodiesterase that release adipocytes from the ECM encouraging their breakdown and absorption. See Product monograph: sederma phytosonic September 2008. In some embodiments, caffeine improves skin barrier function and improve photodamage and skin texture. See Brandner J, Behne M, B H, Moll I. Caffeine improves barrier function in male skin. *International Journal of Cosmetic Science* 2006; 28: 343-7 and Koo S W, Hirakawa S, Fujii S, Kawasumi M, Nghiem P. Protection from photodamage by topical application of caffeine after ultraviolet irradiation. *Br J Dermatol* 2007; 156(5): 957-64.

In some embodiments, formulations as described herein comprising *Euglena gracilis* extract, aqua, caffeine, and *Glaucium flavum* leaf extract are provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Euglena gracilis* extract, aqua, caffeine, and *Glaucium flavum* leaf extract are provided in a range of about 0.001% to about 6%, about 0.002% to about 4%, about 0.01% to about 3%, or about 0.02% to about 2% by weight. In some embodiments, the *Euglena gracilis* extract, aqua, caffeine, and *Glaucium flavum* leaf extract are provided at about 0.20% by weight.

Increasing GAGs (Glycosaminoglycans) Such as Hyaluronic Acid (HA)—Smoothing, Improved Texture and Decreased Crepiness Hydroxymethoxyphenyl decanone is a potent intrinsic hyaluronic acid booster, antioxidant and anti-irritant. Polyholosides from flax seeds include xylose, galactose, arabinose, rhamnose; Xylose, the main pentose included here is the first essential constituent of GAGs and consequently regulates their synthesis. Phosphatidylserine, a Lipoid, provides MMP1 control, procollagen increase, stimulates HA production. *Saccharomyces cerevisiae* is a stressed cellular protoplasm yeast extract that improves fibroblast cellular oxygenation and formation of procollagen and stimulates intrinsic HA production.

With respect to hydroxymethoxyphenyl decanone, it is a potent hyaluronic acid booster, antioxidant and anti-irritant. It has been demonstrated to stimulate the dermal AND epidermal hyaluronic acid level by 259% and 198% versus placebo, respectively in ex vivo human skin model. See Product monograph: Symdecanox, Symrise June 2015.

In some embodiments, formulations as described herein comprise hydroxymethoxyphenyl decanone. In some embodiments, the hydroxymethoxyphenyl decanone is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hydroxymethoxyphenyl decanone is provided in a range of about 0.25% to about 10%, about 0.5% to about 8%, about 0.75% to about 6%, about 1% to about 4%, or about 0.5% to about 2% by weight. In some embodiments, the hydroxymethoxyphenyl decanone is provided at about 1.0% by weight.

With respect to polyholosides from flax seeds/linseed, they stimulate glycosaminoglycan (GAG) synthesis. GAGs are fundamental components of the dermis comprising long unbranched chains of high molecular weight consisting of repeating saccharide units. The GAGS synthesis is initiated by the sequential addition of four monosaccharides: xylose-galactose-galactose-glucuronic acid. Xylose, the main pentose of the polyholoside, is the first essential constituent of GAGs and consequently regulates their synthesis. See Wen J, Xiao J, Randar M, et al. Xylose phosphorylation functions as a molecular switch to regulate proteoglycan biosynthesis. *Proc Natl Acad Sci USA* 2014; 111(44): 15723-8.

In some embodiments, formulations as described herein comprise polyholosides. In some embodiments, the polyholosides are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the polyholosides are provided in a range of about 0.25% to about 10%, about 0.5% to about 8%, about 0.75% to about 6%, about 1% to about 4%, or about 2.5% to about 10% by weight. In some embodiments, the polyholosides are provided at about 5.0% by weight.

With respect to phosphatidylserine (PS), aside from its ability to decrease MMP-1 and increase procollagen, it also stimulates intrinsic production of HA. See Cho S, Kim H H, Lee M J, et al. Phosphatidylserine prevents UV-induced decrease of type I procollagen and increase of MMP-1 in dermal fibroblasts and human skin in vivo. *J Lipid Res* 2008; 49(6): 1235-45, and Lee S-H, Yang J-H, Park Y-K, et al. Protective effect and mechanism of phosphatidylserine in UVB-induced human dermal fibroblasts. *European Journal of Lipid Science and Technology* 2013; 115(7): 783-90 In-vitro data on human fibroblast cells shows that PS up-regulates the expression of hyaluronan synthase II enzyme (also called HAS2). This enzyme is a key enzyme for the production of hyaluronic acid within the skin cells. Additional data on artificial skin confirm the up-regulation of hyaluronic acid formation in the presence of PS. See Product monograph; Nagase Chemtex PIPS; Phosphatidylserine & phosphatidylinositol; May 2015.

In some embodiments, formulations as described herein comprise phosphatidylserine. In some embodiments, the phosphatidylserine is provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the phosphatidylserine is provided in a range of about 0.001% to about 6%, about 0.002% to about 4%, about 0.01% to about 3%, about 0.02% to about 2%, or about 0.25% to about 1% by weight. In some embodiments, the phosphatidylserine is provided at about 0.05% by weight. In some embodiments, the phosphatidylserine is provided at about 0.25% by weight. In some embodiments, the phosphatidylserine is provided at about 1% by weight.

With respect to *Saccharomyces cerevisiae*, it increases cellular oxygenation and wound healing while promoting collagen, elastin and HA synthesis. In addition the extract I has been used effectively for reduction in erythema and reduction in sunburn pain. See Product monologue: Active Concepts 2014.

In some embodiments, *Euglena gracilis* extract, aqua, caffeine, *Glaucium flavum* leaf extract, or combinations thereof are used to increase glycosaminoglycans (GAGs). For example, *Euglena gracilis* extract, aqua, caffeine, *Glaucium flavum* leaf extract, or combinations thereof increase hyaluronic acid (HA).

In some embodiments, formulations as described herein comprise *Tremella fuciformis* extract or *Tremella*. *Tremella fuciformis* extract is derived from an edible mushroom. In some embodiments, *Tremella fuciformis* extract provides moisture and serve as a natural hyaluronic acid. In some embodiments, *Tremella fuciformis* extract provides anti-oxidant properties. In some embodiments, *Tremella fuciformis* extract or *Tremella* is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, *Tremella fuciformis* extract or *Tremella* is provided in a range of about 0.25% to about 10%, about 0.5% to about 8%, about 0.75% to about 6%, about 0.5% to about 2.0%, or about 1% to about 4% by weight. In some embodiments, *Tremella fuciformis* extract or *Tremella* is provided at about 0.5%. In some embodiments, *Tremella fuciformis* extract or *Tremella* is provided at about 1.0%. In some embodiments, *Tremella fuciformis* extract or *Tremella* is provided at about 2.0%.

Soothing, Softening Scar Tissue, Smoothing, Pain Relieving, AOX/Pain Relief/Scar Tissue

*Saccharomyces cerevisiae* is a stressed cellular protoplasm yeast extract, it provides a soothing calming effect on sunburned and tender skin and softening of underlying scar tissue. Phytoene/Phytofluene, or Colorless Carotenoids, exhibit anti-oxidative, anti-inflammatory, skin brightening, and UV absorbency properties. *Centella asiatica* hastens healing, stimulates collagen, fibronectin, prevents scarring.

With respect to *Saccharomyces cerevisiae*, it increases cellular oxygenation and wound healing while promoting collagen, elastin and HA synthesis. In addition the extract I has been used effectively for reduction in erythema and reduction in sunburn pain. See Product monologue: Active Concepts 2014.

With respect to phytoene/phytofluene, they are natural colorless carotenoids derived from saltwater micro-algae and used by them for protection against UV radiation and environmental stress. They exhibit anti-oxidant and anti-inflammatory effects (inhibit PGE-2, pro-inflammatory cytokines IL-6 and IL-1 and reduce MMP-1 production).

In some embodiments, formulations as described herein comprise phytoene/phytofluene. In some embodiments, the phytoene/phytofluene is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the phytoene/phytofluene is provided in a range of about 0.25% to about 10%, about 0.5% to about 8%, about 0.75% to about 6%, about 1% to about 4%, or about 0.2% to about 1% by weight. In some embodiments, the phytoene/phytofluene is provided at about 0.2% by weight. In some embodiments, the phytoene/phytofluene is provided at about 0.5% by weight. In some embodiments, the phytoene/phytofluene is provided at about 1.0% by weight.

With respect to *Centella asiatica*, it is effective in improving treatment of small wounds, hypertrophic wounds as well as burns, psoriasis and scleroderma. The mechanism of action involves promoting fibroblast proliferation and increasing the synthesis of collagen and intracellular fibronectin content and also improvement of the tensile strength of newly formed skin as well as inhibiting the inflammatory phase of hypertrophic scars and keloids. Research results indicate that it can be used in the treatment of photoaging skin, cellulite and striae. Bylka W, Znajdek- Awizen P, Studzinska-Sroka E, Brzezinska M. *Centella asiatica* in cosmetology. *Postepy Dermatol Alergol* 2013; 30(1): 46-9

In some embodiments, formulations as described herein comprise *Centella asiatica*. In some embodiments, the *Centella asiatica* is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Centella asiatica* is provided in a range of about 0.25% to about 10%, about 0.5% to about 8%, about 0.75% to about 6%, or about 1% to about 4% by weight. In some embodiments, the *Centella asiatica* is provided at about 1.0% by weight.

Reverse Cellular Senescence—Wake Up Sleeping Dormant Fibroblasts to Produce New Collagen and Elastin and Builds ECM—Improving Tone and Texture of Skin Described herein, in some embodiments, are formulations for reversing cellular senescence. In some embodiments, the formulations reverse fibroblast senescence. In some embodiments, the formulation stimulates collagen and elastin formation. In some embodiments, formulations as described herein comprise *Plantago lanceolata*. In some embodiments, formulations as described herein comprise oleuropein.

Anti-Inflammatory, Pigmentary Control—Improve Pigmentation Problems Particularly Décolleté—AOX/Pigmentation Described herein, in some embodiments, are formulations for pigmentary control. In some embodiments, formulations for pigmentary control improve redness. In some embodiments, formulations for pigmentary control comprise phytoene/phytofluene. In some embodiments, formulations for pigmentary control comprise niacinamide.

Niacinamide or nicotinamide is a biologically active form of niacin (vitamin B3) is well tolerated by the skin. It has been used to treat can and demonstrated to increase ceramide and skin cholesterol levels. In addition, it has been found effective in reducing cutaneous pigmentation by the suppression of melanosome transfer from melanocytes to keratinocytes. See HAKOZAKI T, MINWALLA L, ZHUANG J, et al. The effect of niacinamide on reducing cutaneous pigmentation and suppression of melanosome transfer. *British Journal of Dermatology* 2002; 147: 20-31 and Navarrete-Solis J, Castanedo-Cazares J P, Torres-Alvarez B, et al. A Double-Blind, Randomized Clinical Trial of Niacinamide 4% versus Hydroquinone 4% in the Treatment of Melasma. *Dermatol Res Pract* 2011; 2011: 379173. Niacinamide comprises barrier-protective, anti-inflammatory and depigmenting effects. See Wohlrab J, Kreft D. Niacinamide—mechanisms of action and its topical use in dermatology. *Skin Pharmacol Physiol* 2014; 27(6): 311-5.

In some embodiments, niacinamide is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, niacinamide is provided in a range of about 0.25% to about 10%, about 0.5% to about 8%, about 0.75% to about 6%, or about 1% to about 4% by weight. In some embodiments, niacinamide is provided at about 1% by weight. In some embodiments, niacinamide is provided at about 2% by weight. In some embodiments, niacinamide is provided at about 4% by weight.

Improved Barrier Function—Protection Against Water Loss and the Prevention of Substances and Bacteria Penetrating into the Body, Plumps Skin by Improved Hydration Formulations as described herein, in some embodiments, improve skin barrier function. In some embodiments, formulations for improving skin barrier function comprise niacinamide. In some embodiments, formulations for improving skin barrier function comprise Hydroceramide and hydrogenated lecithin.

In some embodiments, hydrogenated lecithin is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, hydrogenated lecithin is provided in a range of about 0.25% to about 10%, about 0.5% to about 8%, about 0.75% to about 6%, or about 1% to about 4% by weight. In some embodiments, hydrogenated lecithin is provided with C12-16 alcohols, palmitic acid, or combinations thereof. In some embodiments, C12-16 alcohols are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, C12-16 alcohols are provided in a range of about 0.25% to about 10%, about 0.5% to about 8%, about 0.75% to about 6%, or about 1% to about 4% by weight. In some embodiments, palmitic acid is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, palmitic acid is provided in a range of about 0.25% to about 10%, about 0.5% to about 8%, about 0.75% to about 6%, or about 1% to about 4% by weight. In some embodiments, hydrogenated lecithin, C12-16 alcohols, and palmitic acid are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, hydrogenated lecithin, C12-16 alcohols, and palmitic acid are provided in a range of about 0.25% to about 10%, about 0.5% to about 8%, about 0.75% to about 6%, about 1% to about 4%, or about 1% to about 6% by weight. In some embodiments, hydrogenated lecithin, C12-16 alcohols, and palmitic acid are provided at about 4% by weight. In some embodiments, hydrogenated lecithin, C12-16 alcohols, and palmitic acid are provided at about 5% by weight.

The 'skin barrier' functions as a natural frontier between the inner organism and the environment. It is comprised mainly by the epidermis and provides a physical (lipids, corneocytes and an acidic film on the skin surface) and a biochemical barrier provided by the slightly acidic pH. This provides for cutaneous antimicrobial defense and regulates epidermal enzyme activity and expression. The interaction of transepidermal water loss (TEWL), stratum corneum hydration (SC hydration), sebum level on the skin and the skin surface pH value maintains skin barrier functionality and skin appearance. High levels of TEWL correlate with high pH, low stratum corneum hydration and reduced skin surface lipid. There seem to be differences depending on the body site, as TEWL increases significantly with ageing at the décolleté, whereas it decreases significantly at forehead and cheek. See Luebberding S, Krueger N, Kerscher M. Age-related changes in skin barrier function—quantitative evaluation of 150 female subjects. *Int J Cosmet Sci* 2013; 35(2): 183-90. Hydroceramide can reinforce the natural lipid barrier of dry and aging skin and also shows an ability to maintain the moisture balance of skin. In addition hydrogenated lecithin is a natural phospholipid based emulsifier that efficiently penetrates the stratum corneum while preserving skin integrity by merging with the skin and forming a second barrier layer and providing excellent hydration to the skin surface layers.

Other Activity

Caffeine, in vectorized form (with sodium salicylate and lethicin), can also be included in the formulation to promote lipolysis. In some embodiments, the caffeine is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the caffeine is provided in a range of about 0.001% to about 6%, about 0.002% to about 4%, about 0.01% to about 3%, or about 0.02% to about 2%. In some embodiments, caffeine is provided with sodium salicylate, lecithin, silica, or combinations thereof. In some embodiments, the sodium salicylate, lecithin, or silica are each provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the sodium salicylate, lecithin, or silica are each provided in a range of about 0.001% to about 6%, about 0.002% to about 4%, about 0.01% to about 3%, or about 0.02% to about 2% by weight. In some embodiments, the caffeine, sodium salicylate, lecithin, and silica are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the caffeine, sodium salicylate, lecithin, and silica are provided in a range of about 0.001% to about 6%, about 0.002% to about 4%, about 0.01% to about 3%, or about 0.02% to about 2% by weight. In some embodiments, the caffeine, sodium salicylate, lecithin, and silica are provided at about 0.02% by weight.

Formulations as described herein, in some embodiments, comprise ceramide NP. In some embodiments, the ceramide NP is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the ceramide NP is provided in a range of about 0.001% to about 6%, about 0.002% to about 4%, about 0.01% to about 3%, about 0.02% to about 2%, or about 0.50% to about 0.20% by weight. In some embodiments, the ceramide NP is provided at about 0.05% by weight. In some embodiments, the ceramide NP is provided at about 0.10% by weight. In some embodiments, the ceramide NP is provided at about 0.20% by weight.

Therapeutic Uses

The formulations described herein are useful in conjunction with body shaping techniques, such as non-invasive radiofrequency (RF)-based technology (hot) or cryo-based technologies (cold). RF technology involves electric energy rather than photo-energy, often utilizing skin sparing techniques or insulated needles where these are utilized and thus the epidermis is largely unaffected and untargeted in these situations. Accordingly, topical formulations, such as those described herein, which tighten skin are complementary adjuncts to such procedures enhancing the overall outcome.

Described herein are formulations for use alone to improve skin laxity and reduce fat. In some embodiments, formulations result in both removal of fat and tightening of laxed skin as fat is being removed.

In some instances, the topical formulations described herein are administered once per day, twice per day, three times per day or more. In some instances, the topical formulations described herein are administered twice per day. The topical formulations described herein, in some embodiments, are administered daily, every day, every alternate day, five days a week, once a week, every other week, two weeks per month, three weeks per month, once a month, twice a month, three times per month, or more. In some embodiments, the topical formulations described herein are administered twice daily, e.g., morning and evening. In some embodiments, the topical formulations described herein are administered for at least 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, 10 years, or more. In some embodiments, the topical formulations described herein are administered twice daily for at least or about 1 week, 2 weeks, 3 weeks, 1 month, 2 months, 3 months, 4 months, 5 months, 6 months, or more. In some embodiments, the topical formulations described herein are administered once daily, twice daily, three times daily, four times daily, or more than four times daily for at least or about 1 week, 2 weeks, 3 weeks, 1 month, 2 months, 3 months, 4 months, 5 months, 6 months, or more.

While the formulations and compositions described herein are particularly useful in situations where skin tightening is desirable, they can also be suitable for other uses, such as skincare treatment, promoting skin regeneration, and promoting enhanced wound healing.

In some embodiments, the formulations described herein are used in conjunction with a fat reduction procedure. In some embodiments, the fat reduction procedure is non-invasive. Exemplary non-invasive fat reduction procedures include, but are not limited to, low level laser therapy, infrared light, ultrasound, radiofrequency, and cryolipolysis.

Formulations as described herein used in conjunction with a fat reduction procedure, in some embodiments, speed up fat elimination following the fat reduction procedure. In some embodiments, the formulations as described herein speed up fat elimination by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the formulations as described herein speed up fat elimination by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

In some instances, the formulations described herein are administered up to 1 day, up to 2 days, up to 3 days, up to 5 days, or more than 5 days following a fat reduction procedure. In some instances, the formulations described herein are administered up to 1 hour, up to 2 hours, up to 3 hours, up to 5 hours, up to 6 hours, up to 7 hours, up to 8 hours, up to 12 hours, up to 16 hours, up to 20 hours, or up to 24 hours following a fat reduction procedure. Sometimes the formulations described herein are administered singly, or over a time course, such as daily, multiple times weekly, weekly, biweekly, monthly or less frequently following a fat reduction procedure. In some instances, the formulations described herein are administered singly, or over a time course, such as daily, multiple times weekly, weekly, biweekly, monthly or more frequently following a fat reduction procedure. In some embodiments, the formulations are topical formulations. In some instances, the topical formulations are administered twice daily for at least or about 1 week, 2 weeks, 3 weeks, 1 month, 2 months, 3 months, 4 months, 5 months, 6 months, or more following a fat reduction procedure. In some embodiments, the topical formulations described herein are administered once daily, twice daily, three times daily, four times daily, or more than four times daily for at least or about 1 week, 2 weeks, 3 weeks, 1 month, 2 months, 3 months, 4 months, 5 months, 6 months, or more following a fat reduction procedure. The fat reduction procedure may be low level laser therapy, infrared light, ultrasound, radiofrequency, or cryolipolysis. In some instances, the fat reduction procedure is cryolipolysis.

Formulations as described herein when administered prior to, during, or following a fat reduction procedure may improve fat reduction. In some instances, reduction is by 10%, 15%, 20%, 25%, 30%, 35%, 40%, 45%, 50%, 55%, 60%, 65%, 70%, 75%, 80%, 85%, 90%, 95%, or more than 95% as compared to a control. In some instances, the reduction is by at least or about 1 cm$^3$, 2 cm$^3$, 3 cm$^3$, 4 cm$^3$, 5 cm$^3$, 6 cm$^3$, 7 cm$^3$, 8 cm$^3$, 9 cm$^3$, 10 cm$^3$, 11 cm$^3$, 12 cm$^3$, 13 cm$^3$, 14 cm$^3$, 15 cm$^3$, 16 cm$^3$, 17 cm$^3$, 18 cm$^3$, 19 cm$^3$, 20 cm$^3$, 25 cm$^3$, 30 cm$^3$, 35 cm$^3$, 40 cm$^3$, 50 cm$^3$, 60 cm$^3$, 70 cm$^3$, 80 cm$^3$, or more than 80 cm$^3$. In some instances, the reduction is in a range of about 1 cm$^3$ to about 80 cm$^3$, about 5 cm$^3$ to about 70 cm$^3$, about 10 cm$^3$ to about 600 cm$^3$, or about 20 cm$^3$ to about 40 cm$^3$. In some instances, the reduction is in the abdomen. In some instances, the reduction is in the arm. In some instances, the reduction is in a submental region, abdomen, face, flank, back, chest, arm, leg, buttock, or combination thereof.

Formulations as described herein when applied to a submental region, abdomen, face, flank, back, chest, arm, leg, buttock, or combination thereof may result in a fat reduction. In some instances, the fat reduction is in the abdomen. In some instances, the formulations are applied following a fat reduction procedure such as cryolipolysis. In some instances, the reduction occurs at least or about 1 week, 2 weeks, 3 weeks, 1 month, 2 months, 3 months, 4 months, 5 months, 6 months, or more following a fat reduction procedure. In some instances, the reduction occurs when the topical formulations are administered once daily, twice daily, three times daily, four times daily, or more than four times daily for at least or about 1 week, 2 weeks, 3 weeks, 1 month, 2 months, 3 months, 4 months, 5 months, 6 months, or more following a fat reduction procedure.

In some embodiments, the formulations described herein are used in conjunction with body-shaping or body-contouring procedures. In some embodiments, the body-shaping or body-contouring procedure is a fat reduction procedure. In some embodiments, the body-shaping or body-contouring procedures are non-invasive. In some embodiments, the body-shaping or body-contouring procedure uses a specific energy source. In some embodiments, the body-shaping or body-contouring procedure affects fat tissue including, but not limited to, short term metabolic size reduction and long term permanent fat cell death. Exemplary body-shaping or body-contouring procedures include, but are not limited to, high frequency focused ultrasound, pulsed focus ultrasound, cryolipolysis, radiofrequency induced electroporation, injectable lipolytic agents, and liposuction.

In some instances, the formulations described herein are administered prior to a body-shaping or body-contouring procedure, during a body-shaping or body-contouring procedure, or following a body-shaping or body-contouring procedure. In additional instances, the formulations described herein are administered as a pre-conditioning treatment. In some instances, the topical formulation described herein are administered for at least 1 day, 2 days, 3 days, 4 days, 5 days, 6 days, 1 week, 2 weeks, 3 weeks, 1 month, 2 months, 3 months, 4 months, 5 months, 6 months, or more as a pre-conditioning treatment. In some instances, the topical formulations described herein are administered for at least 2-8 weeks, 2-6 weeks, 2-4 weeks, or 2-3 weeks as a pre-conditioning treatment. In some cases, the formulations described herein are administered at least 1 day, 2 days, 3 days, 4 days, 5 days, 6 days, 1 week, 2 weeks, 3 weeks, 1 month, 2 months, 3 months, 4 months, 5 months, 6 months, or more prior to a body-shaping or body-contouring procedure. In some instances, the formulations described herein are administered up to 1 hour, up to 2 hours, up to 3 hours, up to 5 hours, up to 6 hours, up to 7 hours, up to 8 hours, up to 12 hours, up to 16 hours, up to 20 hours, or up to 24 hours following a body-shaping or body-contouring procedure. In some cases, the formulations described herein are administered at least or up to 1 day, 2 days, 3 days, 4 days, 5 days, 6 days, 1 week, 2 weeks, 3 weeks, 1 month, 2 months, 3 months, 4 months, 5 months, 6 months, or more following a body-shaping or body-contouring procedure. In some embodiments, the topical formulations described herein are administered for at least 2-8 weeks, 2-6 weeks, 2-4 weeks, or 2-3 weeks after a body-shaping or body-contouring procedure. Sometimes the formulations described herein are administered singly, or over a time course, such as daily, multiple times weekly, weekly, biweekly, monthly or less frequently prior to or following a body-shaping or body-contouring procedure. In some instances, the formulations described herein are administered singly, or over a time course, such as daily, multiple times weekly, weekly, biweekly, monthly or more frequently prior to or following a body-shaping or body-contouring procedure. In some instances, the topical formulations described herein are administered once per day, twice per day, three times per day or more after the end of a body-shaping or body-contouring procedure. In some instances, the topical formulations described herein are administered twice daily administration, e.g., morning and evening, after the end of a body-shaping or body-contouring procedure.

In some instances, formulation as described herein when applied to a submental region, abdomen, face, flank, back, chest, arm, leg, buttock, or combination thereof results in improved contour or improved shape. In some instances, the improved contour or improved shape is of the arm. In some instances, the improved contour or improved shape occurs at least or about 1 week, 2 weeks, 3 weeks, 1 month, 2 months, 3 months, 4 months, 5 months, 6 months, or more following a body contouring procedure. In some instances, the improved contour or improved shape occurs when the topical formulations are administered once daily, twice daily, three times daily, four times daily, or more than four times daily for at least or about 1 week, 2 weeks, 3 weeks, 1 month, 2 months, 3 months, 4 months, 5 months, 6 months, or more following a body contouring procedure.

Improved contour or improved shape may be by at least or about 10%, 15%, 20%, 25%, 30%, 35%, 40%, 45%, 50%, 55%, 60%, 65%, 70%, 75%, 80%, 85%, 90%, 95%, or more than 95% as compared to a control. In some instances, the improved contour or improved shape comprises a reduction in size of a submental region, abdomen, face, flank, back, chest, arm, leg, buttock, or combination thereof. In some instances, improved contour or improved shape comprises a reduction in size of the arm. In some instances, improved contour or improved shape results in a reduction of by at least or about 0.25 inch, 0.5 inch, 0.75 inch, 1 inch, 2 inches, 2.5 inches, 3 inches, 3.5 inches, 4 inches, 4.5 inches, 5 inches, 5.5 inches, 6 inches, 7 inches, 8 inches, 9 inches, 10 inches, or more than 10 inches. In some instances, improved contour or improved shape results in a reduction of about 0.25 inch to about 10 inches, 0.5 inch to about 9 inches, about 0.75 inch to about 8 inches, 1 inch to about 7 inches, or about 2 inches to about 6 inches.

Fat reduction, improved contour, improved shape, or combinations thereof may be determined using various assays. In some instances, skin laxity, body contour/shape, size, or aesthetics are determined. Exemplary assessments include, but are not limited to, skin laxity assessments, circumference measurements, photographic assessments, contour improvement assessments, arm shape improvement assessments, and global aesthetic improvement of skin quality assessments. The assessments may be determined by a clinician or doctor. In some instances, the assessments are determined by the patient.

In making an assessment, the effects of the topical formulations may be compared to a control. In some instances, an individual topically administers formulations as described herein on one part of the body, and the control comprises a control formulation administered to a second part of the body.

In some embodiments, the formulations described herein are used in conjunction with a procedure to reduce skin laxity. Exemplary procedures to reduce skin laxity comprise radiofrequency or ultrasound.

In some instances, the formulations described herein are administered prior to a procedure to reduce skin laxity, during a procedure to reduce skin laxity, or following a procedure to reduce skin laxity. In additional instances, the formulations described herein are administered as a pre-conditioning treatment. In some instances, the topical formulation described herein are administered for at least 1 day, 2 days, 3 days, 4 days, 5 days, 6 days, 1 week, 2 weeks, 3 weeks, 1 month, 2 months, 3 months, 4 months, 5 months, 6 months, or more as a pre-conditioning treatment. In some instances, the topical formulations described herein are administered for at least 2-8 weeks, 2-6 weeks, 2-4 weeks, or 2-3 weeks as a pre-conditioning treatment. In some cases, the formulations described herein are administered at least 1 day, 2 days, 3 days, 4 days, 5 days, 6 days, 1 week, 2 weeks, 3 weeks, 1 month, 2 months, 3 months, 4 months, 5 months, 6 months, or more prior to a procedure to reduce skin laxity. In some cases, the formulations described herein are administered at least 1 day, 2 days, 3 days, 4 days, 5 days, 6 days, 1 week, 2 weeks, 3 weeks, 1 month, 2 months, 3 months, 4 months, 5 months, 6 months, or more following a procedure to reduce skin laxity. In some embodiments, the topical formulations described herein are administered for at least 2-8 weeks, 2-6 weeks, 2-4 weeks, or 2-3 weeks after a procedure to reduce skin laxity. Sometimes the formulations described herein are administered singly, or over a time course, such as daily, multiple times weekly, weekly, biweekly, monthly or less frequently prior to or following a procedure to reduce skin laxity. In some instances, the formulations described herein are administered singly, or over a time course, such as daily, multiple times weekly, weekly, biweekly, monthly or more frequently prior to or following a procedure to reduce skin laxity. In some instances, the topical formulations described herein are administered once per day, twice per day, three times per day or more after the end of a procedure to reduce skin laxity. In some instances, the topical formulations described herein are administered twice daily administration, e.g., morning and evening, after the end of a procedure to reduce skin laxity.

Described herein are formulations for reducing skin laxity and reducing fat. In some embodiments, formulations result in both removal of fat and tightening of laxed skin as fat is being removed. For example, hexapeptide-11 results in removal of fat and tripeptide-1 and hexapeptide-12 result in skin tightening.

Figure 3:
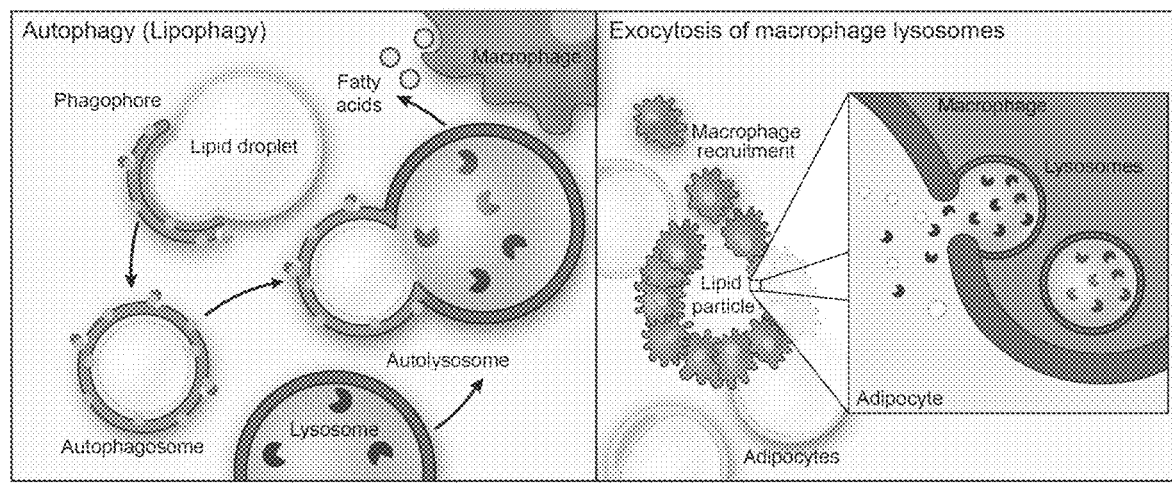
FIG. 3 illustrates a schematic of autophagy (lipophagy).

In some embodiments, formulations as described herein stimulate elastin production. In some embodiments, formulations as described herein aid in elimination of lipid droplets. In some embodiments, formulations as described herein stimulate autophagy and macrophage production to accelerate digestion of fat fragments. FIG. 3 illustrates a schematic of autophagy. Autophagy facilitates very large sized fat cells and lipid droplets (much bigger than macrophages) to be digested. The process takes place by surrounding part of the fat droplet with a cell membrane part (phagophore), which then breaks down the droplet into a smaller more digestable size and further fuses with a lysosome that pours enzymes into the droplet further breaking it down into a still smaller size. This particle can now be digested by macrophages which are drawn into the area by the process.

In some embodiments, formulations as described herein increase elastin production by increasing elastin components and fibroblast function. See FIG. 4. In some embodiments, formulations as described herein increase GAGs (Glycosaminoglycans) and Hyaluronic acid (HA).

Types of Formulations

The peptide combinations of the embodiments can be employed in various types of formulations. Topical formulations including a dipeptide, tripeptide, or tetrapeptide, and a pentapeptide, hexapeptide, or heptapeptide in combination with at least one excipient, are provided. In some embodiments, topical formulations comprise one or more tripeptides, one or more tetrapeptides, and one or more hexapeptides. In some embodiments, a tripeptide of the one or more tripeptides is tripeptide-1. In some embodiments, a tetrapeptide of the one or more tetrapeptides is tetrapeptide-2. In some embodiments, a hexapeptide of the one or more hexapeptides is hexapeptide-12. In some embodiments, a hexapeptide of the one or more hexapeptides is hexapeptide-11. In some embodiments, the topical formulation comprises tripeptide-1, tetrapeptide-2, hexapeptide-12, and hexapeptide-11. In some embodiments, the topical formulation comprises tripeptide-1, tetrapeptide-2, and hexapeptide-12. Excipients can include a nonaqueous or aqueous carrier, and one or more agents selected from moisturizing agents, pH adjusting agents, deodorants, fragrances, chelating agents, preservatives, emulsifiers, thickeners, solubilizing agents, penetration enhancers, anti-irritants, colorants, surfactants, beneficial agents, pharmaceutical agents, and other components as known in the art for use in connection with topical formulations for treatment of the skin. In some embodiments, the formulation is an aqueous formulation. In some embodiments, the formulation is an anhydrous formulation to prevent skin irritation such as water-based irritant contact dermatitis or stinging sensation upon application to damaged skin. In some embodiments, the composition is formulated such that preservatives need not be employed (e.g., a preservative-free formulation) so as to avoid skin irritation associated with certain preservatives.

To facilitate application, the composition may be provided as an ointment, an oil, a lotion, a paste, a powder, a gel, or a cream. The composition may also include additional ingredients such as a protective agent, an emollient, an astringent, a humectant, a sun screening agent, a sun tanning agent, a UV absorbing agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an additional antioxidant agent, a chemotherapeutic agent, an anti-histamine agent, a vitamin or vitamin complex, a hormone, an anti-dandruff agent, an anti-wrinkle agent, an anti-skin atrophy agent, a skin whitening agent, a cleansing agent, additional peptides, additional modified peptides, and combinations thereof. In a further embodiment, the composition may avoid animal or cellular-based materials to avoid skin irritation. The composition can be applied to the dermis, or to mucous membranes.

Methods of using topical peptide formulations for skin tightening are provided. The compositions may also be applied to treat skin conditions such as inflammation, redness, soreness, skin sensitivity, dry skin, bruising, and similar conditions. Application of the peptide composition comprising a first dipeptide, tripeptide, or tetrapeptide and a second pentapeptide, hexapeptide, or heptapeptide may also be used to prevent scarring (e.g., in facelift procedures or other cosmetic procedures involving a skin incision), to quicken epithelial confluence, and to limit scabbing and crusting during wound healing. Increased collagen production and/or increased elastin production can also be induced through the application of a composition that comprises a first dipeptide, tripeptide, or tetrapeptide and a second pentapeptide, hexapeptide, or heptapeptide. Suitable methods for objectively measuring improvement in skin redness and inflammation may include tristimulus colorimetry, narrow-band reflectance spectroscopy, diffuse reflectance spectroscopy, skin reflectance spectroscopy, and/or UV photography.

Some embodiments include administering peptide compositions provided herein in topical formulations; however, other routes of administration are also contemplated (e.g., mucosal, subdermal, oral, or the like). Contemplated routes of administration include but are not limited to topical, mucosal, and subcutaneous. Suitable liquid forms include suspensions, emulsions, solutions, and the like. Unit dosage forms can also be provided, e.g., individual packets with a premeasured amount of the formulation, configured for administration to the face or other body part on a predetermined schedule pre-procedure and post-procedure. Unit dosage forms configured for administration twice or three times a day pre-procedure and post-procedure are particularly preferred; however, in certain embodiments it can be desirable to configure the unit dosage form for administration once a day, four times a day, or more.

In some embodiments, the topical and other formulations typically comprise from about 0.001 wt. % or less to about 50 wt. % or more of active ingredient, such as the peptides, preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %. In some embodiments, the active ingredient is provided at least or about 0.001%, 0.005%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the active ingredient is provided in a range of about 0.25% to about 10%, about 0.5% to about 8%, about 0.75% to about 6%, or about 1% to about 4% by weight. In some embodiments, the active ingredient is provided in a range of about 0.001% to about 6%, about 0.002% to about 4%, about 0.01% to about 3%, or about 0.02% to about 2% by weight.

Compositions and formulations for topical administration can include transdermal patches, ointments, lotions, creams, gels, drops, sprays, liquids, aerosols, and powders. Conventional pharmaceutical carriers, aqueous, powder or oily bases, thickeners and the like may be employed. In certain applications, an ointment, lotion, cream, gel or similar formulation can be provided that can be applied to the skin using the fingers. Such formulations are typically provided in a squeeze tube or bottle or a pot, or in a roll-on, wherein a ball is secured in the top of a container of the formulation, wherein the ball is permitted to roll. By rolling the ball over the skin surface, liquid in the container is transferred to the skin in a controlled manner. An alternative delivery mechanism includes a container with a perforated lid with a mechanism for advancing an extrudable formulation through the lid. In another form, a gel formulation with sufficient structural integrity to maintain its shape is provided, which is advanced up a tube and applied to the skin (e.g., in a stick form). An advantage of the stick form is that only the formulation contacts the skin in the application process, not the fingers or a portion of a container. A liquid or gel can also be placed using an applicator, e.g., a wand, a sponge, a syringe, or other suitable method.

Components of the Formulations

Peptides

Formulations comprising a combination of two or more peptides are provided for promoting healthy skin, skin regeneration, and enhanced wound healing, e.g., in patients subject to a skin procedure such as a laser treatment, a chemical peel, dermabrasion, microneedling, and other such procedures, in patients subject to any other treatment or exposure resulting in damage, inflammation, or irritation to the skin (e.g., sunburn, eczema, psoriasis, herpes lesions, shingles, allergic reaction, contact dermatitis, or the like), or in any skin condition wherein stimulation of collagen and/or elastin is beneficial. In a topical formulation comprising the two peptide combination, a first peptide (e.g., hexapeptide) is present in the composition in pure for or in a form of a carrier containing the peptide, e.g., 50 ppm or less to 1000, 5000, 10000, 50000, 100000, 500000 ppm or more, e.g., 100 ppm of the peptide. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 10 wt. % of the first peptide. The second peptide (e.g., tripeptide) is present in the topical formulation composition in pure form or in a form of a carrier containing the peptide, e.g., 50 ppm or less to 1000, 5000, 10000, 50000, 100000, 500000 ppm or more, e.g., 100 ppm of the peptide, or any other suitable amount. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 20 wt. % of the second peptide. The amount of peptide in the base can be adjusted up or down.

Formulations as described herein, in some embodiments, comprise one or more peptides. In some embodiments, the one or more peptides is provided at least or about 0.001%, 0.005%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the one or more peptides is provided in a range of about 0.25% to about 10%, about 0.5% to about 8%, about 0.75% to about 6%, or about 1% to about 4% by weight. In some embodiments, the one or more peptides is provided in a range of about 0.001% to about 6%, about 0.002% to about 4%, about 0.01% to about 3%, or about 0.02% to about 2% by weight.

In some embodiments, the peptide of the one or more peptides is tripeptide-1, tetrapeptide-2, hexapeptide-12, or hexapeptide-11. In some embodiments, the tripeptide-1 is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the tripeptide-1 is provided in a range of about 0.25% to about 10%, about 0.5% to about 8%, about 0.75% to about 6%, or about 1% to about 4% by weight. In some embodiments, the tetrapeptide-2 is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the tetrapeptide-2 is provided in a range of about 0.25% to about 10%, about 0.5% to about 8%, about 0.75% to about 6%, or about 1% to about 4% by weight. In some embodiments, the hexapeptide-12 is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hexapeptide-12 is provided in a range of about 0.25% to about 10%, about 0.5% to about 8%, about 0.75% to about 6%, or about 1% to about 4% by weight. In some embodiments, the hexapeptide-11 is provided at least or about 0.001%, 0.005%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hexapeptide-11 is provided in a range of about 0.25% to about 10%, about 0.5% to about 8%, about 0.75% to about 6%, or about 1% to about 4% by weight. In some embodiments, the hexapeptide-11 is provided in a range of about 0.001% to about 6%, about 0.002% to about 4%, about 0.01% to about 3%, or about 0.02% to about 2%. In some embodiments, the hexapeptide-11 is provided in a range of about 0.005% to about 0.02% by weight.

In example embodiments, a weight ratio for the first peptide to the second peptide in a topical formulation is 1 part first peptide to 0.2 to 10 parts second peptide, or 1 to 10 parts second peptide, or 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In some embodiments, the dipeptide has the following amino acid sequence: KV. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the tripeptide has the following amino acid sequence: KVK. In some embodiments, the first peptide is a tetrapeptide. Suitable tetrapeptides include but are not limited to those having the following sequence of amino acids: GQPR (SEQ ID NO: 1), KTFK (SEQ ID NO: 2), AQTR (SEQ ID NO: 3), or RSRK (SEQ ID NO: 4). In some embodiments, the tetrapeptide has the following sequence of amino acids: KDVY (SEQ ID NO: 5). In some embodiments, the second peptide is a pentapeptide. Suitable pentapeptides include but are not limited to those having the following sequence of amino acids: KTTKS (SEQ ID NO: 6), YGGFX (SEQ ID NO: 7), or KLAAK (SEQ ID NO: 8). In some embodiments, the second peptide is a hexapeptide. Suitable hexapeptides include but are not limited to those having the following sequence of amino acids: VGVAPG (SEQ ID NO: 9) or GKTTKS (SEQ ID NO: 10). In some embodiments, the hexapeptide has the following sequence of amino acids: FVAPFP (SEQ ID NO: 11). In some embodiments, the second peptide is a heptapeptide. Suitable heptapeptides include but are not limited to one having an amino acid sequence RGYYLLE (SEQ ID NO: 12), or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide. In some embodiments, the compositions comprise one or more tripeptides, one or more tetrapeptides, and one or more hexapeptides. In some embodiments, a tripeptide of the one or more tripeptides is tripeptide-1. In some embodiments, a tetrapeptide of the one or more tetrapeptides is tetrapeptide-2. In some embodiments, a hexapeptide of the one or more hexapeptides is hexapeptide-12. In some embodiments, a hexapeptide of the one or more hexapeptides is hexapeptide-11. In some embodiments, the compositions comprise tripeptide-1, tetrapeptide-2, hexapeptide-12, and hexapeptide-11. In some embodiments, the compositions comprise tripeptide-1, tetrapeptide-2, and hexapeptide-12.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG (SEQ ID NO: 9)), palmitoyl tripeptide-1 (Pal-GHK), myristoyl hexapeptide-12 (Myr-VGVAPG (SEQ ID NO: 9)), myristoyl tripeptide-1 (Myr-GHK). Palmitoyl or myristoyl functionalization can be desirable in certain embodiments as it exhibits enhanced penetration when compared to other fatty acids. In some embodiments, the peptide is functionalized with a chemical group. For example, the peptide is functionalized with acetyl. Examples include acetyl tetrapeptide-2.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

GHK acts as an anti-inflammatory (see, e.g., Pickart, L., The human tri-peptide GHK and tissue remodeling, J. Biomater. Sci. Polymer Edn. 2008, Vol. 19, pp. 969-988, 972-973; Pickart et al., The Human Tripeptide GHK-CU in Prevention of Oxidative Stress and Degenerative Conditions of Aging: Implications for Cognitive Health, Oxid. Med. Cell Longev. 2012, Vol. 2012, pp. 1-8, 3) and an antioxidant. GHK acts to promote wound healing by suppressing the "acute phase response" that can produce both inflammation and induce scarring. This biological response prevents the invasion of bacteria, facilitates the arrival of immune cells, stems bleeding, and provides a covering for the wounded area. GHK-Cu also suppresses the acute phase response by inhibiting the production of molecules called cytokines. Cytokines are immune cell signaling molecules that attract immune cells and that trigger the production of other molecules that promote inflammation and fibrosis (leading to the creation of scar tissue). In particular, GHK suppresses the production of cytokines including tumor necrosis factor-alpha (TNFα), interleukin-1 (IL-1), interleukin-6 (IL-6), and transforming growth factor-beta-1 (TGF-β1), a few of the key drivers of inflammation and apoptotic cell death in the wound region. As TGF-β1 is an important component for the continuation of the acute phase response, GHK's suppression of TGF-β1 also acts to shorten the duration of the acute phase response once it has begun. GHK acts as an antioxidant by blocking ferritin's release of oxidizing iron, preventing further inflammation or microbial infection (as invading microbes need iron to survive).

GHK also stimulates blood vessel growth, increases collagen production, and regenerates the extracellular matrix. GHK acts as an attractant for cells vital to the regeneration of damaged tissues such as capillary cells that rebuild blood vessels. It also upregulates the production of a variety of enzymes that remove damaged proteins while also rebuilding the extracellular matrix (ECM), a key external scaffold that is important for intercellular communication and support. In particular, GHK's induces the production of messenger RNAs (mRNAs) necessary for the regeneration of the ECM, namely collagen, proteoglycans, glycosaminoglycans, chondroitin sulfate, and dermatan sulfate. GHK's induction of increased collagen production also plays a key role in enhancing skin regrowth. GHK further stimulates blood flow into damaged tissues through three processes: angiogenesis, anti-coagulation and vascular dilation. First, GHK induces angiogenesis or new blood vessel formation by increasing the production of growth factor proteins necessary for angiogenesis such as basic fibroblast growth factor (BFGF) and vascular endothelial growth factor (VEGF). Second, GHK increases blood flow to the wounded area by expanding the number of red blood cells (via growth in erythropoietin production) and by anti-coagulatory effects such as downregulating the blood clotting molecule thromboxane. Third, GHK facilitates vascular dilation through binding to the vasoconstriction protein angiotensin II, preventing angiotensin from constricting blood vessels and reducing blood flow.

GHK promotes stem cell proliferation (see, e.g., Ito et al., Is the Hair Follicle Necessary for Normal Wound Healing, J. Invest. Dermatol. 2008, Vol. 128, pp. 1059-1061, 1059). Wound healing studies have demonstrated that the addition of GHK-Cu greatly enlarged the production of hair follicles near the wound periphery in experiments with mice. Dermal hair follicles are a significant source of stem cells that are essential for dermal healing. Research into dermal hair follicles have demonstrated that hair-bearing areas tend to heal more quickly and that cells from various portions of the follicle may contribute to both dermal cell and epithelial cell replacement as well.

Thus, by decreasing inflammation, acting as an antioxidant, stimulating growth of new blood vessels, regenerating the extracellular matrix, enhancing collagen production, and by promoting stem cell proliferation, GHK can greatly enhance skin regeneration and promote wound healing.

Some embodiments of the methods and compositions provided herein include as a second peptide valine-glycine-valine-alanine-proline-glycine (VGVAPG) (SEQ ID NO: 9). VGVAPG (SEQ ID NO: 9) is a hexapeptide that is derived from the elastin protein (see, e.g., Blanchevoye et al., Interaction between the Elastin Peptide VGVAPG and Human Elastin Binding Protein, J. Biol. Chem. 2012, Vol. 288, pp. 1317-1328, 1317-1318) ("VGVAPG" disclosed as SEQ ID NO: 9). Elastin is a protein found in connective tissue (e.g. skin) that is necessary for tissues to return to their original shape and size after undergoing temporary expansion or contraction. Due to the importance of elastin in providing elasticity and resilience, elastin plays a significant role in skin cell resistance to injury and recovery from injury. The ability of skin to return to its original form after undergoing stretching or pulling relies on cross-linked elastin proteins (tropoelastin proteins in humans) that work to form "elastic fibers." The disruption of the elastic fiber system in healing wounds has been strongly linked to the production of scar tissue (see, e.g., Rnjak-Kovacina et al., Severe Burn Injuries and the Role of Elastin in the Design of Dermal Substitutes, Tissue Eng. Part B. Rev. 2011, pp. 81-91, 85-86). Because of these properties and others, elastin is a key component in the effective wound healing process.

VGVAPG (SEQ ID NO: 9) plays a role in facilitating elastin's ability to prevent skin injury and to promote skin regeneration (see, e.g., Floquet et al., Structural Characterization of VGVAPG, an Elastin-Derived Peptide, Biopolymers (Peptide Science) 2004, Vol. 76, 266-280, 267) ("VGVAPG" disclosed as SEQ ID NO: 9). First, it has been shown to demonstrate the ability to attract monocytes and fibroblasts (see, e.g., Senior et al., Val-Gly-Val-Ala-Pro-Gly, a Repeating Peptide in Elastin, Is Chemotactic for Fibroblasts and Monocytes, J. Cell Biol. 1984, Vol. 99, pp. 870-874, 870) ("Val-Gly-Val-Ala-Pro-Gly" disclosed as SEQ ID NO: 9), monocytes being essential for fighting off infection and fibroblasts being necessary for collagen production (the most abundant protein in skin) and for the regeneration of the extracellular matrix. Second, VGVAPG (SEQ ID NO: 9) provides a binding site for elastin-binding protein, a permanent component of mature elastic fibers. Third, VGVAPG (SEQ ID NO: 9) provides a binding site for elastin and extracellular matrix degradation enzymes such as matrix metalloproteinases (MMPs), which facilitate the replacement and regeneration of elastic fibers and extracellular matrix proteins.

The tripeptide and hexapeptide work synergistically to promote skin regeneration and wound healing through the attraction of healing cells, increased production of elastin and collagen, enhanced fibroblast proliferation, antioxidant behavior (preventing the release of oxidizing iron), and inducing the regeneration of the extracellular matrix. As a result, the combination of the two peptides exhibits synergistic, superior performance well beyond that expected for either of the two peptides alone.

Tripeptides promote skin regeneration through increased collagen and elastin synthesis, blocking ferritin release of oxidized iron, attracting healing cells such as capillary cells and macrophages, and through re-establishing new blood flow to the injury site. The tripeptide functions as an anti-oxidant, stimulates collagen, elastin, and hyaluronic acid. It is formulated to penetrate stratum corneum. In the extracellular matrix (ECM), it is an anti-oxidant, attracts capillaries and macrophages, which facilitates wound healing. In the cell, it decreases inflammatory cytokines, increases collagen, elastin, dermal stem cell proliferation, and hyaluronic acid.

Hexapeptides promote skin regeneration and wound healing through the induction of elastin and collagen production, fibroblast proliferation, regeneration of the extracellular matrix, and fibroblast keratinocyte mobility. The hexapeptide is formulated to penetrate the stratum corneum, and mimics the elastin binding sequence, to stimulate elastin. It binds specifically to EBP receptors on fibroblasts and keratinocytes. The binding initiates intracellular signal transduction. Hexapeptides suitable for use include Hexapeptide-12 and Hexapeptide-11. Hexapeptide-11 has the sequence: Hex-11 (Phe-Val-Ala-Pro-Phe-Pro (FVAPFP) (SEQ ID NO: 11). Hexapeptide-12 has the sequence: VGVAPG (SEQ ID NO: 9).

In topical formulations, the tripeptide is typically present in an amount of from about 50 ppm or less to about 100, 200, 300, 400, or 500 ppm or more, e.g., 50 ppm to 150 ppm.

In topical formulations, the hexapeptide is typically present in an amount of from about 50 ppm or less to about 100, 200, 300, 400, or 500 ppm or more, e.g., 50 ppm to 150 ppm.

The peptides can advantageously be provided in a base for suitable for combining with other components of a topical formulation. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisettling agent (e.g., disteardimonium hectorite).

Oleuropein

In some embodiments, polyphenols such as oleuropein may be added to the compositions. Oleuropein is a polyphenol isolated from olive leaves (see e.g. Omar S H. Oleuropein in olive and its pharmacological effects. *Sci Pharm* 2010; 78(2): 133-54; Al-Rimawi F, Yateem H, Afaneh I. Formulation and evaluation of a moisturizing day cream containing olive leaves extract. International Journal of Development Research 2014; 4(10): 1996-2000; Kontogianni V G, Charisiadis P, Margianni E, Lamari F N, Gerothanassis I P, Tzakos A G. Olive leaf extracts are a natural source of advanced glycation end product inhibitors. Journal of medicinal food 2013; 16(9): 817-22). Oleuropein demonstrates major anti-inflammatory effects by inhibiting lipoxygenase activity and the production of leukotriene. More particularly researchers have demonstrated that oleuropein enhances proteasome activities in vitro more effectively than other known chemical activators, possibly through conformational changes of the proteasome. In this regard, it decreases reactive oxygen species (ROS), reduces the amount of oxidized proteins through increased proteasome-mediated degradation through increased proteasome-mediated degradation and autophagic pathways, and retains proteasome function during replicative senescence. Inhibition of AGE formation via blocking sugar attachment to proteins, scavenging the reactive intermediates, or breakdown of established AGE-induced cross-links constitutes an attractive therapeutic/preventive target. Oleuropein has been demonstrated to inhibit AGE formation and breakdown AGE products through its proteasome enhancing function. When oleuropein is employed in a topical formulation, it is preferably present at from about 0.005% by weight or less to about 10.0% by weight or more, typically at from about 0.01% by weight to about 5.0% by weight, e.g., at from about 0.05% by weight to about 0.1% by weight. Oleuropein is useful in compositions for promoting healing. Oleuropein is typically not employed in antiaging compositions, in that its effects tend to be incompatible with volumizing, but it can advantageously be employed in formulations for preconditioning the skin in advance of procedures as described herein (e.g., laser resurfacing, chemical peel, etc.).

Phosphatidyl Serine

In certain embodiments, phospholipids such as phosphatidylserine (PS), a highly enriched membrane phospholipid component, may be added. Phosphatidylserine has been known to have several physiological roles, such as activating signaling enzymes and antioxidant activity (see e.g. Draelos, Z., Pugliese, P. Glycation and Skin Aging: A Review. Cosmetics & Toiletries Magazine 2011; June 2011: 1-6; Lee, S., Yang, J., Park Y., et al. Protective effect and mechanism of phosphatidylserine in UVB-induced human dermal fibroblasts. European Journal of Lipid Science and Technology 2013; 115(7): 783-90; He, M., Kubo, H., Morimoto, K., et al. Receptor for advanced glycation end products binds to phosphatidylserine and assists in the clearance of apoptotic cells. EMBO reports 2011; 12(4): 358-64). It has been found to decrease MMP-1 in a dose dependent manner, to increase procollagen formation and may act as a substrate for AGE targets thus reducing the damage from glycation effects. Clearance of apoptotic cells is necessary for tissue development, homeostasis, and resolution of inflammation. Phosphatidylserine provides an "eat me" signal on the cell surface, and phagocytes recognize the signal using specific receptors such as the receptor of advanced glycation end-products (RAGE). This then binds to PS and assists in the clearance of apoptotic cells and end products of AGE. When phosphatidylserine is employed in a topical formulation, it is preferably present at from about 0.005% by weight or less to about 10.0% by weight or more, typically at from about 0.01% by weight to about 5.0% by weight, e.g., at from about 0.05% by weight to about 0.1% by weight.

Phosphatidylserine can advantageously be employed in formulations for preconditioning the skin in advance of procedures as described herein.

Carrier Systems

Liquids and gels containing the peptides and other components as described herein can be prepared using techniques as are known in the art of cosmetics manufacture. See, e.g., Handbook of Cosmetic Science and Technology, Fourth Edition, edited by André O. Barel, Marc Paye, Howard I. Maibach, CRC Press, 2014, the contents of which is hereby incorporated by reference in its entirety. Various formulations are possible. As an example, a clear cosmetic gel stick composition can include 60 to about 90% of an aliphatic polyhydric alcohol (e.g., a C2-6 alcohol containing from 2 to 6 hydroxyl groups); 1-10% of a soap; and 1-10% of a water-soluble emollient, e.g., a polyoxyalkylene ether of a C8-22 fatty alcohol, as the main ingredients, in combination with the peptides of the preferred embodiments. Aqueous extrudable gels are based on water-oil emulsion technologies. To minimize the amount of water introduced into an extrudable gel formula, the concentration of the active solution is adjusted. Ideally, a high concentration active solution (45-50%) of the peptides can be employed. Carrier systems for AP solids are typically based on volatile cyclic siloxanes because they evaporate quickly and do not leave residue on the skin. As an alternative to volatile cyclic siloxanes, alternatives can be used, including isohexadecane or C13-15 isoalkane. Solidification systems are employed to develop solid sticks that do not melt under typical storage or consumer conditions but provide an elegant skin feel and allow for easy transfer. A combination of cyclopentasiloxane and stearyl alcohol with varying degrees of additional waxes such as hydrogenated castor wax, hydrogenated vegetable oils and polyethylene, can be employed.

For liquid formulations (e.g., gel or lotion forms), a silicone, e.g., a cyclosiloxane or linear silicone (e.g., silicone elastomer), can be employed as a carrier. One type of suitable carrier is a dimethicone crosspolymer gel, e.g., dimethicone crosspolymer in cyclopentasiloxane. Other suitable dimethicone crosspolymers include cyclopentasiloxane, dimethicone/vinyldimethicone crosspolymer; dimethicone, dimethicone/vinyl dimethicone crosspolymer; and isodecane dimethicone/vinyl dimethicone crosspolymer.

Typically, the carrier is present in an amount of from about 80 wt. % to about 95 wt. %, or 82 wt. % to 92 wt. %, e.g., in a topical formulation for application to skin or mucous membranes.

Other Components

Penetration Enhancers

Fatty acids and alcohols can be employed to enhance penetration of the peptides, and to provide a silky feel to formulations, e.g., methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., $C_{6-12}$ fatty acids, or the like. Typical amounts when employed in topical formulations are from 1% by weight to 4% by weight. Other components can include anti-inflammatory agents, antioxidants, and solubility enhancers. For example, certain components of the formulation tend to be difficult to solubilize in conventional formulations. Phosphatidyl serine and oleuropein are known to exhibit solubility issues. In some embodiments, a siloxane polymer, e.g., caprylyl methicone, is used to solubilize phosphatidylserine. In some embodiments, caprylyl methicone is used to solubilize phosphatidylserine in anhydrous formulations. In some embodiments, panthenyl triacetate and naringenin is used to solubilize oleuropein. For topical compositions containing from about 0.05% by weight to about 0.1% by weight phosphatidyl serine and/or from about 0.05% by weight to about 0.1% by weight oleuropein, caprylyl methicone in an amount of from about 0.5% by weight to about 1% by weight of caprylyl methicone can solubilize phosphatidylserine in an anhydrous formulation.

Bentonite clays can be employed in conjunction with the peptides to provide impart penetration and adsorption properties to the compositions, and can aid in stabilizing emulsions. Other clays, such as hectorite and magnesium aluminum silicate can also be employed. Bentonite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total # carbons: # double bonds, $\Delta_{double\ bond\ positions}$ can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amidoamine quaternary cationic modifiers include palmitamidopropyltrimonium chloride cetearyl alcohol and palmitamidopropyltrimonium chloride.

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical administration comprise the peptide compositions as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide formulations, and also offer benefits in scar treatment, periwound protection and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth", "velvety" and "powdery". It can be modified by controlling the amount of liquid phase in the formula, and therefore the degree of swelling. Due to their film-forming properties, dimethicone crosspolymers can be used as delivery systems for active ingredients such as the peptides described herein, or other formulation components such as oil-soluble vitamins and sunscreens. Sunscreens such as octyl methoxycinnamate can be more efficiently delivered from a formulation containing a silicone elastomer, producing a higher sun protection factor (SPF). Silicone elastomer blends can be used to enhance SPF in oil-in-water formulations containing organic sunscreens. For example, in testing conducted regarding SPF, the addition of 4% silicone elastomer blend to a suncare formulation containing organic sunscreens increased the SPF from 5.7 to 18. This property of the silicone elastomer allows the effectiveness of sunscreen agents in a formulation to be maximized while reducing the amount needed to achieve a desired SPF. As a result, formulation costs can be reduced along with potential irritation caused by sunscreen actives. Accordingly, a higher SPF can be achieved with the same amount of UV absorber, resulting in enhanced performance with no added formulation cost. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a cross-linker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the topical preparations of the peptide compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. It is generally preferred to employ anhydrous compositions, as the presence of water can result in stinging upon administration to skin tissues subject to laser treatment, chemical peel, dermabrasion, or the like. Anhydrous formulations may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the formulations as described herein can be advantageously employed where it is desirable to minimize osmotic shock.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1, 3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing the peptide compositions as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the peptide compositions as described herein.

In some embodiments, liposomes are used to prepare one or more peptides. In some embodiments, the peptide is hexapeptide-11. In some embodiments, the peptide is functionalized with an acetyl group.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight.

The topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The peptide compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the peptide formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or nonaqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The peptide formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others. Preferably, compositions will have high spreadability and low viscosity properties. Compositions with such properties have been demonstrated to have an enhanced "silky" or "light" skin feel rating (see e.g. Bekker, M. Webber, G., Louw, N. Relating rheological measurements to primary and secondary skin feeling when mineral-based and Fischer-Tropsch wax-based cosmetic emulsions and jellies are applied to the skin, International Journal of Cosmetic Science 2013, 35(4), pp. 354-61).

Stability Testing

Stability testing of the topical formulations can be conducted as follows.

High temperature testing is now commonly used as a predictor of long-term stability. High temperature testing can be conducted at 37° C. (98 F) and 45° C. (113° F.). If a product is stored at 45° C. for three months (and exhibits acceptable stability) then it should be stable at room temperature for two years. A good control temperature is 4° C. (39° F.) where most products will exhibit excellent stability. Sometime, the product is also subjected to −10° C. (14° F.) for three months.

In some embodiments, the product pass three cycles of temperature testing from −10° C. (14° F.) to 25° C. (77° F.). The product is placed at −10° C. for 24 hours and place it at room temperature (25° C.) for 24 hours. This completes one cycle. If the product passes three cycles then you can have a good degree of confidence in the stability of the product. An even more rigorous test is a −10° C. to 45° C. five-cycle test. This puts emulsions under a tremendous stress and, if it passes the test, indicates that you have a highly stable product.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Kits for Non-Invasive Use and Use with Invasive Procedures

Some embodiments of the methods and compositions provided herein include kits comprising peptides provided herein. In some embodiments, kits can be provided to an administering physician, other health care professional, a patient, or a caregiver. In some embodiments, a kit comprises a container which contains the peptide compositions in a suitable topical formulation, and instructions for administering the peptide composition to a subject. The kit can optionally also contain one or more additional therapeutic or other agents. For example, a kit containing a peptide composition in topical form can be provided along with other skin care agents, such as, cleansers, occlusive moisturizers, penetrating moisturizers, sunscreens, sunblocks, and the like. The kit may contain the peptide composition in bulk form, or can contain separate doses of the peptide composition for serial or sequential administration. The kit can optionally contain one or more diagnostic tools, administration tools, and/or instructions for use. The kit can contain suitable delivery devices, such as, syringes, pump dispensers, single dose packets, and the like, along with instructions for administering the peptide compositions and any other therapeutic or beneficial agents. The kit can optionally contain instructions for storage, reconstitution (if applicable), and administration of any or all therapeutic or beneficial agents included. The kits can include a plurality of containers reflecting the number of administrations to be given to a subject, or the different products to be administered to the subject.

In some embodiments, the formulation is configured to support the skin before, during and after cosmetic procedures, and also works with the skin's own natural regenerating process and assists in improving the skin's appearance, and skin tightness. The topical formulation can be applied immediately post-procedure for faster recovery, or generally for healthier looking skin. The formulation can increase natural levels of elastin in the skin, improves the quality of existing elastin, stimulates increase in collagen production, and exhibits high antioxidant activity to reduce inflammation, redness and irritation. The topical formulation is suitable for all skin types and post-procedure skin. The topical formulations can be provided to the patient in bulk form, to permit a suitable amount of the peptides to be self-administered by the patient. For example, the patient can apply an amount of the formulation sufficient to provide an even coating over the affected area or as otherwise instructed by the physician. In certain embodiments it can desirable to incorporate additional therapeutic or active agents into the topical formulation. Alternatively, adjunct therapies or agents can be administered separately. For example, a cleanser, a sunblock, a sunscreen, a penetrating moisturizer, and/or an occlusive moisturizer can be provided for administration before or after the topical composition of the embodiments.

In one embodiment, a kit is provided for use in connection with an invasive skin procedure, as described herein. The kit, termed "an invasive kit", includes a topical peptide composition, an occlusive moisturizer, a gentle cleanser, a penetrating moisturizer, and a broad spectrum SPF 30+ sunscreen.

In another embodiment, a kit is provided for use in connection with improving skin health but not in connection with an invasive skin procedure. The kit, termed "a noninvasive kit," in some embodiments, includes a topical peptide composition, a gentle cleanser, a penetrating moisturizer, and a broad spectrum SPF 30+ sunscreen.

The various examples of creams, ointments, lotions, solutions, gels, sprays and patches may incorporate the peptide compositions as described herein as the active ingredient, in combination with penetration enhancing agents and other active agents acting synergistically on the skin for the promotion of wound healing or wound closure or the treatment of chronic cutaneous wound.

Examples

Example 1: Formulation

A topical formulation was prepared comprising a first peptide and a second peptide in combination with excipients. The formulation so prepared was evaluated for suitability for use as a topical formulation, including skin feel and stability, and was tested in vivo on a patient undergoing Coolsculpting. The formulation was prepared as in the following table.

TABLE 1

Formula 1

| Ingredient | Trade Name | Activity | % by wt. |
|---|---|---|---|
| Hydrogenated Lecithin, C12-16 Alcohols, Palmitic Acid | Biophilic H | Biophilic ™ H acts as a "second skin" and therefore helps to restore the cutaneous barrier of damaged skin. The emulsion made with Biophilic ™ H melts on the skin during the application and forms a restructuring film which reduces TEWL. | 2.254% |
| Avocado extract, Shea butter, Bentonite | Body 3-Complex | Tightening - elastase inhibition inhibits elastin breakdown, lipolysis, encourages some fat breakdown and turnover; aid in stretch mark alleviation | 1.000% |
| Acetyl Tetrapeptide-2 | Uplevity | LOXL1 (Lysyl oxidase like enzyme1 - cross links elastin components, tropoelastin) binds tropoelastin - TE builds elastin; FBLN5 (Fibulin 5-binds TE to Integrin to fibroblast stimulating fibroblast to produce elastin) | 2.000% |
| Phytoene/Phytofluene | IBR CLC Concentrate 0404 | Colorless carotenoids-anti-oxidative, anti-inflammatory, protect against UV and its damage, reduce inflammation, pigmentation and free radical damage as well as inhibit collagenase expression and therefore reduce collagen degradation | 0.500% |
| Hydroxymethoxyphenyl Decanone- | SymDecanox HA PN 972276 | Potent intrinsic hyaluronic acid booster, antioxidant and anti-irritant | 1.000% |
| TriHex-Palmitoyl Tripeptide-1 | Corum 8803 | Collagen, elastin stimulation, ECM recycling, anti-inflammatory | 3.000% |
| Hexapeptide-12 | Corum 8806 | Elastin binding protein, draws in newly produced elastin | 1.000% |
| Polyholosides from flax seeds | Sculptessence | Xylose, galactose, arabinose, rhamnose; Xylose, the main pentose included here is the first essential constituent of GAGs and consequently regulates their synthesis | 5.000% |
| *Plantago lanceolata* also called "Plantain" | Senestem | MicroRNAs inhibition, restarts the protein synthesis in order to prevent cellular senescence and extracellular matrix breakdown | 2.000% |
| Dill extract | LylastineV | Stimulates LOXL re-induction encouraging elastin formation | 1.000% |
| Phosphatidylserine | Lipoid PS P 70 | Lipid - MMP1 control, procollagen increase, stimulates HA production | 0.050% |
| Oleuropein | Oleuropein 80% | Anti-inflammatory but also stimulates UPS system and autophagy digesting worn out proteins in the cells, reversing cellular senescence | 0.020% |
| Hexapeptide-11 | Hexapeptide-11 | Potent stimulator of autophagy, promotes dose and time-dependent activation of proteasome, autophagy, chaperones and antioxidant responses from related genes | 0.010% |
| Hydrolyzed *Candida Saitoana* Extract | Celldetox | Stimulates autophagy, favors formation of lysosomes--purified alpha-glucan (oxidized proteins and peroxidized lipids) and blocks the accumulation of lipofuscin aggregates | 3.000% |
| Centella Asiatica | Actiphyte Gotu Lipo Kola | Hastens healing, stimulates collagen, fibronectin, prevents scarring | 1.000% |
| Propanediol Lecithin | Lucas Meyer Pro-LIPO Neo | Phospholipid Delivery vehicle for Hexapeptide-10 | 0.090% |
| Caffeine (and) Sodium salicylate (and) Lecithin (and) Silica | Lucas Meyer Isocell Slim | Vectorized Caffeine - potent lipolysis agent with targeted delivery | 1.000% |

Example 2: Coolsculpting Procedure

A patient underwent a Coolsculpting procedure on both sides of her abdomen. Immediately following the procedure, she applied the composition of Formula 1 to the left side abdomen only. Following the procedure, she continued to apply the composition of Formula 1 twice a day, morning and evening, to the same left side abdomen area. At four weeks, she started to observe that the loose skin on the lower left side abdomen was less noticeable and appeared more firm than that of the right side abdomen. This same observation was made through week 6 with the continued application of the composition of Formula 1 to the left side.

Example 3: Exemplary Formulations

Formulations suitable for use in skin tightening can be prepared having the following formulas.

TABLE 2

Exemplary Formula 1A

| Ingredient | % by wt. |
|---|---|
| Hydrogenated Lecithin, C12-16 Alcohols, Palmitic Acid | 1-4% |
| Avocado extract, Shea butter, Bentonite | 0.5-2% |
| Acetyl Tetrapeptide-2 | 1-4% |
| Phytoene/Phytofluene | 0.2-1% |
| Hydroxymethoxyphenyl Decanone- | 0.5-2% |
| TriHex-Palmitoyl Tripeptide-1 | 1-6% |
| Hexapeptide-12 | 0.25-4% |
| Polyholosides from flax seeds | 2.5-10% |
| *Plantago lanceolata* also called "Plantain" | 1-4% |
| Dill extract | 0.25-4% |
| Phosphatidylserine | 0.025-0.1% |
| Oleuropein | 0.01-0.05% |
| Hexapeptide-11 | 0.005-0.02% |
| Hydrolyzed *Candida Saitoana* Extract | 1-6% |
| *Centella Asiatica* | 0.25-4% |
| Propanediol Lecithin | 0.05-0.2% |
| Caffeine (and) Sodium salicylate (and) Lecithin (and) Silica | 0.25-4% |

TABLE 3

Exemplary Formula 1B(1)

| Ingredient | % by wt. |
|---|---|
| Acetyl Tetrapeptide-2 | 1-4% |
| TriHex - Palmitoyl Tripeptide-1 | 1-6% |
| Hexapeptide-12 | 0.5-2% |
| Phosphatidylserine | 0.025-0.1% |
| Oleuropein | 0.01-0.5% |
| Hexapeptide-11 | 0.005-0.02% |
| Other components | remainder |

TABLE 4

Exemplary Formula 1B(2)

| Ingredient | % by wt. |
|---|---|
| Acetyl Tetrapeptide-2 | 1-4% |
| TriHex - Palmitoyl Tripeptide-1 | 1-6% |
| Hexapeptide-12 | 0.5-2% |
| Hexapeptide-11 | 0.005-0.02% |
| Other components | remainder |

TABLE 5

Exemplary Formula 1C

| Ingredient | % by wt. |
|---|---|
| Phosphatidylserine | 0.025-0.1% |
| Oleuropein | 0.01-0.5% |
| Other components | remainder |

TABLE 6

Exemplary Formula 1D

| Ingredient | % by wt. |
|---|---|
| Acetyl Tetrapeptide-2 | 1-4% |
| TriHex - Palmitoyl Tripeptide-1 | 1-6% |
| Hexapeptide-12 | 0.5-2% |
| Phosphatidylserine | 0.025-0.1% |
| Oleuropein | 0.01-0.5% |
| Hexapeptide-11 | 0.005-0.02% |
| Caffeine (and) Sodium salicylate (and) Lecithin (and) Silica | 0.25-4% |
| Other components | remainder |

TABLE 7

Exemplary Formula 1E

| Ingredient | % by wt. |
|---|---|
| Hydrogenated Lecithin, C12-16 Alcohols, Palmitic Acid | 1-4% |
| Avocado extract, Shea butter, Bentonite | 0.5-2% |
| Phytoene/Phytofluene | 0.2-1% |
| Hydroxymethoxyphenyl Decanone- | 0.5-2% |
| Polyholosides from flax seeds | 2.5-10% |
| *Plantago lanceolata* also called "Plantain" | 1-4% |
| Dill extract | 0.25-4% |
| Phosphatidylserine | 0.025-0.1% |
| Oleuropein | 0.01-0.05% |
| Hydrolyzed *Candida Saitoana* Extract | 1-6% |
| Centella Asiatica | 0.25-4% |
| Propanediol Lecithin | 0.05-0.2% |
| Caffeine (and) Sodium salicylate (and) Lecithin (and) Silica | 0.25-4% |
| Other components | remainder |

TABLE 8

Exemplary Formula 1F

| Ingredient | % by wt. |
|---|---|
| TriHex-Palmitoyl Tripeptide-1 | 1-6% |
| Hexapeptide-12 | 0.5-2% |
| Hexapeptide-11 | 0.005-0.02% |
| Other components | remainder |

TABLE 9

Exemplary Formula 1G

| Ingredient | % by wt. |
|---|---|
| Acetyl Tetrapeptide-2 | 1-4% |
| Hexapeptide-12 | 0.5-2% |
| Hexapeptide-11 | 0.005-0.02% |
| Other components | remainder |

TABLE 10

Exemplary Formula 1H

| Ingredient | % by wt. |
|---|---|
| Acetyl Tetrapeptide-2 | 1-4% |
| TriHex-Palmitoyl Tripeptide-1 | 1-6% |
| Hexapeptide-12 | 0.5-2% |
| Other components | remainder |

TABLE 11

Exemplary Formula 1I

| Ingredient | % by wt. |
|---|---|
| Acetyl Tetrapeptide-2 | 1-4% |
| TriHex-Palmitoyl Tripeptide-1 | 1-6% |
| Hexapeptide-12 | 0.5-2% |
| Other components | remainder |

TABLE 12

Exemplary Formula 1J

| Ingredient | % by wt. |
|---|---|
| Acetyl Tetrapeptide-2 | 1-4% |
| TriHex-Palmitoyl Tripeptide-1 | 1-6% |
| Hexapeptide-12 | 0.5-2% |
| Hexapeptide-11 | 0.005-0.02% |
| Other components | remainder |

TABLE 13

Exemplary Formula 1K

| Ingredient | % by wt. |
|---|---|
| TriHex-Palmitoyl Tripeptide-1 | 1-6% |
| Hexapeptide-12 | 0.5-2% |
| Other components | remainder |

TABLE 14

Exemplary Formula 1L

| Ingredient | % by wt. |
|---|---|
| Ceramide NP | .05-.20% |
| *Tremella* | .50-2.0% |
| Niacinamide | 1-4% |
| Hydrogenated Lecithin, C12-16 Alcohols, Palmitic Acid | 1-6% |
| Avocado extract, Shea butter, Bentonite | 0.25-2% |
| Acetyl Tetrapeptide-2 | 1-4% |
| Phytoene/Phytofluene | 0.2-1% |
| Hydroxymethoxyphenyl Decanone- | 0.5-2% |
| TriHex-Palmitoyl Tripeptide-1 | 1-6% |
| Palmitoyl Hexapeptide-12 | 1-6% |
| Polyholosides from flax seeds | 2.5-10% |
| *Plantago lanceolata* also called "Plantain" | 1-4% |
| Dill extract | 0.25-4% |
| Phosphatidylserine | 0.025-0.1% |
| Oleuropein | 0.01-0.05% |

TABLE 15

Exemplary Formula 1M

| Ingredient | % by wt. |
|---|---|
| Hydrogenated Lecithin, C12-16 Alcohols, Palmitic Acid | 1-6% |
| Avocado extract, Shea butter, Bentonite | 0.25-2% |
| Acetyl Tetrapeptide-2 | 1-4% |
| Phytoene/Phytofluene | 0.2-1% |
| Hydroxymethoxyphenyl Decanone- | 0.5-2% |
| TriHex-Palmitoyl Tripeptide-1 | 1-6% |
| Palmitoyl Hexapeptide-12 | 0.25-4% |
| Polyholosides from flax seeds | 2.5-10% |
| *Plantago lanceolata* also called "Plantain" | 1-4% |
| Dill extract | 0.25-4% |
| Phosphatidylserine | 0.025-0.1% |
| Oleuropein | 0.01-0.05% |
| Hexapeptide-11 | 0.005-0.02% |
| Hydrolyzed *Candida Saitoana* Extract | 1-6% |
| *Centella Asiatica* | 0.25-4% |
| Propanediol, Lecithin | 0.25-2% |
| *Euglena Gracilis* Extract, Aqua, Caffeine, *Glaucium Flavum* Leaf Extract | 0.05-1% |

Example 4: Gene Expression Following Hexapeptide-11 Treatment

Gene expression in fibroblasts were measured following 72 hours of exposure to hexapeptide-11.

Dermal Fibroblasts were plated in cell culture media and allowed to grow to approximately 85-90% confluency following manufacturer's guidelines. Cells were harvested and plated at 10,000 cells per $cm^2$ in 6-well dishes cultured for 3 days. On the third day, confluency was estimated by microscopy and the cell culture media was replaced. The cells were treated with hexpapeptide-11 at a 100× concentration or control buffer without peptide. The time at initial exposure to the peptide is considered time, t=0. Treated and untreated control cells were harvested, counted and extracted for RNA at 24 hours, 48 hours, and 72 hours following t=0. Cell pellets and isolated RNA were stored at −80° C. until analysis by quantitative-PCR.

The 72-hour time point RNA samples (treated and untreated) were used for gene expression analysis. RNA was converted to first strand cDNA and analyzed by quantitative-PCR. Tables 16A-16B show the gene expression data.

TABLE 16A

Gene expression data (positive fold change)

| Gene | Fold Change | |
|---|---|---|
| AMBRA1 | 3.59 | AMBRA is major activating molecule in the autophagy signaling network. Autophagy ensures the removal of toxic compounds, as well as of damaged or redundant molecules. In the past few years, Ambra1 has emerged as a scaffold molecule that serves as a platform for autophagy-related complexes and as an early autophagy regulator, |
| ATG4A | 3.29 | This gene encodes a member of the autophagic protein family. |
| PSMB5 | 2.56 | Proteasome subunit beta type-5 is known as 20S proteasome subunit beta-5 is a protein that in humans is encoded by the PSMB5 gene |
| CASP3 | 2.24 | Caspase-3 is a predominant player in the execution of apoptotic cell death. However, recent studies indicated that capase-3 plays a role in autophagic processes - favors the extracellular export of autophagic vacuoles |

TABLE 16A-continued

Gene expression data (positive fold change)

| Gene | Fold Change | |
|---|---|---|
| ATG5 | 2.00 | Atg5 has been previously characterized as a protein specifically required for autophagy, and also has pro-apoptotic properties |

TABLE 16B

Gene expression data (negative fold change)

| Gene | Fold Change | |
|---|---|---|
| COL5A2 | −65.65 | Secretion of type IV, type V, and type VI collagen subunits peaked during the middle stage of adipose differentiation. |
| MAPK14 | −83.67 | Activation of MAPK14 impairs autophagosome-lysosome fusion and, thus, autophagy |
| TNF | −92.41 | Our results demonstrated that at subtoxic levels, TNF was able to impair autophagy |
| SOD3 | −101.59 | Decrease ROS, decrease cell apoptosis, inhibition SOD3 increases apoptosis - |
| PDGFRA | −369.65 | Inhibition of platelet-derived growth factor signaling induces autophagy in a multitude of cells |
| IGF1 | −901.80 | High IGF-I levels lead to reduced autophagy. |

The data shows a definite and significant relationship between hexapeptide-11 and autophagy.

Example 5: Hexapeptide-11 Treatment on Macrophage Clustering

The effects of hexapeptide-11 treatment on macrophage clustering were determined.

3T3-L1 adipocytes were untreated or treated with TNF-alpha (~25 nM) for 24 hours. One set of TNF-alpha treated adipocytes was also treated with hexapeptide-11 (0.1 mg/mL). One set of J774 macrophages was treated with hexapeptide-11 (0.1 mg/mL) for 24 hours. The macrophages were added to the adipocytes. After an 1 hour incubation, the cells were placed on ice and incubated with a fluorescently labeled Cholera toxin B subunit to label the cell surface of macrophages a fluorescent green. The cells were then fixed with 4% formaldehyde for 15 minutes and then incubated with LipidTox to label the lipid droplets within the adipocytes a fluorescent red color. Four conditions were performed: (1) J774 macrophages with untreated adipocytes; (2) J774 macrophages with TNF-alpha treated adipocytes; (3) J774 macrophages with TNF alpha treated adipocytes plus hexapeptide-11 in the 1 hour incubation of both cell types; and (4) peptide pretreated J774 macrophages with hexapeptide-11 pretreated TNF-alpha treated adipocytes incubated together in the presence of hexapeptide-11. Images taken with a 60× objective were analyzed by counting the number of macrophages associated with ~100 adipocytes for each condition.

Figure 4:
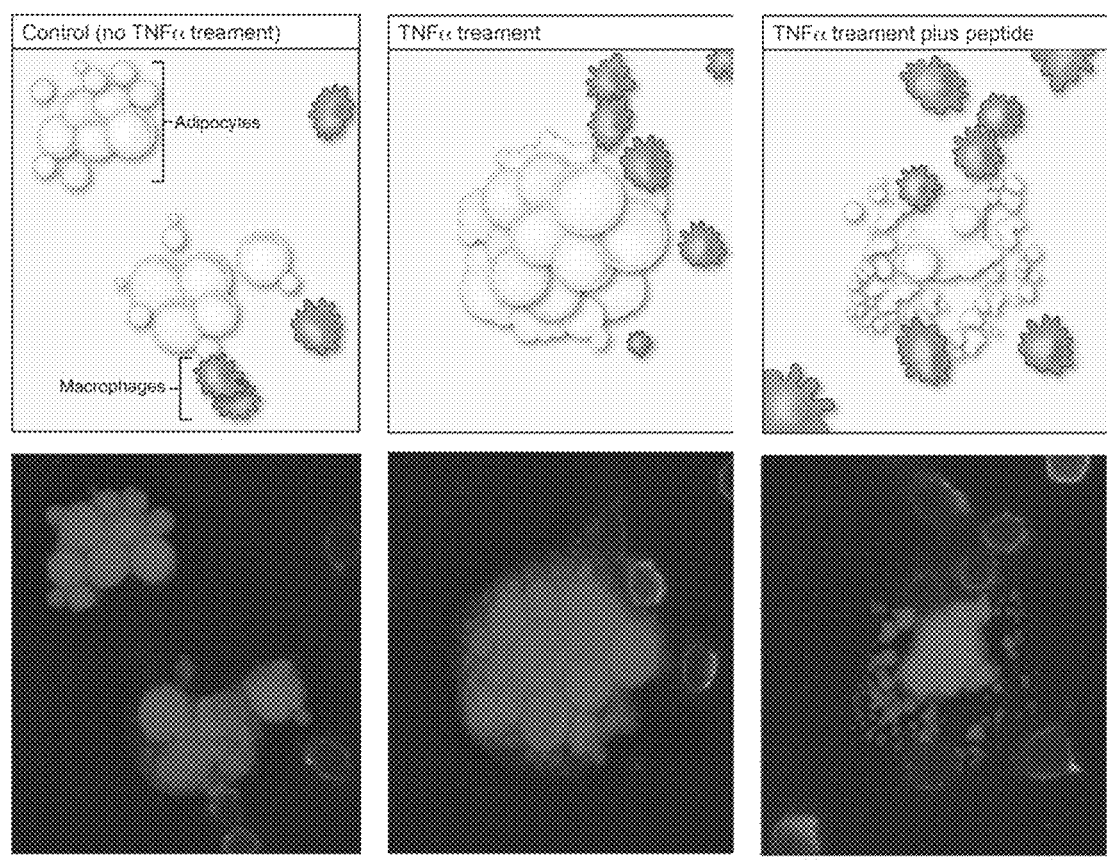
FIG. 4 illustrates images of macrophage clustering. The panel on the left illustrates free-floating co-cultured adipocytes and macrophages. The panel in the middle illustrates addition of TNF-alpha on adipocyte droplet breakdown and macrophage clustering. The panel on the right illustrates peptide addition on adipocyte droplet breakdown and macrophage clustering.

FIG. 4 shows images of adipocytes and macrophages. The left panel shows free floating co-cultured adipocytes and macrophages with no TNF-alpha treatment (Control). The middle panel shows that the addition of TNF-alpha results in early adipocyte breakdown and macrophage clustering. The right panel shows that TNF-alpha and peptide treatments results in further adipocyte droplet breakdown and significant macrophage clustering.

Figure 5A:
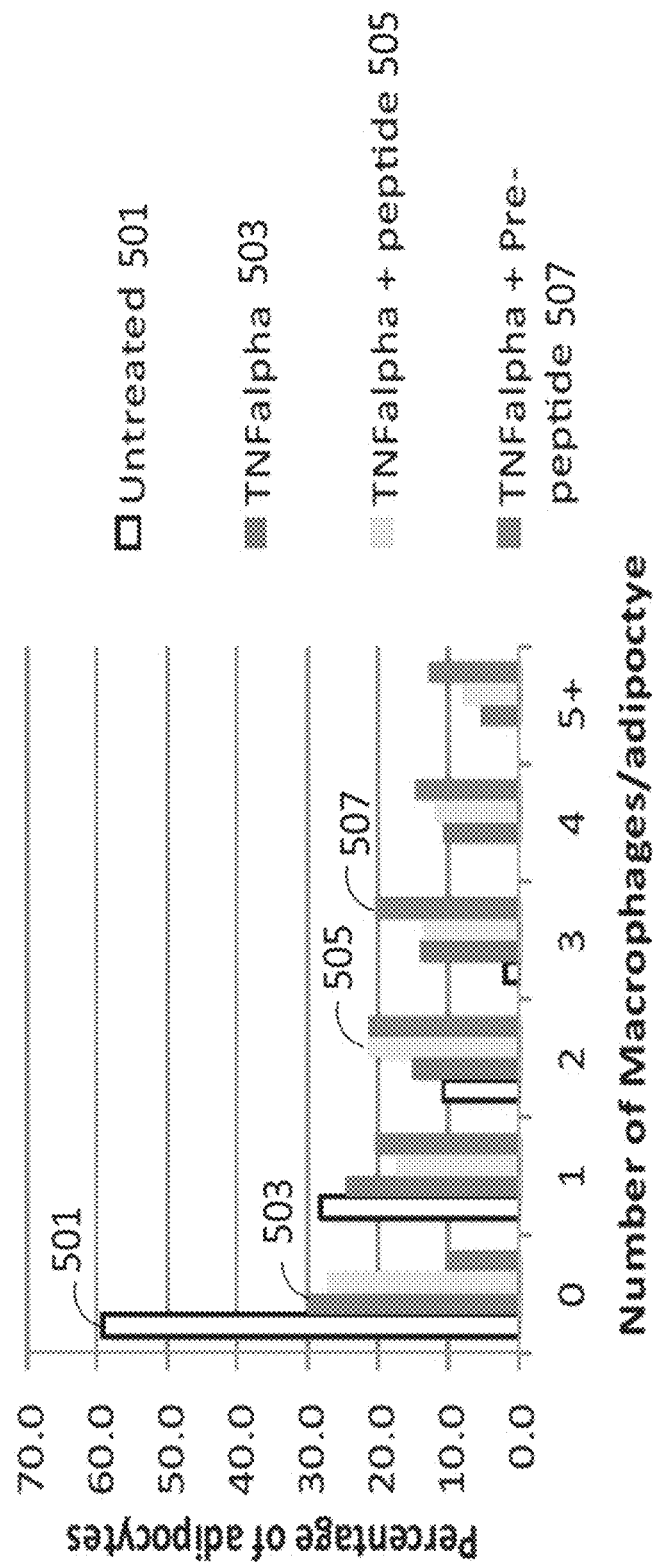
FIG. 5A illustrates number of macrophages when adipocytes were untreated (white bars, first bar from the left of the group of bars 501), treated with TNF-alpha (red bars, second bar from the left of the group of bars 503), treated with TNF-alpha and peptide (blue bars, third bard from the left of the group of bars 505), and pre-treated with peptide followed by TNF-alpha treatment (darker blue bars, fourth bar from the left of the group of bars 507).
Figure 5B:
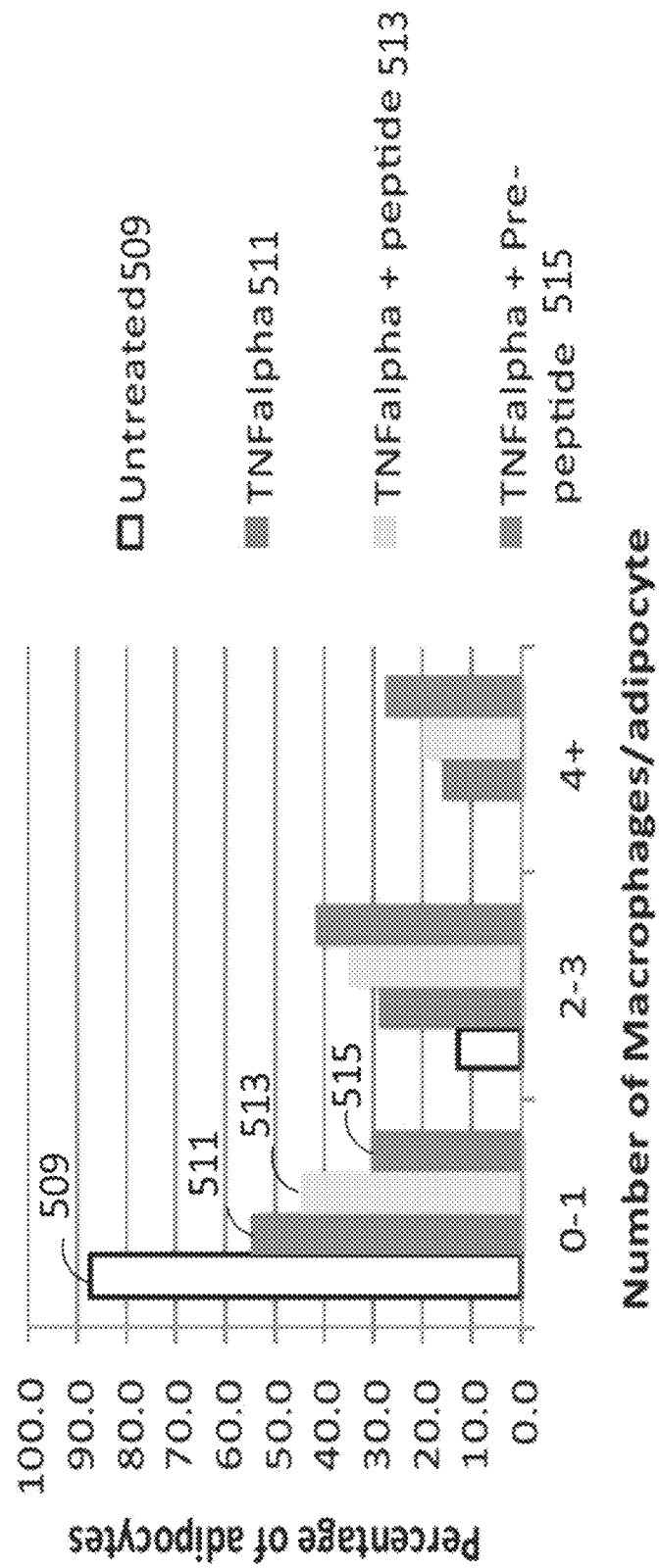
FIGS. 5B-5C illustrate data of FIG. 5A with number of macrophage/adipocyte grouped together.
Figure 5C:
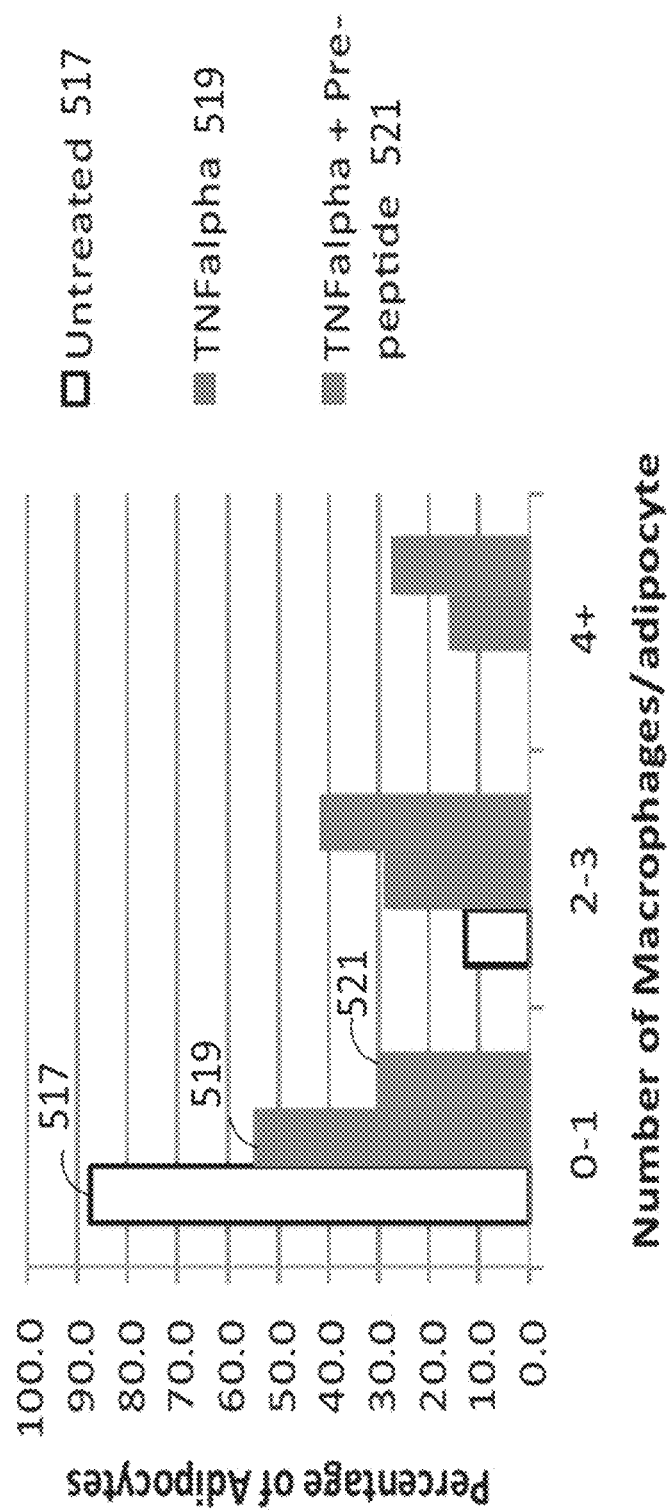

FIG. 5A shows the number of adipocytes with either 0, 1, 2, 3, 4, and 5+ associated macrophages expressed as a percentage of the total number of adipocytes counted (~100 adipocytes/condition). When adipocytes were untreated (white bars, first bar from the left of the group of bars 501) no adipocytes were found to have greater than 3 macrophages associated with them and the majority had no macrophages. TNF-alpha treatment greatly increased the number of macrophages associated with adipocytes (red bars, second bar from the left of the group of bars 503). Peptide treatment increased the number of macrophages associated with adipocytes (blue bars, third bard from the left of the group of bars 505), including those with cells that were pre-treated with peptide (darker blue bars, fourth bar from the left of the group of bars 507). FIGS. 5B-5C show the data as FIG. 5A with the number of macrophage/adipocyte grouped together. FIG. 5B shows adipocytes untreated (white bars, first bar from the left of the group of bars 509), TNF-alpha treatment (red bars, second bar from the left of the group of bars 511), peptide and TNF-alpha treatment (blue bars, third bar from the left of the group of bars 513), and cells pre-treated with peptide followed by TNF-alpha treatment (darker blue bars, fourth bar from the left of the group of bars 515). FIG. 5C shows adipocytes untreated (white bars, first bar from the left of the group of bars 517), TNF-alpha treatment (red bars, second bar from the left of the group of bars 519), and cells pre-treated with peptide followed by TNF-alpha treatment (blue bars, third bar from the left of the group of bars 521).

The data shows that hexapeptide-11 treatment increase macrophage clustering.

Example 6: A Double Blind Randomized Controlled Trial, Evaluating the Efficacy and Tolerability of the Regenerating Body Complex in Combination with Cryolipolysis Procedures Ten subjects participated in the trial. Eligible subjects included women between 25 and 65 years of age with clearly visible bilateral subcutaneous arm fat appearing as a distinct bulge of fat in the arm at least 14 cm from the elbow with soft, pliable tissue of sufficient volume for treatment on both sides. Subjects with previous fat reduction procedures or implants in or near the treatment area, previous surgery in the arms, and any contra-indication to device usage, as decided by the physician, relating to existing diseases or drug use were excluded from participating in the study. Subjects with excessive laxity were also excluded. Pregnant or lactating subjects were excluded and subjects planning on becoming pregnant during the study duration.

Subjects underwent treatment of cryolipolysis of the upper arms using the CoolSculpting System (ZELTIQ Aesthetics, Pleasanton, Calif.). Each subject received two −11° C., 35-minute cooling cycle to each arm delivered using the COOLPETITE Advantage™ cups. The cups were placed on two separate positions on each posterior arm (4×35-minute sessions) per the standard process. Immediately following the cessation of the treatment on each arm, a timed 3 minute (+/−1 minute) manual massage of moderate intensity was performed. The right arm received treatment first. The topical regenerating body complex product (Exemplary Formula 1M) was used to treat one arm twice a day. The comparator lotion was used to treat the other arm twice a day. Assessments on the subjects were taken at 4, 8, and 12 weeks. Study efficacy assessments included blinded investigator assessment and photography, subject satisfaction and improvement, evaluation of contour improvement over time and skin tightness, tone and texture, and evaluation of Canfield photography for quantitative assessments. Skin laxity was also measured according to the grading scale of Table 17.

TABLE 17

Skin Laxity Grading Scale

| Score | Classification | Description |
|---|---|---|
| 0 | None | No loose skin, toned and firm skin with smooth skin surface texture |
| 1 | Mild | Mildly loose skin, somewhat toned with smooth skin surface texture |
| 2 | Moderate | Moderately loose skin, no deep tone, few wrinkles and crepiness on the skin surface |
| 3 | Severe | Very loose skin without underlying tone, multiple wrinkles and crepiness on skin surface, skin distinct from underlying subcutaneous tissue via palpation |
| 4 | Extreme | Prominent redundancy of skin without underlying tone, severe wrinkling, and crepiness on skin surface |

Figure 6A:
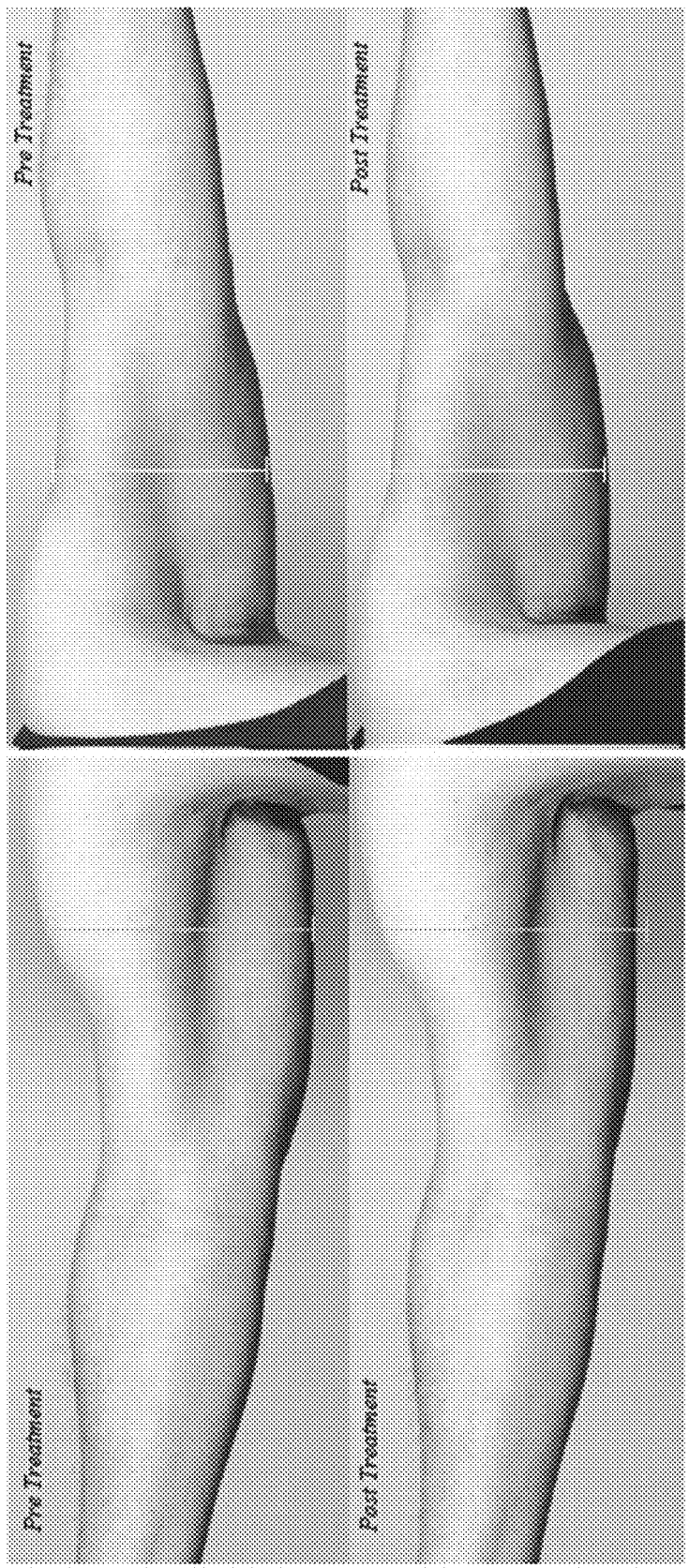
FIGS. 6A-6C illustrate images of arms pre- and post-treatment using topical regenerating body complex product.
Figure 6B:
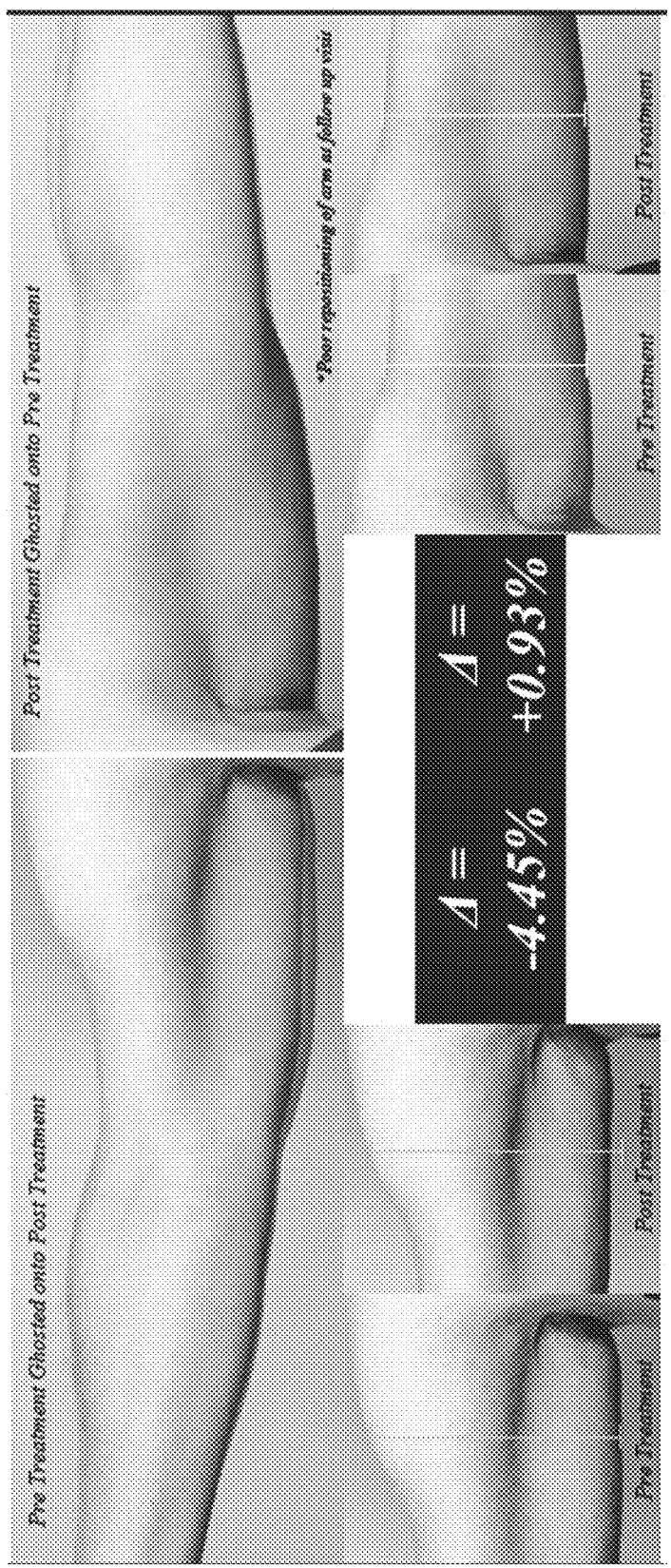
Figure 6C:
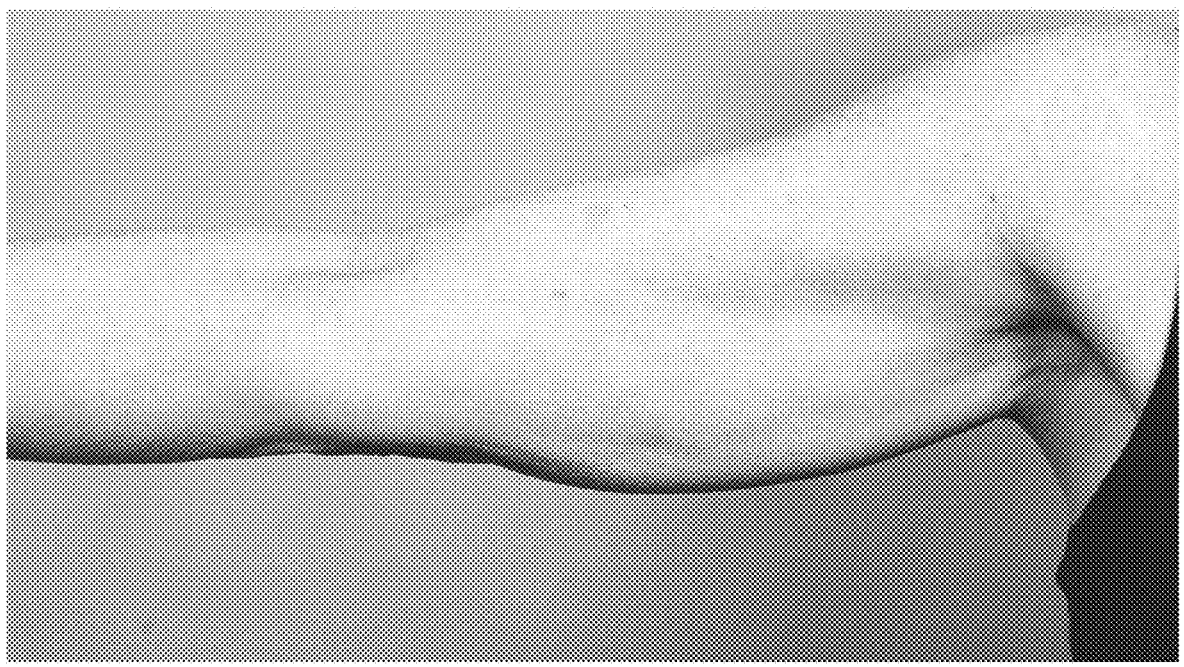

FIGS. 6A-6C show images of arms following 1 month of treatment.

The data shows improvement in skin laxity following treatment.

Example 7. Improvements in Skin Laxity in the Neck

The effects of Exemplary Formula 1L as described in Table 14 were tested for improvements in skin laxity in the neck.

Exemplary Formula 1L was topically applied twice daily for 12 weeks to the auricular region of a female aged 52 years old. Biopsy Hematoxylin and Eosin (H&E) and Verhoeff-Van Gieson (VVG) stains were taken.

Figure 7A:
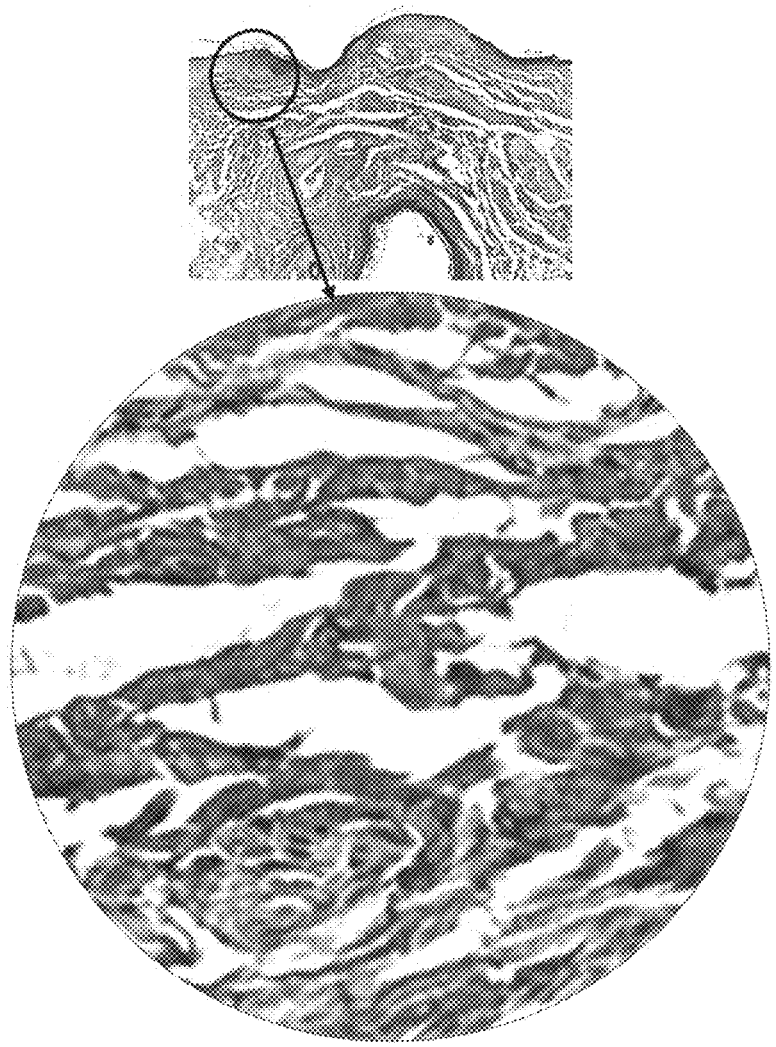
FIG. 7A shows a VVG stain at baseline at 10× magnification and a zoomed-in image.
Figure 7B:
FIG. 7B shows a VVG stain after 12 weeks of application of Exemplary Formula 1L at 10× magnification and a zoomed-in image.

FIG. 7A shows a VVG stain at baseline at 10× magnification and a zoomed-in image. More clumped old elastin fibers (thin black stains) and few healthy elastin fibers (few thin black stains) were observed. FIG. 7B shows a VVG stain after 12 weeks of application of Exemplary Formula 1L at 10× magnification and a zoomed-in image. After 12 weeks, there were more thin black fibers, indicating healthier elastin fibers, and well distributed thin black fibers all over the dermis.

Figure 7C:
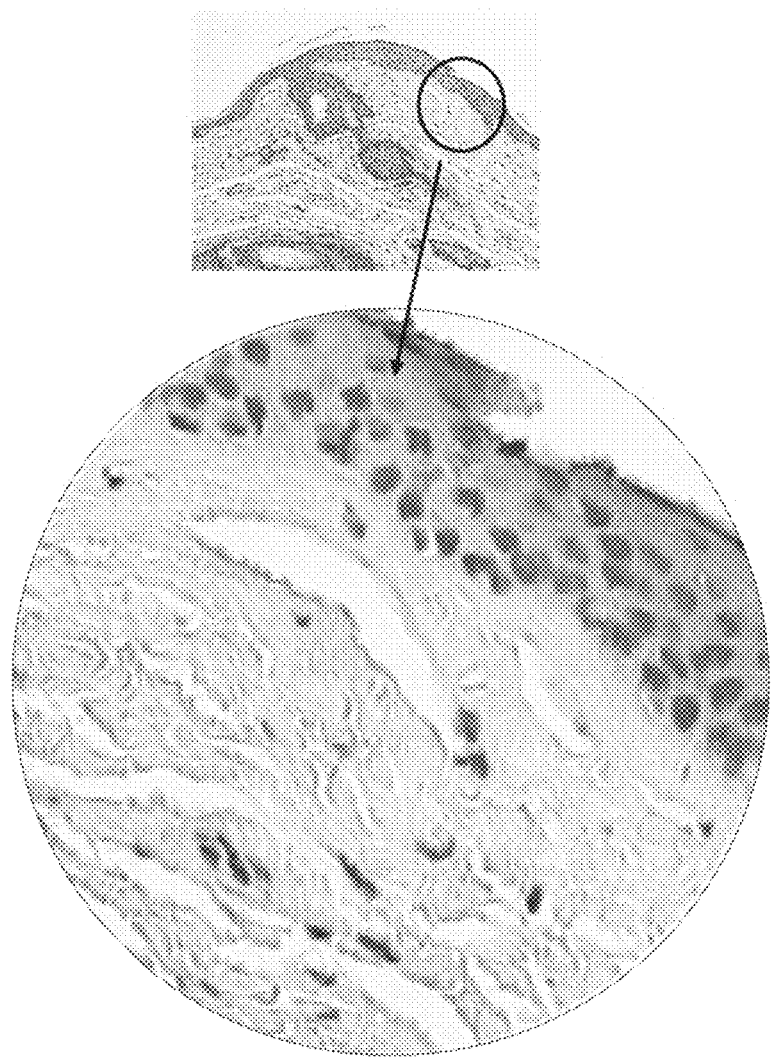
FIG. 7C shows an H&E stain at baseline at 20× magnification and a zoomed-in image.
Figure 7D:
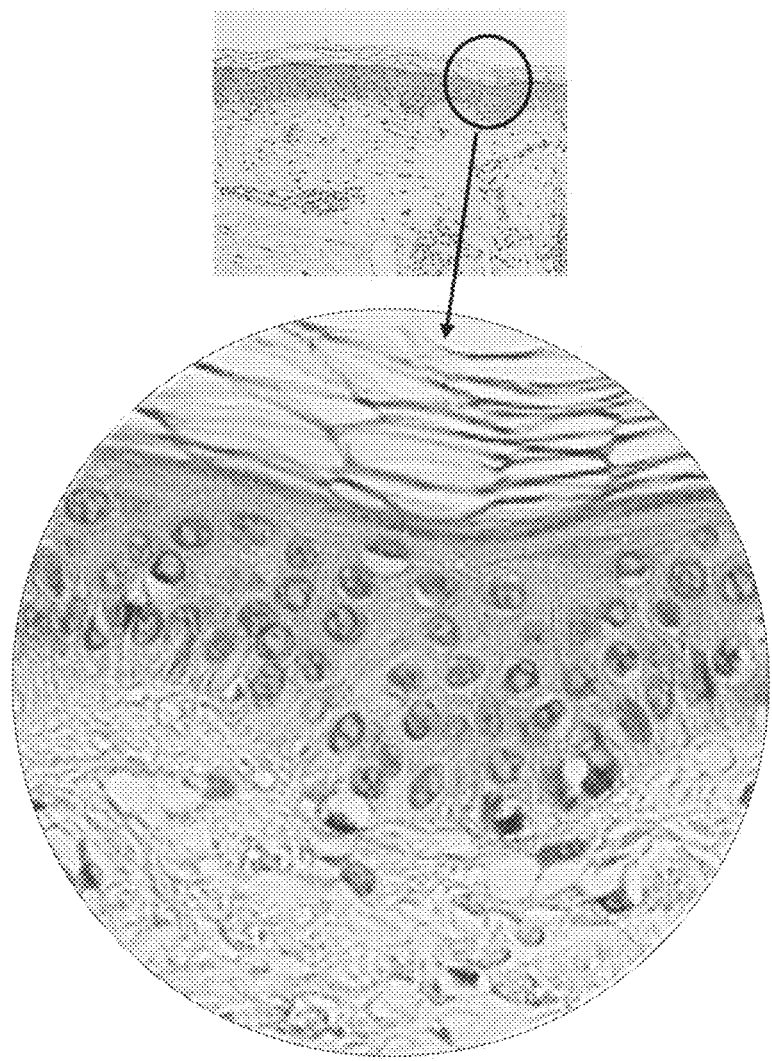
FIG. 7D shows an H&E stain after twelve weeks of application of Exemplary Formula 1L at 20× magnification and a zoomed-in image.

FIG. 7C shows an H&E stain at baseline at 20× magnification and a zoomed-in image. Flattened, more inactive basal cells were observed. FIG. 7D shows an H&E stain after 12 weeks of application of Exemplary Formula 1L at 20× magnification and a zoomed-in image. As seen in FIG. 7D, there were more layers of keratinocytes (thicker epidermis), healthier thickened cornified keratin layer (basket-weave layer) to support reduced epidermal water loss, and healthier rete ridges and basal stem cells at dermo-epidermal junction.

The data shows new, healthy and well distributed elastin fibers as well as improved epidermal health and functioning as a result of treatment of Exemplary Formula 1L.

Example 8. Improvements in Texture and Wrinkles in the Neck

The effects of a treatment regimen comprising Exemplary Formula 1L as described in Table 14 were tested.

Figure 8A:
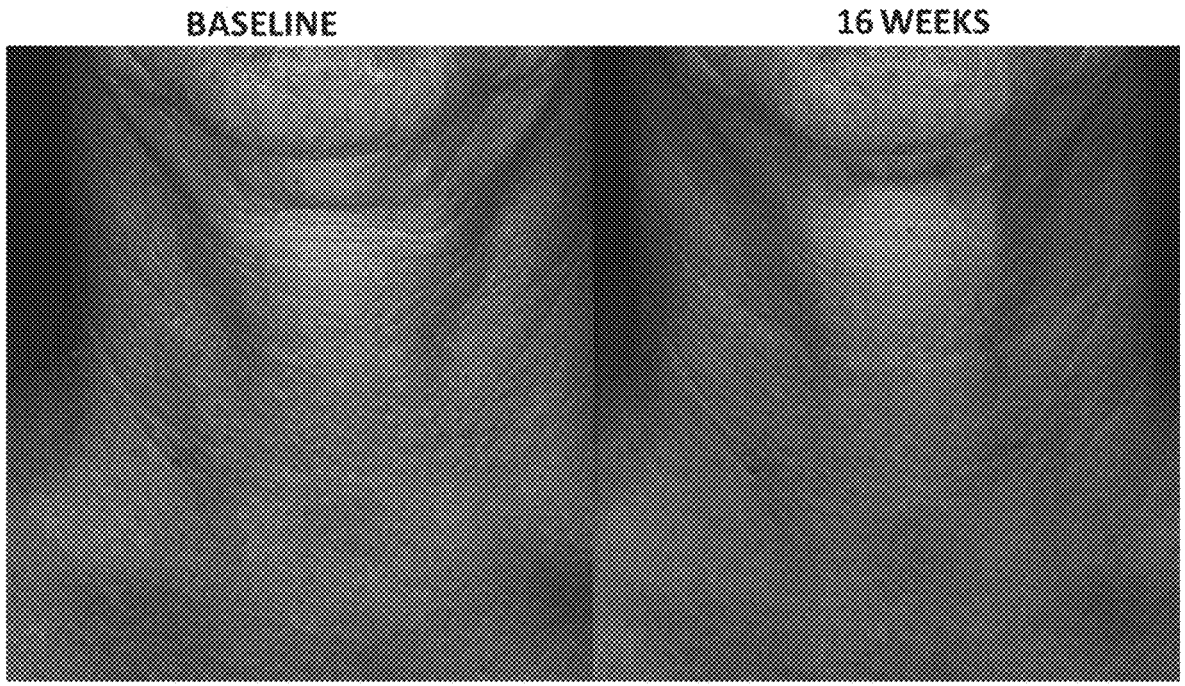
FIG. 8A shows images of a neck of a first female subject following a treatment regimen at baseline and following 16 weeks of treatment.
Figure 8B:
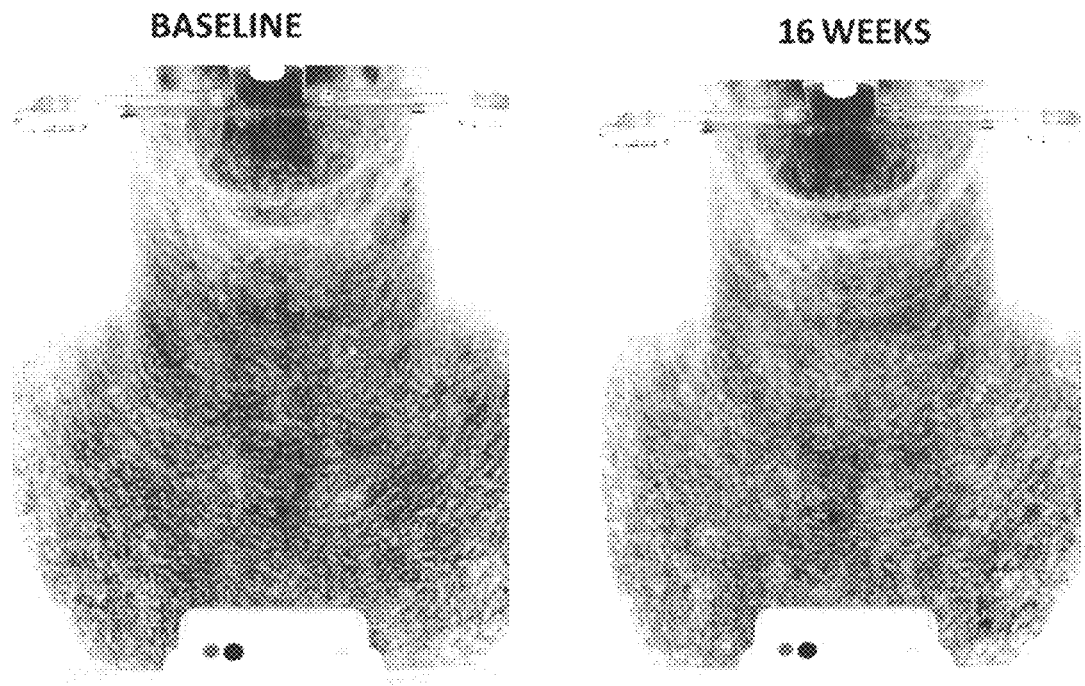
FIG. 8B shows images of a neck using a red channel of a first female subject following a treatment regimen at baseline and following 16 weeks of treatment.
Figure 8C:
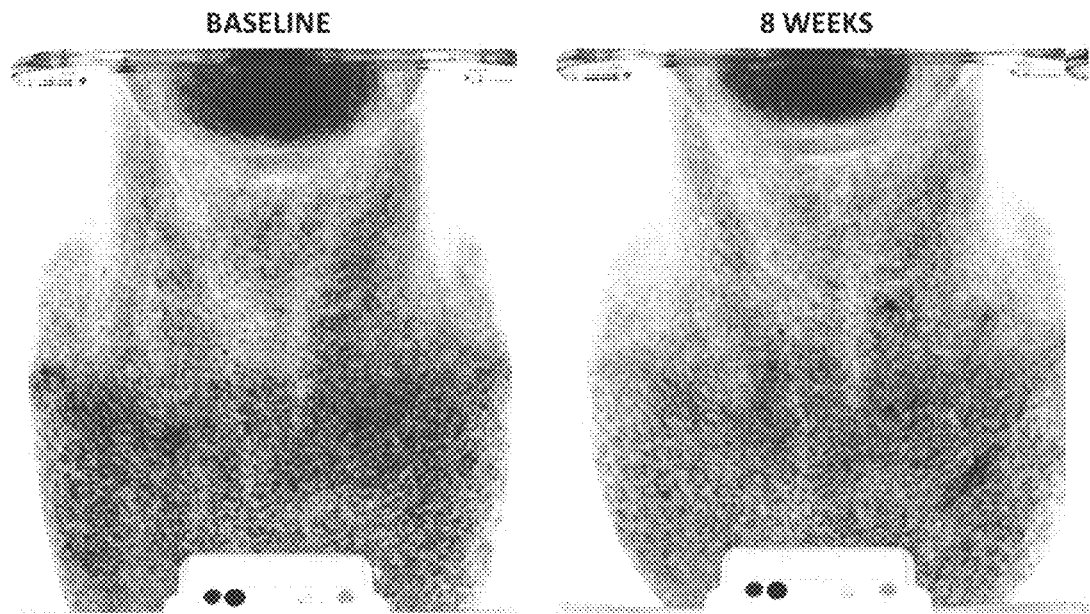
FIG. 8C shows images of a neck using a red channel of a first female subject at baseline and following 8 weeks of treatment.
Figure 8D:
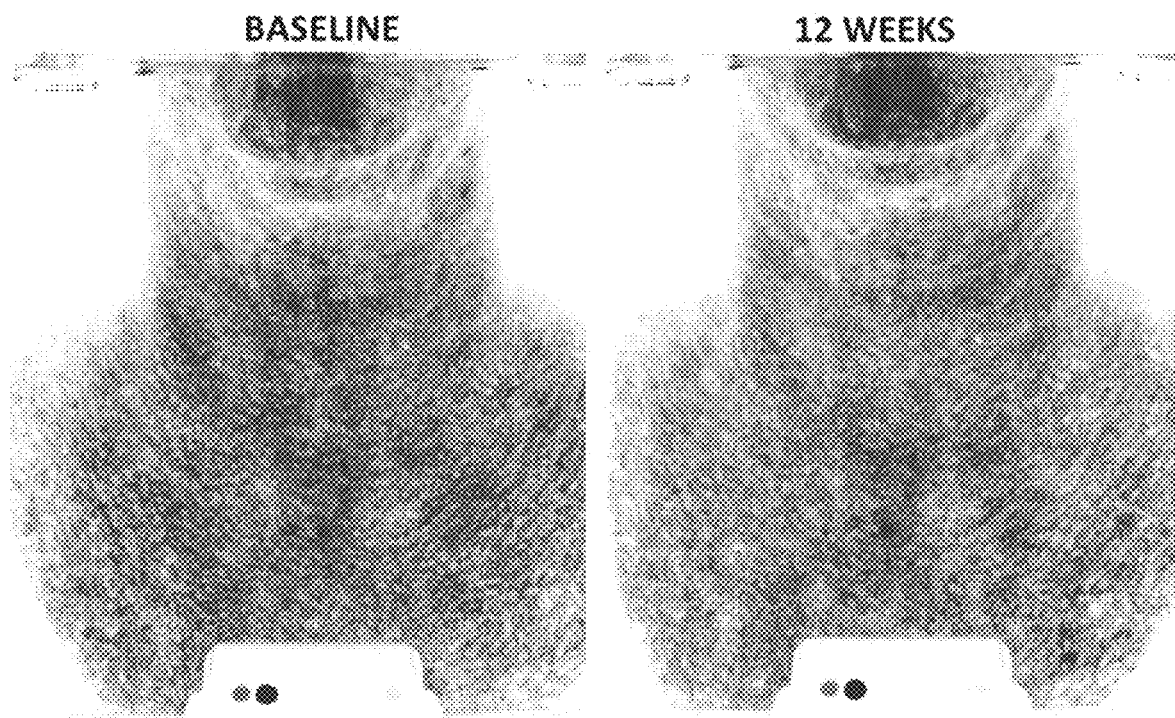
FIG. 8D shows images of a neck using a red channel of a first female subject at baseline and following 12 weeks of treatment.

FIGS. 8A-8B show the effects of the treatment regimen as applied to a first female subject aged 53. The treatment regimen included a gentle cleanser applied in the morning and evening, Exemplary Formula 1L applied in the morning and evening, and a broad spectrum sunscreen SPF 30 applied in the morning. As seen in FIGS. 8A-8B, there was a 44% reduction in wrinkles on the neck, 22% improvement in overall texture on the neck, and 59% improvement in red channel as compared to baseline versus the treatment regimen for sixteen weeks. FIG. 8C shows images of the female subject after 8 weeks of treatment. FIG. 8D shows images of the female subject after 12 weeks of treatment. At 12 weeks of treatment, there was a 62% reduction in redness on the neck and a 51% reduction in redness on the chest.

Figure 9:
FIG. 9 shows images of a neck of a second female subject at baseline and following 16 weeks of treatment.

FIG. 9 shows the effects of the treatment regimen as applied to a second female subject aged 45. The treatment regimen included a gentle cleanser applied in the morning and evening, Exemplary Formula 1L applied in the morning and evening, and a broad spectrum sunscreen SPF 30 applied in the morning. As seen in FIG. 9, there was a 38% reduction in the redness on the chest.

Figure 10:
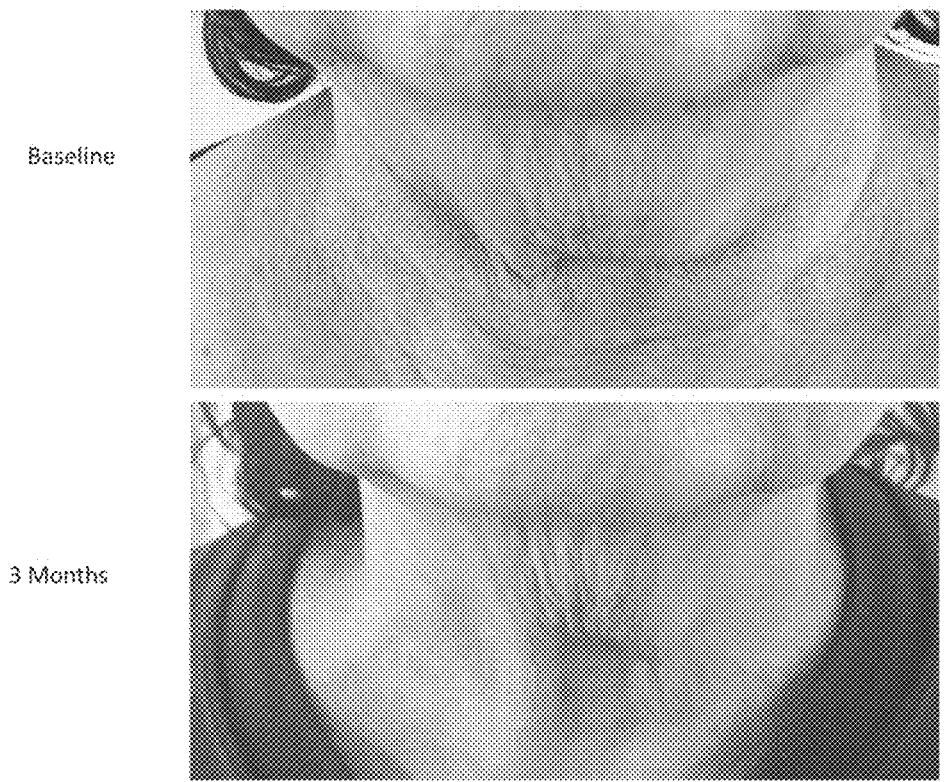
FIG. 10 shows images of a neck of a third female subject at baseline and following 3 months of treatment.

A third female subject aged 67 applied Exemplary Formula 1L twice a day. FIG. 10 shows the effects of the treatment regimen as applied to a third female subject aged 67.

The data shows that a treatment regimen comprising Exemplary Formula 1L improves the overall texture of the neck and reduces wrinkles.

Example 9: Liposome Delivery System for Hexapeptide-11

Hexapeptide-11 was formulated in a liposome for topical delivery.

Figure 11:
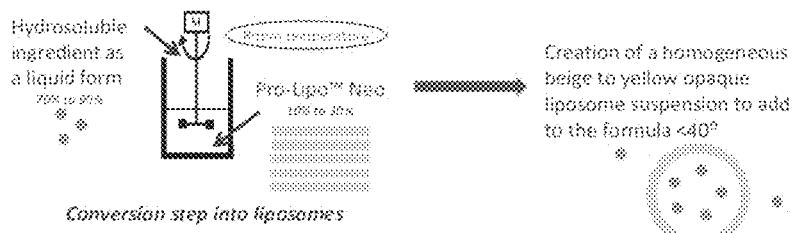
FIG. 11 shows a schematic for preparation of liposomes.
Figure 11:
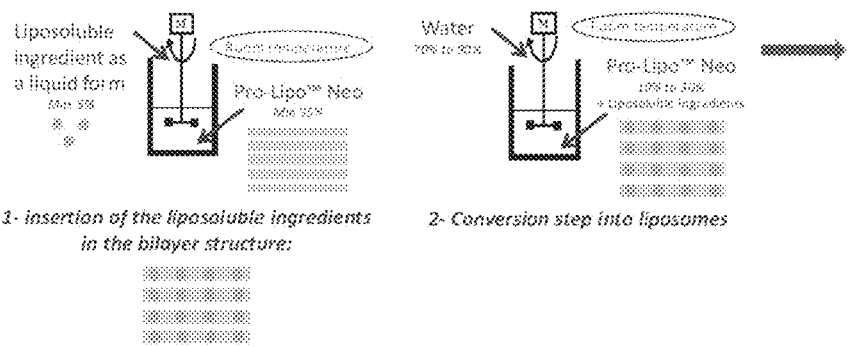
Figure 11:
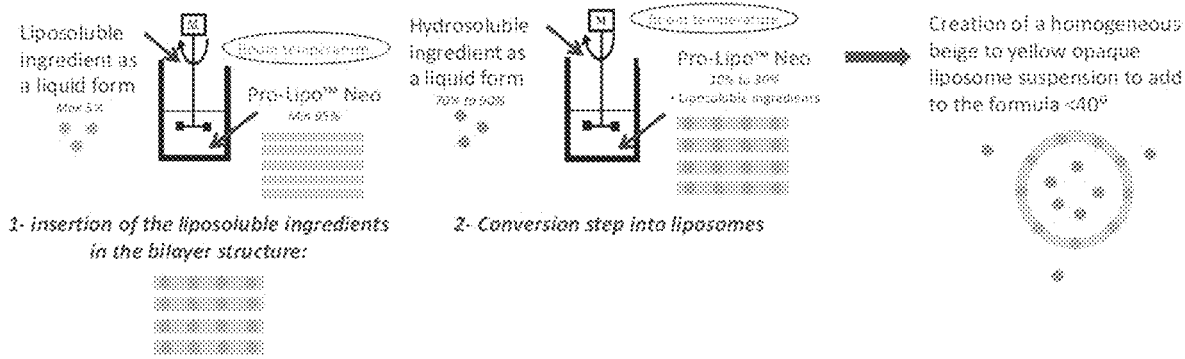
Figure 12:
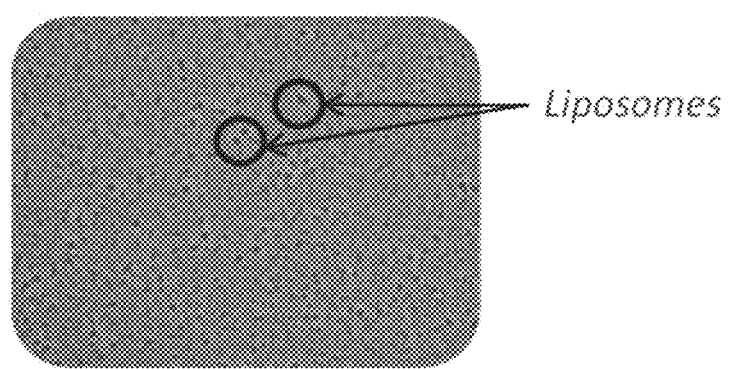
FIG. 12 shows an image of a liposome.

A water suspension of liposomes was prepared with 300 ppm (0.03%) of hexapeptide-11 and 27% Pro-Lipo™ Neo. A schematic as seen in FIG. 11 shows the various methods for creating liposomes including hydrosoluble ingredient entrapment, liposoluble ingredient entrapment, and a Liposoluble and Hydrosoluble ingredient entrapment. Liposomes were observed following the liposome suspension process manufacturing as seen in FIG. 12. An average particle size of the formulation comprising hexapeptide-11 encapsulated in a liposome was between about 185 nm.

Example 10: Imaging Techniques

Figure 13:
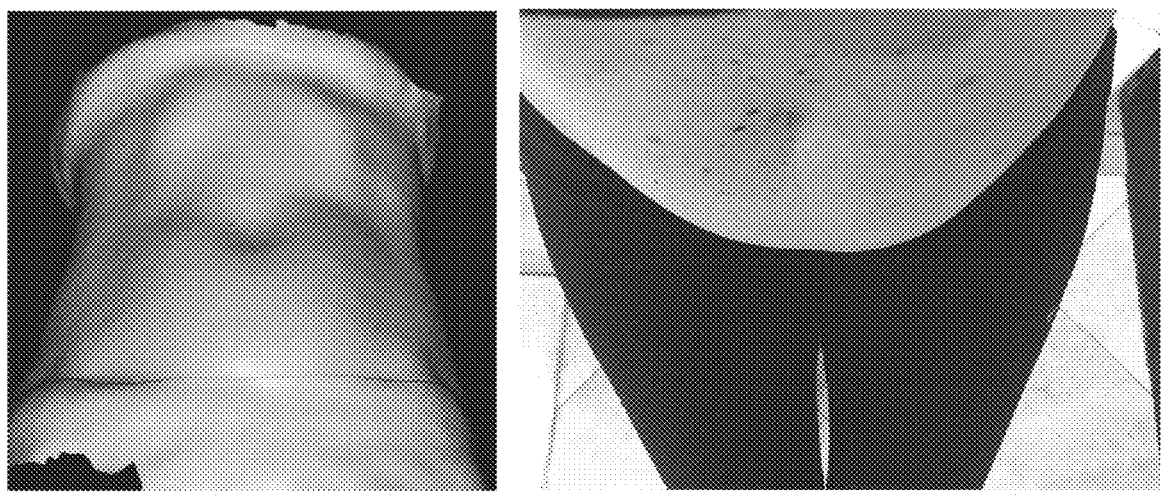
FIG. 13 shows images taken using imaging techniques as described herein.
Figure 14A:
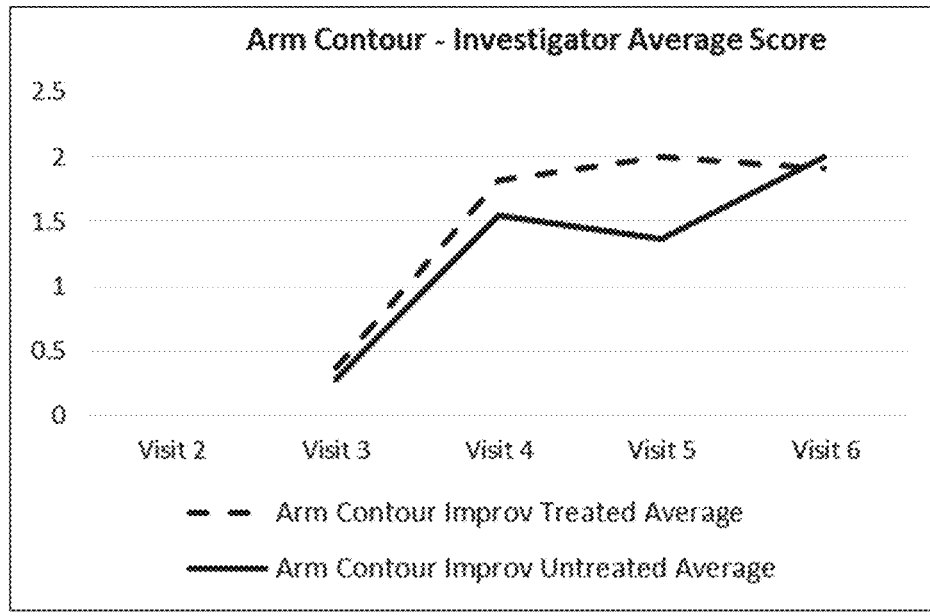
FIGS. 14A-14D show graphs of arm contour and arm shape of subjects that underwent cryolipolysis and treated with regenerating body complex and control.
Figure 14B:
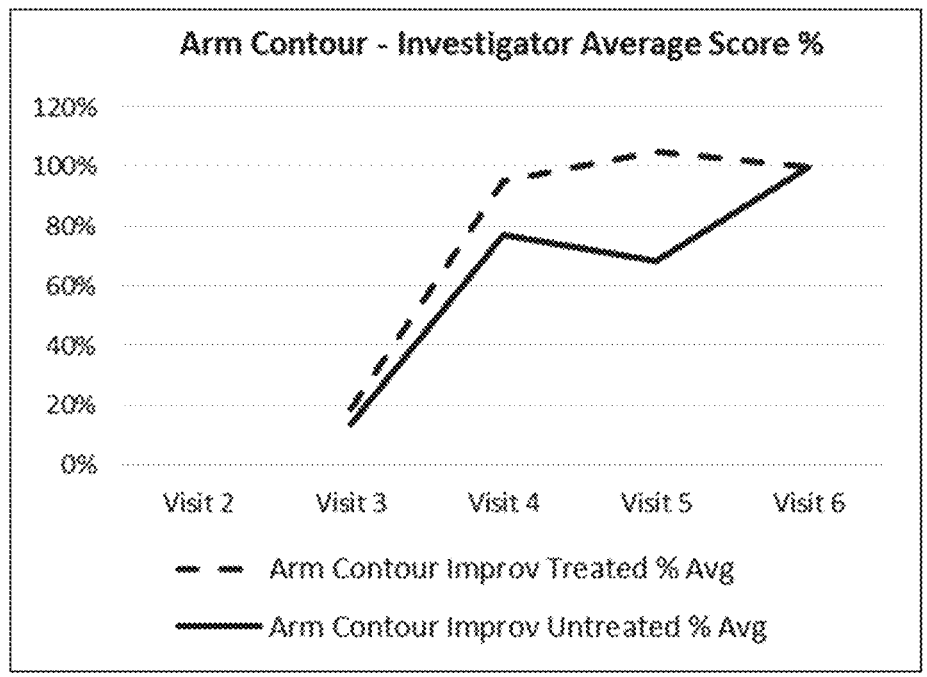
Figure 14C:
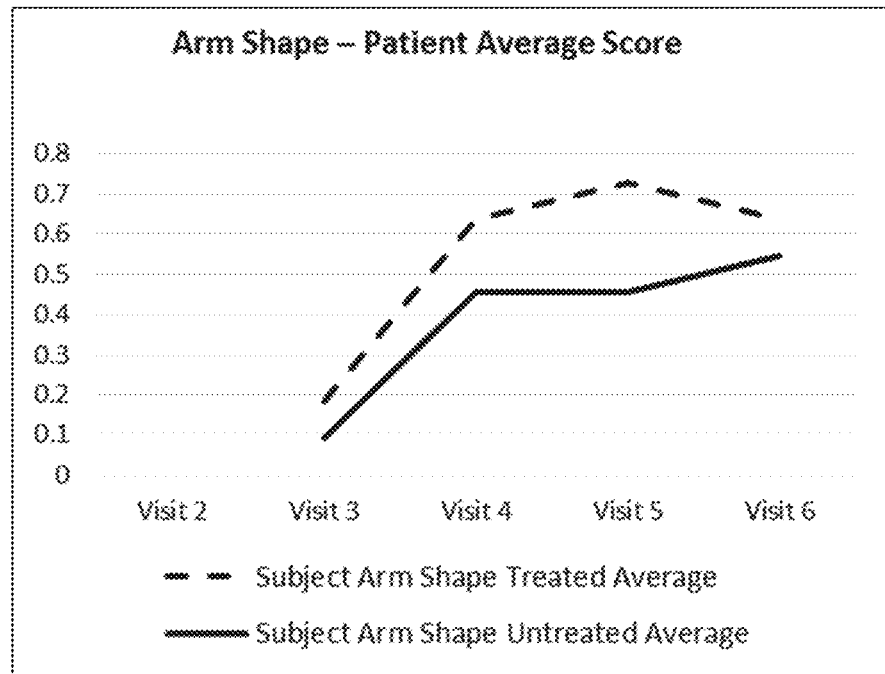
Figure 14D:
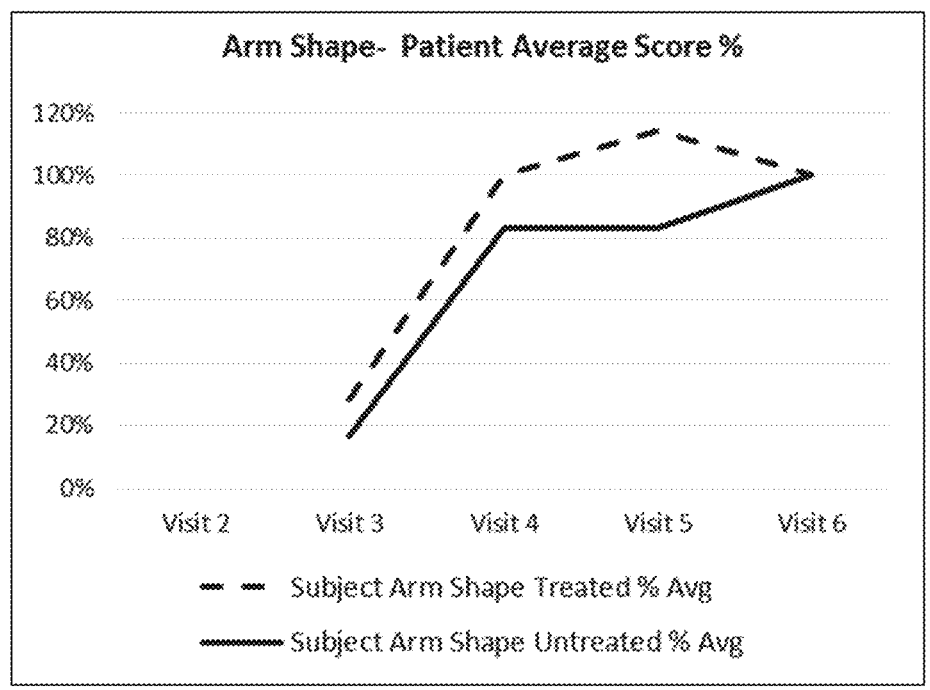

Various imaging techniques were used to assay improvements in skin laxity as seen in FIG. 13.

Example 11: A Second Double Blind Randomized Controlled Trial, Evaluating the Efficacy and Tolerability of the Regenerating Body Complex in Combination with Cryolipolysis Procedures A randomized, double-blind, comparator controlled study was performed to assess the efficacy of the regenerating body complex (RBC) (Exemplary Formula 1M) compared to a bland moisturizer (Cetaphil lotion) in combination with fat reducing device cryolipolysis of the upper arm area. Five (05) subjects were randomized to receive the RBC on one arm and the comparator (Cetaphil lotion) on the other arm. Subjects had a screening, baseline/treatment visit and follow-up visits at 1, 4, 8 and 12 weeks post treatment visit. Subjects underwent cryolipolysis treatment to the upper arms on treatment visit (Day 0). Subjects were instructed to apply the blinded study cream to the assigned treatment area starting the evening of the treatment visit and twice daily throughout the entire study. Study efficacy assessments included blinded Investigator assessment and photography. Subject satisfaction and improvement were also assessed.

Study Population

Up to five (5) evaluable subjects participated in this pilot study. Eligible subjects were women between 25 and 65 years of age with clearly visible bilateral subcutaneous arm fat appearing as a distinct bulge of fat in the arm at least 14 cm from the elbow, with soft, pliable tissue of sufficient volume for treatment on both sides. Subjects with previous fat reduction procedures or implants in or near the treatment area, previous surgery in the arms, and any contra-indication to device usage, as decided by the physician, relating to existing diseases or drug use were excluded from participating in the study. Subjects with excessive laxity were also excluded. Pregnant or lactating subjects were excluded, as will subjects planning on becoming pregnant during the study duration. Subjects will be instructed to avoid starting a major diet or exercise program and maintain a constant weight (within 5% of baseline measure).

Materials and Methods

Procedure

Subjects underwent treatment of cryolipolysis of the upper arms using the CoolSculpting System (ZELTIQ Aesthetics, Pleasanton, Calif.). Each subject received two −11° C., 35-minute cooling cycle to each arm delivered using the COOLPETITE Advantage™ cups. The cups were placed on two separate positions on each posterior arm (4×35-minute sessions) per the site's standard process. Immediately following the cessation of the treatment on each arm, a timed 3 minute (+/−1 minute) manual massage of moderate intensity was performed. The right arm always received treatment first.

Study Topical Products

Topical products included regenerating body complex: Applied twice daily; and Comparator: Cetaphil lotion (bland OTC moisturizer). The topical products were provided in a double-blind fashion with tubes labeled A and B. Treatment assignments were blinded. Subjects were provided with one tube of Product A and one tube of Product B at the treatment visit. Additional supplies were provided if needed at future visits. Arm assignment was randomized, and subjects were instructed to apply Product A to the right upper arm and Product B to the left upper arm twice daily for the entire study duration.

Study Assessments

Photography

Standardized photography was performed at the Screening, Baseline/Treatment Visit (pre- and post-procedure), and at each of the Follow-up visits (1, 4, 8, and 12 weeks). Photos captured anterior, posterior (horizontal plane/90 degrees); and additional posterior view with the wrist at the same level of shoulder, pointing forward and elbow bent at 90 degrees. Canfield Mirror Software was used to ensure consistency in arm placement and possible analysis through ghosting and Canfield. Analysis may be performed by Canfield and/or ghosting to assess changes from baseline in tone, texture, wrinkling and total skin surface area. Other assessments may also be performed.

Investigator Assessments

The Blinded Investigator was asked to assess skin laxity at all visits and contour improvement at all follow-up visits. Assessments in skin laxity were performed by assessing the subject during the visit. Assessments in contour improvement were performed by reviewing Baseline photos compared to the study visit photos.

Subject Assessments

Subjects were asked to assess the skin laxity at all visits and improvement in the shape of their arm at all follow-up visits. Subjects completed a Global Assessment of Skin Quality at study end.

Circumference

Circumference measurements were performed at every visit and were done using one designated tape measure. They were always taken at a consistent distance from an anatomical landmark, for example, the distance from olecranon process. All measurements were done by the same investigator to avoid possible inter observer variation.

Study Visits

Subjects underwent six total visits: Screening, Treatment Visit (Day 0) and Follow-up Visits at 1, 4, 8 and 12 weeks post treatment. At the Baseline/Treatment visit, the subject was randomized to which arm will receive the regenerating body complex (RBC) or comparator. The site was provided with blinded kits. Kits were dispensed in sequential order with the lowest kit available. Subjects were instructed to apply the assigned product Labeled A to the right treatment area and product Labeled B to the left treatment area twice daily.

Standardized photos were taken at each visit. At Day 0, photos were captured pre-treatment and 15 minutes (+/−5 minutes) post procedure.

A blinded Investigator completed the Skin Laxity Assessment questionnaire (Table 18) at all study visits and the Post Procedure Contour Improvement questions (Table 19) at all follow-up visits. The Subject completed the Skin Laxity Assessment questionnaire at all study visits and the Post Procedure Improvement in their Arm Shape (Table 20) at all follow-up visits. In addition, subjects completed a Global Assessment of Skin Quality (Table 21) at the final study visit (Week 12/EOS).

TABLE 18

Skin Laxity Grading Scale

| Score | Classification | Description |
| --- | --- | --- |
| 0 | None | No loose skin, toned and firm skin with smooth skin surface texture |
| 1 | Mild | Mildly loose skin, somewhat toned with smooth skin surface texture |
| 2 | Moderate | Moderately loose skin, no deep tone, few wrinkles and crepiness on the skin surface |
| 3 | Severe | Very loose skin without underlying tone, multiple wrinkles and crepiness on skin surface, skin distinct from underlying subcutaneous tissue via palpation |
| 4 | Extreme | Prominent redundancy of skin without underlying tone, severe wrinkling, and crepiness on skin surface |

TABLE 19

Post Procedure Contour Improvement

| | NONE | SMALL | MODERATE | SIGNIFICANT |
| --- | --- | --- | --- | --- |
| OVERALL CONTOUR IMPROVEMENT | | | | |
| Right | 0 | 1 2 3 | 4 5 6 | 7 8 9 |
| Left | | | | |

TABLE 20

Arm Shape Improvement

| Improved the OVERALL Shape of my arm | STRONGLY AGREE | AGREE | NEUTRAL | DISAGREE | STRONGLY DISAGREE |
|---|---|---|---|---|---|
| Right | | | | | |
| Left | | | | | |

TABLE 21

Global Assessment of Skin Quality

| | Pick the side that you feel best answers the question. | RIGHT | LEFT | No Difference |
|---|---|---|---|---|
| 1 | I believe there is more overall improvement in the condition of my skin on this arm. | | | |
| 3 | Decreased my crepey skin faster on _____ side | | | |
| 4 | Increased my skin tightness faster on _____ side | | | |
| 5 | I feel more confident with the way the _____ arm looks | | | |
| 6 | I prefer using this skincare product over the other | | | |
| 7 | I would recommend this skincare product to others over the other product | | | |

Study Period

The study period included several visits as described below.

Visit 1 Screening Visit (Day −17 to −1): A prospective subject was examined to determine if they qualify for entry into the study. This initial examination included the following: obtain photographic release and standardized photograph.

Visit 2 Baseline/Treatment Visit (Day 0): This follow-up visit included standardized photograph (Baseline); assign next available kit; blinded investigator and subject questionnaires pre-treatment; circumference; perform CoolSculpting followed by 3-minute massage (Right first); standardized photograph (15+/−5 minutes); and review take home product application instructions sheet/application diary.

Visit 3 (Week 1): This follow-up visit included subject and blinded investigator assessments; circumference; standardized photograph; and review subject post-procedure home instructions/application diary.

Visit 4 (Week 4): This follow-up visit included subject and blinded investigator assessments; circumference; standardized photograph; and review subject post-procedure home instructions/application diary.

Visit 5 (Week 8): This follow-up visit included subject and blinded investigator assessments; circumference; standardized photograph; and review subject post-procedure home instructions/application diary.

The schedule of events summarizing the visits is seen in Table 22.

TABLE 22

Schedule of Events

| Procedures | Visit 1 Screening Day −17 to −1 | Visit 2 Txt 1 Day 0 Pre | Visit 2 Txt 1 Day 0 Post | Visit 3 Post Treatment Week 1 | Visit 4 Post Treatment Week 4 | Visit 5 Post Treatment Week 8 | Visit 6 EOS Week 12 |
|---|---|---|---|---|---|---|---|
| Photo Release | X | | | | | | |
| Review study eligibility | X | X | | | | | |
| Randomize subjects to treatment side (Alastin RBC or Cetaphil Lotion) | | X | | | | | |
| Review diary for completeness and compliance | | | | X | X | X | X |
| Investigator Skin Laxity Assessment | | X | | X | X | X | X |
| Subject Skin Laxity Assessment | | X | | X | X | X | X |
| Subject Global Aesthetic Improvement of Skin Quality | | | | | | | X |
| CoolSculpting | | | X | | | | |
| Standardized Photograph | X | X | X | X | X | X | X |
| Apply Topical Product (Product A and B) | | | X | | | | |
| Circumference | | X | | X | X | X | X |
| Investigator Contour Improvement Questionnaire | | | | X | X | X | X |
| Subject's Arm Shape Improvement Questionnaire | | | | X | X | X | X |
| Weigh dispensed and returned randomized topical product (Product A and B) and dispense new product as applicable. | | | X | X | X | X | X |
| Review home Post-procedure Instructions sheet/Dairy | | | X | X | X | X | |

Example 12. Results from Clinical Studies

Following clinical trials similar to those described Examples 6 and 11, various measurements were taken.

Arm contour and arm shape was measured in patients who underwent cryolipolysis and treated with regenerating body complex (Exemplary Formula 1M) or control. Arm contour and arm shape was measured at various patient visits including Visit 3: Week 1 Follow Up; Visit 4: Week 4 Follow Up; Visit 5: Week 8 Follow Up; and Visit 6: Week 12 Follow Up, Final Visit. Data was not used from Visit 1 (Visit 1: Screening Visit). Visit 2 is baseline/treatment. Data can be seen in FIGS. 14A-14D. As seen in FIGS. 14A-14D, efficacy was highest as Visit 5, which is 8 weeks following cryolipolysis.

Figure 15A:
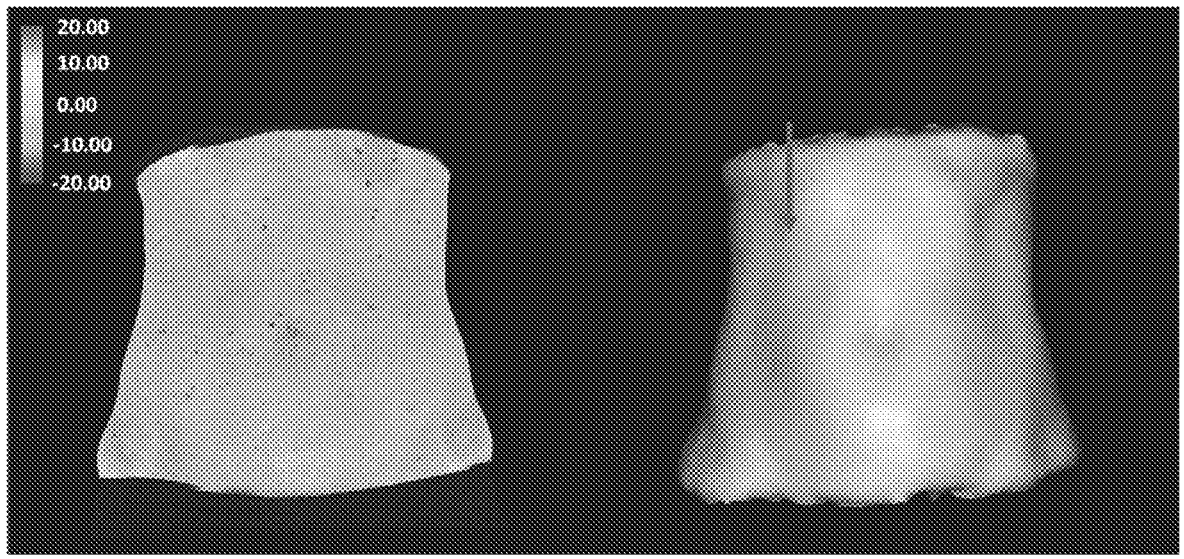
FIGS. 15A-15C show images of an abdomen of a patient treated with radiofrequency followed by regenerating body complex.
Figure 15B:
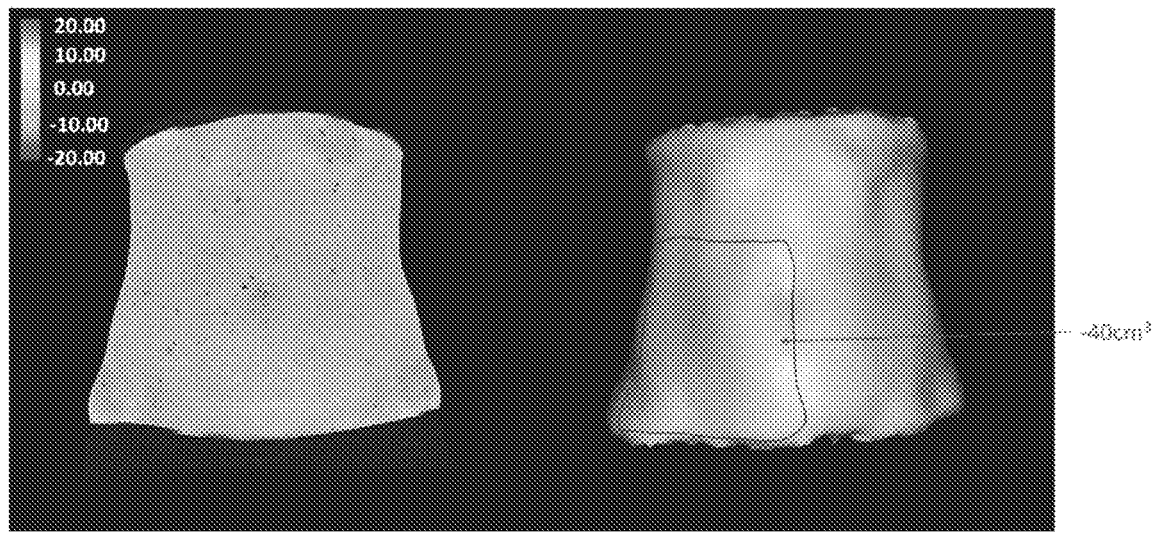
Figure 15C:
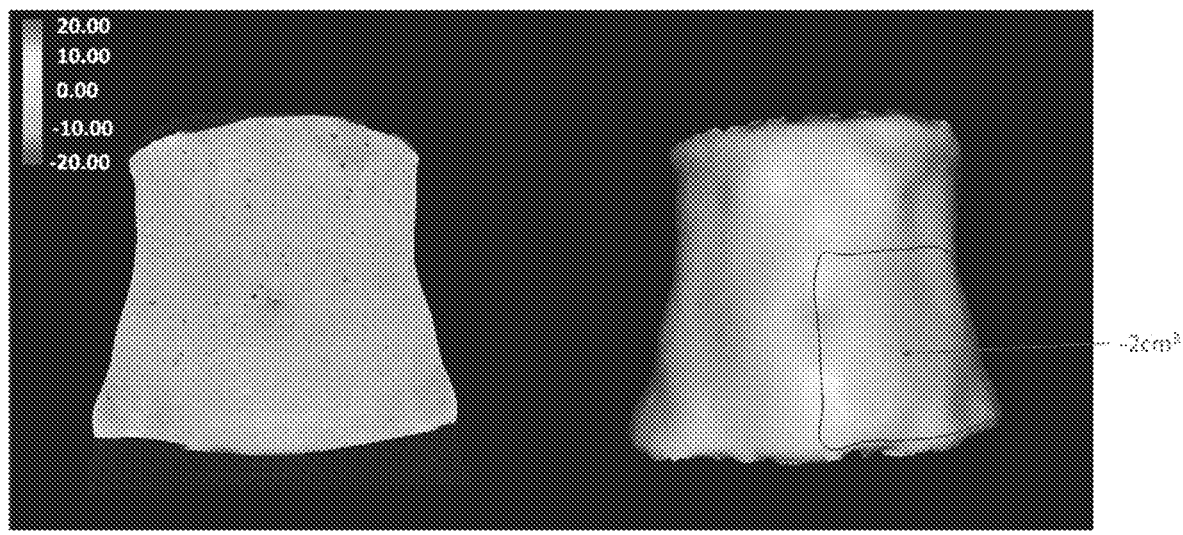

Example 13: Patient Treated with Radiofrequency Followed by Regenerating Body Complex Administration A patient underwent Vanquish ME procedure, which is a radiofrequency "hot" CoolSculpting technology. The right side of the lower abdomen below the umbilicus of the patient was administered topically regenerating body complex (Exemplary Formula 1M) following the procedure. 3D photos were taken with the QuantifiCare LifeViz® Infinity camera and software imaging system (FIGS. 15A-15C). As seen in FIGS. 15A-15C taken at week 5, 3D photos demonstrate volume and contour changes and the color scale represents volume changes in $cm^3$. The color scale is as follows: blue color represents volume reduction, red is volume increase and yellow is neutral (no change). There was a marked reduction on the right side (arrow, FIG. 15A) and further quantified as seen in FIGS. 15B-15C. There was a 40 $cm^3$ reduction as seen in FIG. 15B and a 2 $cm^3$ reduction as seen in FIG. 15C.

Figure 16A:
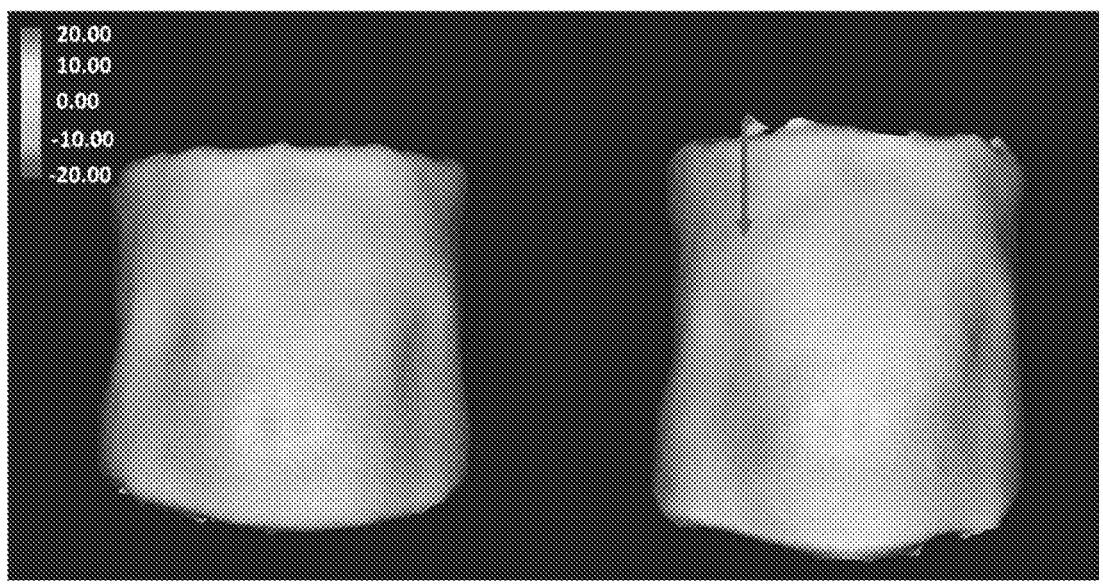
FIGS. 16A-16C show images of an abdomen of a patient treated with cryolipolysis followed by regenerating body complex.
Figure 16B:
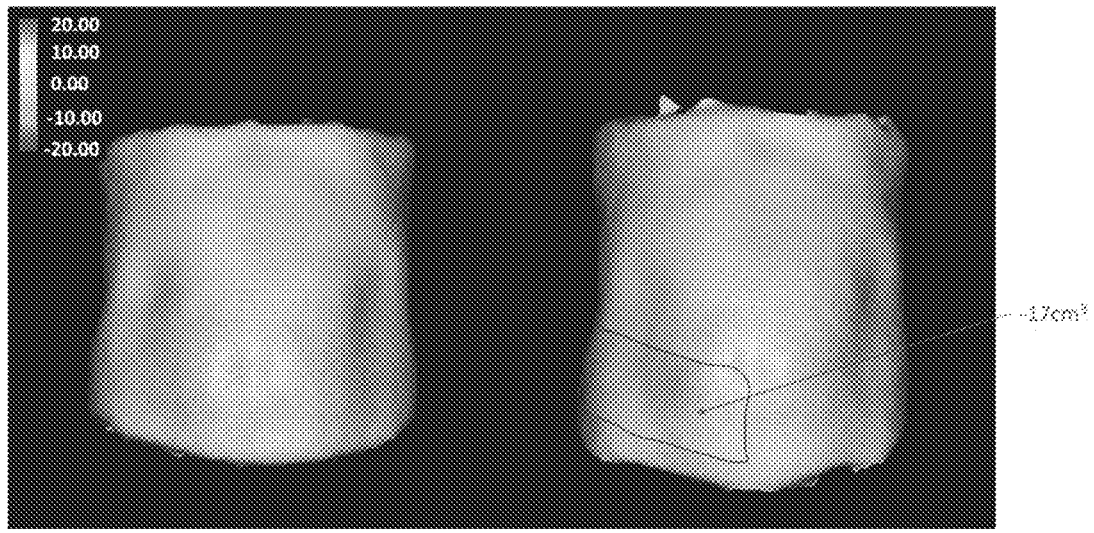
Figure 16C:
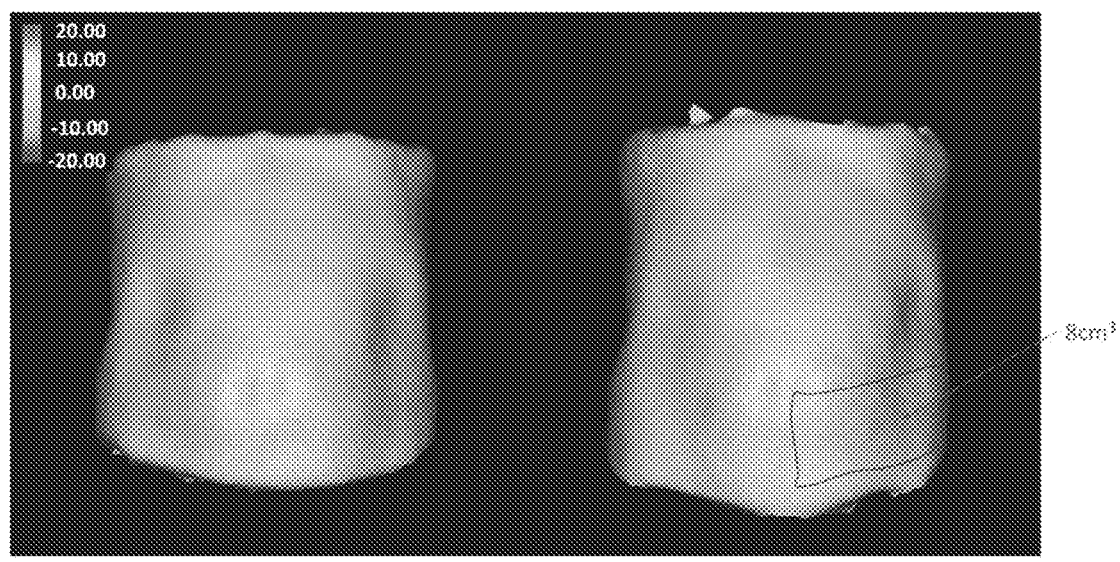

Example 14: Patient Treated with CoolSculpting Procedure Followed by Regenerating Body Complex Administration A patient underwent CoolSculpting procedure. The right side of the lower abdomen below the umbilicus of the patient was administered topically regenerating body complex (Exemplary Formula 1M) following the procedure. 3D photos were taken with the QuantifiCare LifeViz® Infinity camera and software imaging system (FIGS. 16A-16C). As seen in FIGS. 16A-16C taken at week 11, 3D photos demonstrate volume and contour changes and the color scale represents volume changes in $cm^3$. The color scale is as follows: blue color represents volume reduction, red is volume increase and yellow is neutral (no change). There was a marked reduction on the right side (arrow, FIG. 16A) and further quantified as seen in FIGS. 16B-16C. There was a 17 $cm^3$ reduction as seen in FIG. 16B and an 8 $cm^3$ change as seen in FIG. 16C.

Figure 17:
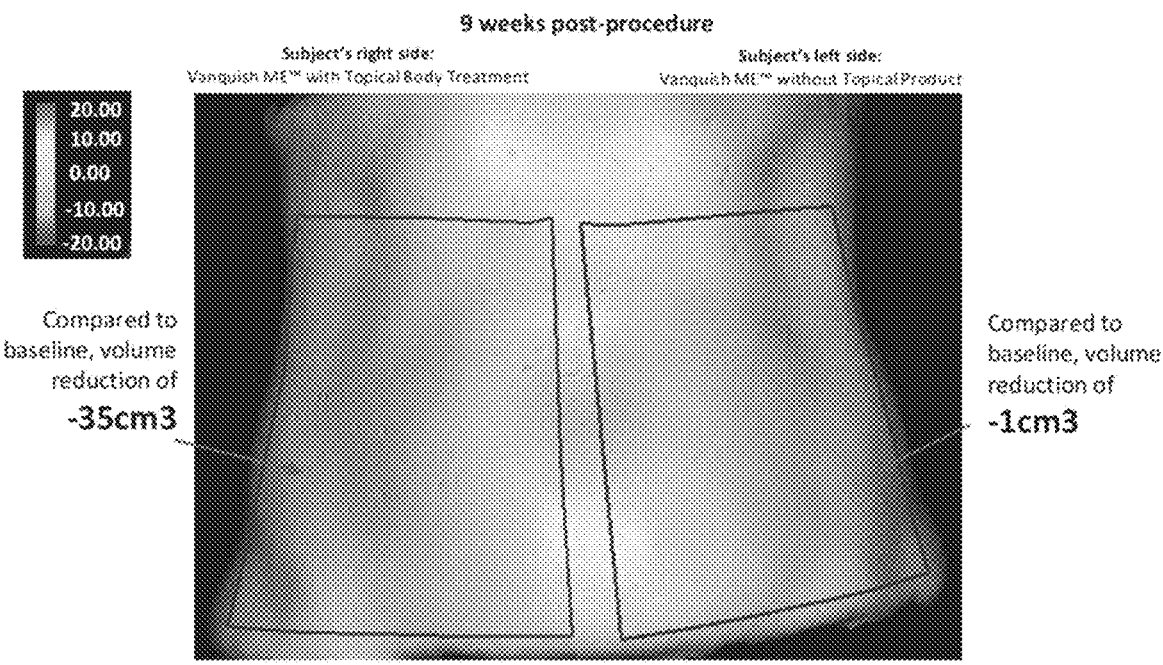
FIG. 17 shows an image of an abdomen and flanking region of a subject treated with a body sculpting device followed by regenerating body complex 9 weeks post-procedure.

Example 15: Acceleration of Fat Reduction in Patient Treated with Body Sculpting Device Followed by Regenerating Body Complex Administration A subject received a Vanquish ME™ (BTL Aesthetics) fat reduction procedure on both sides of the lower abdomen and flanks. Subject followed-up treatment with a split abdomen regimen that included the regenerating body complex (Exemplary Formula 1M) on the subject's right side and no topical treatment on the patient's left side (only the procedure treatment). Results are seen in FIG. 17. FIG. 17 shows 3D volume map results after 9 weeks post-procedure. The blue color represents volume reduction and red color represents volume increase. Treatment of the regenerating body complex on the subject's right side resulted in a volume reduction of 35 $cm^3$ as compared to the subject's left side that received no topical treatment resulting in a reduction of 1 $cm^3$ (FIG. 17).

Figure 18:
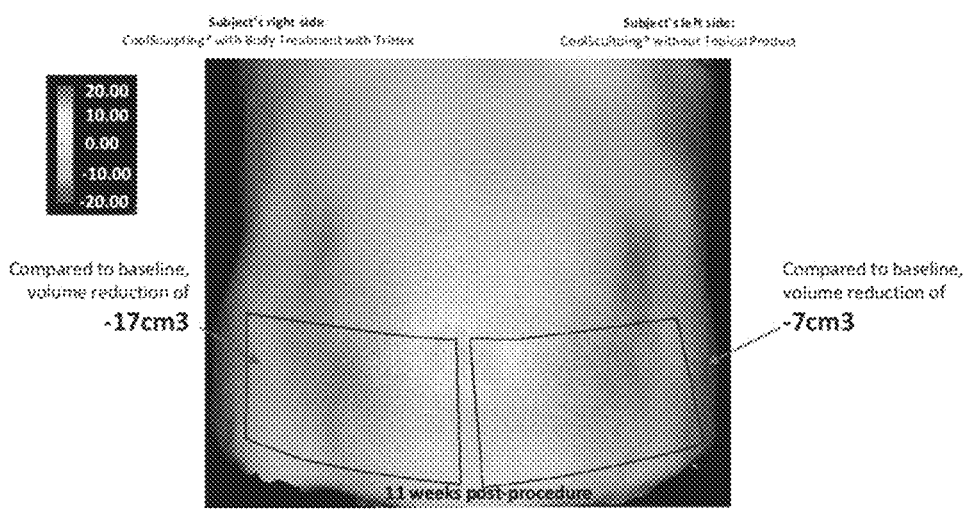
FIG. 18 shows an image of an abdomen of a subject treated with cryolipolysis followed by regenerating body complex 11 weeks post-procedure.

Example 16: Acceleration of Fat Reduction in Patient Treated with Body Sculpting Device Followed by Regenerating Body Complex Administration A subject received a CoolSculpting fat reduction procedure on both sides of the lower abdomen. Subject followed-up treatment with a split abdomen regimen that included the regenerating body complex (Exemplary Formula 1M) on the subject's right side and no topical treatment on the patient's left side (only the procedure treatment). Results are seen in FIG. 18. FIG. 18 shows a 3D volume map results after 11 weeks post-procedure. The blue color represents volume reduction and red color represents volume increase. Treatment of the regenerating body complex on the subject's right side resulted in a volume reduction of 17 $cm^3$ as compared to the subject's left side that received no topical treatment resulting in a reduction of 7 $cm^3$ (FIG. 18).

Example 17: Acceleration of Fat Reduction in Patient Treated with Body Sculpting Device Followed by Regenerating Body Complex Administration after 5 Weeks A subject received a CoolSculpting fat reduction procedure on both sides of the lower abdomen and flanks. Subject followed-up treatment with a split abdomen regimen that included the regenerating body complex (Exemplary Formula 1M) on the subject's right side and no topical treatment on the patient's left side (only the procedure treatment). The case study photos were taken with the QuantifiCareLifeViz® Infinity camera and software imaging system. 3D photos are displayed in the software's clay mode to reveal volume and contour changes. The color scale and volume map represent volume changes in $cm^3$. The blue color represents volume reduction and red color represents volume increase.

Figure 19:
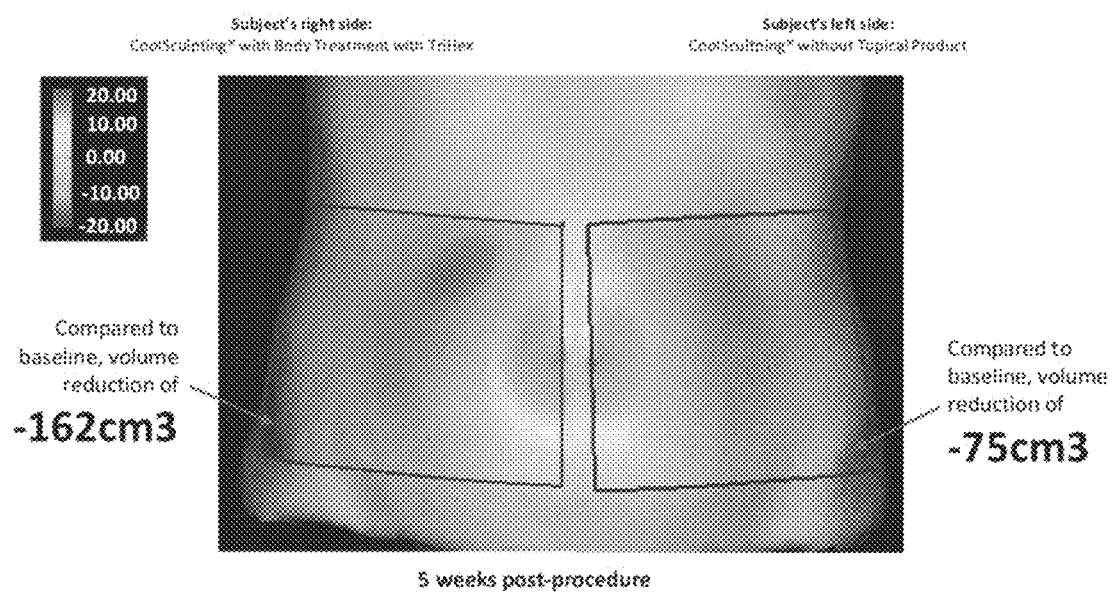
FIG. 19 shows an image of an abdomen and flanking region of a subject treated with a body sculpting device followed by regenerating body complex 5 weeks post-procedure.

Results are seen in FIG. 19. FIG. 19 shows a 3D volume map results after 5 weeks post-procedure. Treatment of the regenerating body complex on the subject's right side resulted in a volume reduction of 162 $cm^3$ as compared to the subject's left side that received no topical treatment resulting in a reduction of 75 $cm^3$ (FIG. 19).

The above description presents the best mode contemplated for carrying out the present disclosure, and of the manner and process of making and using it, in such full, clear, concise, and exact terms as to enable any person skilled in the art to which it pertains to make and use this disclosure. This disclosure is, however, susceptible to modifications and alternate constructions from that discussed above that are fully equivalent. Consequently, this disclosure is not limited to the particular embodiments disclosed. On the contrary, this disclosure covers all modifications and alternate constructions coming within the spirit and scope of the disclosure as generally expressed by the following claims, which particularly point out and distinctly claim the subject matter of the disclosure. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the disclosure, but instead as merely intended to highlight alternative or additional features that may or may not be utilized in a particular embodiment of the disclosure. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should

NUMBERED EMBODIMENTS

Numbered embodiment 1 comprises a topical composition for improving skin laxity or body contouring, comprising: one or more tripeptides, one or more tetrapeptides, and one or more hexapeptides, wherein the topical composition improves skin laxity or body contouring. Numbered embodiment 2 comprises the topical composition of numbered embodiment 1, wherein a tripeptide of the one or more tripeptides is present at 1-10 ppm. Numbered embodiment 3 comprises the topical composition of numbered embodiments 1-2, wherein a tripeptide of the one or more tripeptides is tripeptide-1. Numbered embodiment 4 comprises the topical composition of numbered embodiments 1-3, wherein the tripeptide-1 comprises palmitoyl tripeptide-1, myristoyl tripeptide-1, or a combination thereof. Numbered embodiment 5 comprises the topical composition of numbered embodiments 1-4, wherein a tetrapeptide of the one or more tetrapeptides is present at 1-10 ppm. Numbered embodiment 6 comprises the topical composition of numbered embodiments 1-5, wherein a tetrapeptide of the one or more tetrapeptides is tetrapeptide-2. Numbered embodiment 7 comprises the topical composition of numbered embodiments 1-6, wherein the tetrapeptide-2 comprises acetyl tetrapeptide-2. Numbered embodiment 8 comprises the topical composition of numbered embodiments 1-7, wherein a first hexapeptide of the one or more hexapeptides is present at 0.5-10 ppm. Numbered embodiment 9 comprises the topical composition of numbered embodiments 1-8, wherein a first hexapeptide of the one or more hexapeptides is hexapeptide-12. Numbered embodiment 10 comprises the topical composition of numbered embodiments 1-9, wherein the hexapeptide-12 comprises palmitoyl hexapeptide-12, myristoyl hexapeptide-12, or a combination thereof. Numbered embodiment 11 comprises the topical composition of numbered embodiments 1-10, wherein a second hexapeptide of the one or more hexapeptides comprises a different amino acid sequence. Numbered embodiment 12 comprises the topical composition of numbered embodiments 1-11, wherein the second hexapeptide is present at 0.001-1 ppm. Numbered embodiment 13 comprises the topical composition of numbered embodiments 1-12, wherein the second hexapeptide is hexapeptide-11. Numbered embodiment 14 comprises the topical composition of numbered embodiments 1-13, wherein the second hexapeptide is formulated in a liposome. Numbered embodiment 15 comprises the topical composition of numbered embodiments 1-14 further comprising ceramide NP, *Tremella fuciformis* extract, niacinamide, hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. Numbered embodiment 16 comprises a method for improving skin laxity or body contouring, comprising: administering a topical composition comprising one or more tripeptides, one or more tetrapeptides, and one or more hexapeptides, wherein the topical composition improves skin laxity or body contouring. Numbered embodiment 17 comprises the method of numbered embodiments 1-16, wherein the topical composition is administered in conjunction with a body-shaping procedure. Numbered embodiment 18 comprises the method of numbered embodiments 1-17, wherein the topical composition is administered following a body-shaping procedure. Numbered embodiment 19 comprises the method of numbered embodiments 1-18, wherein the topical composition is administered up to one day following a body-shaping procedure. Numbered embodiment 20 comprises the method of numbered embodiments 1-19, wherein the body-shaping procedure comprises high frequency focused ultrasound, pulsed focus ultrasound, cryolipolysis, radiofrequency induced electroporation, injectable lipolytic agents, liposuction, or combinations thereof. Numbered embodiment 21 comprises the method of numbered embodiments 1-20, wherein the topical composition is administered in conjunction with a skin-laxity procedure. Numbered embodiment 22 comprises the method of numbered embodiments 1-21, wherein the topical composition is administered following a skin-laxity procedure. Numbered embodiment 23 comprises the method of numbered embodiments 1-22, wherein the topical composition is administered up to one day following a skin-laxity procedure. Numbered embodiment 24 comprises the method of numbered embodiments 1-23, wherein the skin-laxity procedure comprises high frequency focused ultrasound, pulsed focus ultrasound, radiofrequency induced electroporation, or combinations thereof. Numbered embodiment 25 comprises the method of numbered embodiments 1-24, wherein the topical composition is administered in conjunction with a non-invasive fat reduction procedure. Numbered embodiment 26 comprises the method of numbered embodiments 1-25, wherein the topical composition is administered following a non-invasive fat reduction procedure. Numbered embodiment 27 comprises the method of numbered embodiments 1-26, wherein the non-invasive fat reduction procedure comprises low level laser therapy, infrared light, ultrasound, radiofrequency, cryolipolysis, or combinations thereof. Numbered embodiment 28 comprises the method of numbered embodiments 1-27, wherein the topical composition is administered one, two three, four, five, or six times a day. Numbered embodiment 29 comprises the method of numbered embodiments 1-28, wherein the topical composition is administered two times a day. Numbered embodiment 30 comprises the method of numbered embodiments 1-29, wherein the topical composition is administered for at least one week, 2 weeks, 4 weeks, 8 weeks, or 12 weeks. Numbered embodiment 31 comprises the method of numbered embodiments 1-30, wherein a tripeptide of the one or more tripeptides is present at 1-10 ppm. Numbered embodiment 32 comprises the method of numbered embodiments 1-31, wherein a tripeptide of the one or more tripeptides is tripeptide-1. Numbered embodiment 33 comprises the method of numbered embodiments 1-32, wherein the tripeptide-1 comprises palmitoyl tripeptide-1, myristoyl tripeptide-1, or a combination thereof. Numbered embodiment 34 comprises the method of numbered embodiments 1-33, wherein a tetrapeptide of the one or more tetrapeptides is present at 1-10 ppm. Numbered embodiment 35 comprises the method of numbered embodiments 1-34, wherein a tetrapeptide of the one or more tetrapeptides is tetrapeptide-2. Numbered embodiment 36 comprises the method of numbered embodiments 1-35, wherein the tetrapeptide-2 comprises acetyl tetrapeptide-2. Numbered embodiment 37 comprises the method of numbered embodiments 1-36, wherein a first hexapeptide of the one or more hexapeptides is present at 0.5-10 ppm. Numbered embodiment 38 comprises the method of numbered embodiments 1-37, wherein a first hexapeptide of the one or more hexapeptides hexapeptide is hexapeptide-12. Numbered embodiment 39 comprises the method of numbered embodiments 1-38, wherein the hexapeptide-12 comprises palmitoyl hexapeptide-12, myristoyl hexapeptide-12, or a combination thereof. Numbered embodiment 40 comprises the method of numbered embodiments 1-39, wherein a second hexapeptide of the one or more hexapeptides comprises a different amino acid sequence. Numbered embodiment 41 comprises the method of numbered embodiments 1-40, wherein the second hexapeptide is present at 0.001-1 ppm. Numbered embodiment 42 comprises the method of numbered embodiments 1-41, wherein the second hexapeptide is hexapeptide-11. Numbered embodiment 43 comprises the method of numbered embodiments 1-42, wherein the second hexapeptide is formulated in a liposome. Numbered embodiment 44 comprises the method of numbered embodiments 1-43, wherein the topical composition further comprises ceramide NP, *Tremella fuciformis* extract, niacinamide, hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof.

---

The invention claimed is:

1. A topical composition for improving skin laxity, texture or crepiness, or for improving body contouring, comprising:
   a tripeptide-1 present at 1-10 ppm,
   a hexapeptide-11 present at about 0.001% to about 6% by weight, and
   a hexapeptide-12 present at 0.5-10 ppm,
   wherein the topical composition improves skin laxity or body contouring.

2. The topical composition of claim 1, further comprising a tetrapeptide.

3. The topical composition of claim 2, wherein the tetrapeptide is tetrapeptide-2.

4. The topical composition of claim 2, wherein the tetrapeptide is present at 1-10 ppm.

5. The topical composition of claim 1, further comprising ceramide NP, *Tremella fuciformis* extract, niacinamide, hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof.

6. A method for improving skin laxity, texture or crepiness, or for improving body contouring, comprising administering the topical composition of claim 1, wherein the topical composition improves skin laxity or body contouring.

7. The method of claim 6, wherein the topical composition is administered in conjunction with a body-shaping procedure or following a body-shaping procedure.

8. The method of claim 6, wherein the topical composition is administered up to one day following a body-shaping procedure.

9. The method of claim 8, wherein the body-shaping procedure comprises high frequency focused ultrasound, pulsed focus ultrasound, cryolipolysis, radiofrequency induced electroporation, injectable lipolytic agents, liposuction, or combinations thereof.

10. The method of claim 6, wherein the topical composition is administered one, two, three, four, five, or six times a day.

11. The method of claim 6, wherein the topical composition is administered for at least one week, 2 weeks, 4 weeks, 8 weeks, or 12 weeks.

12. The method of claim 7, wherein the body-shaping procedure is an invasive procedure.

13. The method of claim 7, wherein the topical composition aids in eliminating post-surgical fat fragmentation and its effects.

14. The topical composition of claim 1, wherein the hexapeptide-11 is present at about 0.002% to about 4% by weight.

15. The topical composition of claim 14, wherein the hexapeptide-11 is present at about 0.005% to about 0.02% by weight.

* * * * *